US008637249B2

(12) United States Patent
Reshatoff, Jr. et al.

(10) Patent No.: US 8,637,249 B2
(45) Date of Patent: Jan. 28, 2014

(54) **COMPOSITIONS, KITS AND METHODS FOR DETECTION OF *CAMPYLOBACTER* NUCLEIC ACID**

(75) Inventors: Michael R. Reshatoff, Jr., San Diego, CA (US); Jennifer J. Bungo, San Diego, CA (US); Shannon K. Kaplan, San Diego, CA (US); James J. Hogan, Coronado, CA (US)

(73) Assignee: Gen-Probe Incorporated, San Diego, CA (US)

( * ) Notice: Subject to any disclaimer, the term of this patent is extended or adjusted under 35 U.S.C. 154(b) by 815 days.

(21) Appl. No.: 12/618,910

(22) Filed: Nov. 16, 2009

(65) Prior Publication Data

US 2010/0124749 A1   May 20, 2010

Related U.S. Application Data

(60) Provisional application No. 61/114,547, filed on Nov. 14, 2008.

(51) Int. Cl.
*C12Q 1/68* (2006.01)
*C12P 19/34* (2006.01)
*C07H 21/02* (2006.01)

(52) U.S. Cl.
USPC .................. 435/6.12; 435/91.2; 536/24.33

(58) Field of Classification Search
None
See application file for complete search history.

(56) References Cited

U.S. PATENT DOCUMENTS

| | | | |
|---|---|---|---|
| 5,004,682 A | 4/1991 | Roberts et al. | |
| 5,447,848 A | 9/1995 | Barns et al. | |
| 5,457,025 A | 10/1995 | Collins et al. | |
| 5,494,795 A | 2/1996 | Guerry et al. | |
| 5,529,910 A | 6/1996 | Ohashi et al. | |
| 5,571,674 A | 11/1996 | Hoshina et al. | |
| 5,610,060 A | 3/1997 | Ward et al. | |
| 5,639,602 A | 6/1997 | Rashtchian et al. | |
| 5,663,049 A | 9/1997 | Barns et al. | |
| 5,674,684 A | 10/1997 | Hogan et al. | |
| 5,679,520 A | 10/1997 | Hogan et al. | |
| 5,691,138 A | 11/1997 | Guesdon et al. | |
| 5,695,931 A | 12/1997 | Labigne | |
| 5,695,960 A | 12/1997 | Chan et al. | |
| 5,723,294 A | 3/1998 | Glass et al. | |
| 5,738,847 A | 4/1998 | Braun | |
| 5,756,701 A | 5/1998 | Wu et al. | |
| 5,811,237 A | 9/1998 | Labigne | |
| 5,843,669 A | 12/1998 | Kaiser et al. | |
| 5,846,783 A | 12/1998 | Wu et al. | |
| 5,861,256 A | 1/1999 | Glass et al. | |
| 5,874,300 A | 2/1999 | Blaser et al. | |
| 5,945,282 A | 8/1999 | Rossau et al. | |
| 5,981,189 A | 11/1999 | Chan et al. | |
| 5,998,138 A | 12/1999 | Stonnet et al. | |
| 6,001,565 A | 12/1999 | Fox et al. | |
| 6,013,501 A | 1/2000 | Chan et al. | |
| 6,066,461 A | 5/2000 | McMillian et al. | |
| 6,080,547 A | 6/2000 | Fox et al. | |
| 6,087,105 A | 7/2000 | Chan et al. | |
| 6,150,517 A | 11/2000 | Hogan et al. | |
| 6,156,546 A | 12/2000 | Konkel et al. | |
| 6,166,196 A | 12/2000 | McMillian et al. | |
| 6,221,582 B1 | 4/2001 | Giesendorf et al. | |
| 6,245,516 B1 | 6/2001 | Al Rashid et al. | |
| 6,277,577 B1 | 8/2001 | Rossau et al. | |
| 6,355,435 B1 | 3/2002 | Wilson et al. | |
| 6,372,424 B1 * | 4/2002 | Brow et al. ................ 435/5 |
| 6,468,743 B1 | 10/2002 | Romick et al. | |
| 6,593,114 B1 | 7/2003 | Kunsch et al. | |
| 6,608,190 B1 | 8/2003 | Bramucci et al. | |
| 6,656,689 B2 | 12/2003 | Rossau et al. | |
| 6,673,616 B1 | 1/2004 | Dahlberg et al. | |
| 6,737,248 B2 | 5/2004 | Kunsch et al. | |
| 6,821,770 B1 | 11/2004 | Hogan | |
| 7,094,893 B2 | 8/2006 | Bramucci et al. | |
| 7,214,492 B1 | 5/2007 | Rublee et al. | |
| 7,303,870 B2 | 12/2007 | Hunter et al. | |
| 2002/0048762 A1 | 4/2002 | Rossau et al. | |
| 2002/0055116 A1 | 5/2002 | Cunnungham et al. | |
| 2002/0061569 A1 | 5/2002 | Haselbeck et al. | |
| 2003/0054338 A1 | 3/2003 | Brow et al. | |
| 2003/0113757 A1 | 6/2003 | Czajka | |
| 2003/0152916 A1 | 8/2003 | Kacian et al. | |
| 2004/0053320 A1 | 3/2004 | Rossau et al. | |
| 2004/0072239 A1 | 4/2004 | Renaud et al. | |

(Continued)

FOREIGN PATENT DOCUMENTS

| | | |
|---|---|---|
| EP | 0 350 392 A2 | 7/1989 |
| EP | 0 425 217 A2 | 10/1990 |

(Continued)

OTHER PUBLICATIONS

Burnett, TA. et al. Speciating *Campylobacter jejuni* and *Campylobacter Coli* isolates from poultry and humans using six PCR-based assays. FEMS Microbiology Letters, vol. 216, p. 201-209, 2002.*

Churruca, E. et al. Detection of *campylobacter jejuni* and *campylobacter coli* in chicken meat samples by real-time nucleic acid sequence-based amplification with molecular beacons. Int. J. Food Microbiol., vol. 117, p. 85-90, 2007.*

Genbank Accession No. BX119966, "Zebrafish DNA sequence from clone CH211-266N15, complete sequence," Dec. 6, 2003 [Retrieved from the Internet Feb. 10, 2010: <http://ncbi.nlm.nih.gov/nuccore/BX119966?log$=ACCN>].

Genbank Accession No. AC185373, "NISC Comparative Sequencing Initiative," May 11, 2006 [Retrieved from the Internet Feb. 11, 2010: <http://ncbi.nlm.nih.gov/nuccore/95102109>].

(Continued)

*Primary Examiner* — Prabha Chunduru
(74) *Attorney, Agent, or Firm* — Jeffrey E. Landes

(57) ABSTRACT

The disclosed invention is related to compositions, kits and methods comprising one or more oligomers targeting 16S rRNA target nucleic acid from *Campylobacter* species *jejuni*, *coli* and/or *lari*. Compositions include amplification oligomers, detection probe oligomers and/or target capture oligomers. Kits and methods comprise at least one of these oligomers.

15 Claims, 2 Drawing Sheets

(56) References Cited

U.S. PATENT DOCUMENTS

| | | |
|---|---|---|
| 2004/0185446 A1 | 9/2004 | Jones et al. |
| 2004/0214302 A1* | 10/2004 | Anthony et al. ............ 435/252.3 |
| 2004/0241644 A1 | 12/2004 | Samadpour |
| 2005/0053962 A1 | 3/2005 | Blackburn et al. |
| 2005/0123946 A1 | 6/2005 | Snaidr et al. |
| 2005/0123954 A1 | 6/2005 | Feldsine |
| 2005/0153282 A1 | 7/2005 | Linnen et al. |
| 2005/0158716 A1 | 7/2005 | Dahlberg et al. |
| 2005/0260603 A1 | 11/2005 | Denise et al. |
| 2005/0260619 A1 | 11/2005 | Brousseau et al. |
| 2006/0046246 A1 | 3/2006 | Zeng et al. |
| 2006/0051752 A1 | 3/2006 | Wang et al. |
| 2006/0160121 A1 | 7/2006 | Mounts et al. |
| 2007/0269813 A1 | 11/2007 | Dewhirst et al. |
| 2008/0038244 A1 | 2/2008 | Glover et al. |
| 2008/0124733 A1 | 5/2008 | Fukui et al. |
| 2008/0268452 A1 | 10/2008 | Kaplan et al. |

FOREIGN PATENT DOCUMENTS

| | | |
|---|---|---|
| EP | 1921158 A1 * | 5/2008 |
| JP | 5-276999 A | 10/1993 |
| JP | 06090795 A2 | 4/1994 |
| JP | 06090796 A2 | 4/1994 |
| JP | 2003164282 A2 | 6/2003 |
| JP | 2003284559 A | 10/2003 |
| JP | 2007068413 A | 3/2007 |
| WO | 98/42842 A2 | 10/1998 |
| WO | 99/24578 A2 | 5/1999 |
| WO | 00/22430 A1 | 4/2000 |
| WO | 00/52203 A2 | 9/2000 |
| WO | 00/58505 A1 | 10/2000 |
| WO | 01/23604 A2 | 4/2001 |
| WO | 01/40497 A2 | 6/2001 |
| WO | 01/55314 A2 | 8/2001 |
| WO | 01/57182 A2 | 8/2001 |
| WO | 01/57274 A2 | 8/2001 |
| WO | 01/59063 A2 | 8/2001 |
| WO | 01/64835 A2 | 9/2001 |
| WO | 02/077186 A2 | 10/2002 |
| WO | 02/079476 A2 | 10/2002 |
| WO | 02/086097 A2 | 10/2002 |
| WO | 02/092818 A2 | 11/2002 |
| WO | 02/097031 A2 | 12/2002 |
| WO | 02/099109 A2 | 12/2002 |
| WO | 03/000865 A2 | 1/2003 |
| WO | 03/004623 A2 | 1/2003 |
| WO | 03/106676 A2 | 12/2003 |
| WO | 2004/024944 A2 | 3/2004 |
| WO | 2005/027731 A2 | 3/2005 |
| WO | 2005/083122 A2 | 9/2005 |
| WO | 2006/029522 A2 | 3/2006 |
| WO | 2006/115199 A2 | 11/2006 |
| WO | 2007/047912 A2 | 4/2007 |
| WO | 2008/016988 A1 | 2/2008 |
| WO | 2008/041354 A2 | 4/2008 |

OTHER PUBLICATIONS

Genbank Accession No. AC187781, "The sequence of Zea mays bac clone CH201-162N3," Sep. 13, 2007 [Retrieved from the Internet Feb. 11, 2010: <http://ncbi.nlm.nih.gov/nuccore/157151864>].

Intl. Search Rpt. and Written Opinion in corresponding PCT application for PCT/US09/64516 dated Mar. 3, 2010.

Klena et al., "Differentiation of *Campylobacter coli, Campylobacter jejuni, Campylobacter lari*, and *Campylobacter upsaliensis* by a Multiplex PCR Developed from the Nucleotide Sequence of the Lipid A Gene IpxA," J. Clin. Microbiol., Dec. 2004, pp. 5549-5557, vol. 42(12), American Society for Microbiology, Washington, D.C.

Chan et al., "The Absence of Intervening Sequences in 23S rRNA Genes of *Campylobacter coli* isolates from Turkeys is a unique attribute of a cluster of related strains which also lack re3sistance to erythromycin," J. Clin. Microbiol., Feb. 2007, pp. 1208-1214, vol. 73(4), American Society for Microbiology, Washington, D.C.

Hannis et al., "High-Resolution Genotyping of *Campylobacter* Species by use of PCR and High-Throughput Mass Spectrometry," J. Clin. Microbiol., Aug. 2008, pp. 1220-1225, vol. 46(4), American Society for Microbiology, Washington, D.C.

Hogan et al., "P-000 Rapid Method of Detecting *Listeria* genus, *Salmonella* genus, and *Camplobacter* using Real Time Transcription-mediated amplification assays targeted to ribosomal RNA," Abstract and Poster, American Society for Microbiology 108th General Meeting, Jun. 1-5, 2008, Boston MA.

PCT International Preliminary Report of Patentability, International Application No. PCT/US2009/064516, May 26, 2011.

Patent Examination Report No. 1, Australian Patent Application No. 2009313808, mailed Sep. 6, 2012.

Extended European Search Report, European Patent Application No. 09826888.1, mailed Sep. 27, 2012.

P. S. Lubeck et al: "Toward an International Standard for PCR-Based Detection of Food-Borne Thermotolerant *Campylobacters*: Assay Development and Analytical Validation", Applied and Environmental Microbiology, vol. 69, No. 9, Sep. 1, 2003, pp. 5664-5669, XP55037859.

Olsen J et al: "Probes and polymerase chain reaction for detection of food-borne bacterial pathogens", International Journal of Food Microbiology, vol. 28, No. 1, Nov. 1, 1995, pp. 1-78, XP027287750.

Perelle S et al: "A LightCycler real-time PCR hybridization probe assay for detecting food-borne thermophilic *Campylobacter*", Molecular and Cellular Probes, vol. 18, No. 5, Oct. 1, 2004, pp. 321-327, XP004523907.

Lehtola M J et al: "Advantages of peptide nucleic acid oligonucleotides for sensitive site directed 16S rRNA fluorescence in situ hybridization (FISH) detection of *Campylobacter jejuni, Campylobacter coli* and *Campylobacter lari*", Journal of Microbiological Methods, vol. 62, No. 2, Aug. 1, 2005, pp. 211-219, XP027746438.

Database Geneseq [Online] Oct. 19, 2006, "Intestine tract pathogenic bacteria detection DNA probe—SEQ ID 40.", XP002683341, retrieved from EBI Database accession AEJ89751; & CN 1 683565 A (Radiation Medical Inst Academy [CN]), Oct. 19, 2005.

Database Geneseq [Online] May 24, 1994, "*Campylobacter* bacteria probe.", XP002683342, retrieved from EBI Database accession No. AAQ51 650; & J P 5 276999 A, Oct. 26, 1993.

* cited by examiner

5' → 3'

AGTGAACGCTGGCGGCGTGCCTAATACATGCAAGTCGAACGATGAAGCTTCTAGCTTGCTAG
AAGTGGATTAGTGGCGCACGGGTGAGTAAGGTATAGTTAATCTGCCCTACACAAGAGGACAA
CAGTTGGAAACGACTGCTAATACTCTATACTCCTGCTTAACACAAGTTGAGTAGGGAAAGTT
TTTCGGTGTAGGATGAGACTATATAGTATCAGCTAGTTGGTAAGGTAATGGCTTACCAAGGC
TATGACGCTTAACTGGTCTGAGAGGATGATCAGTCACACTGGAACTGAGACACGGTCCAGAC
TCCTACGGGAGGCAGCAGTAGGGAATATTGCGCAATGGGGGAAACCCTGACGCAGCAACGCC
GCGTGGAGGATGACACTTTTCGGAGCGTAAACTCCTTTTCTTAGGGAAGAATTCTGACGGTA
CCTAAGGAATAAGCAC

AGTGAACGCTGGCGGCGTGCCTAATACATGCAAGTCGAACGATGAAGCTTCTAGCTTGC
TAGAAGTGGATTAGTGGCGCACGGGTGAGTAAGGTATAGTTAATCTGCCCTACACAAGA
GGACAACAGTTGGAAACGACTGCTAATACTCTATACTCCTGCTTAACACAAGTTGAGTA
GGGAAAGTTTTTCGGTGTAGGATGAGACTATATAGTATCAGCTAGTTGGTAAGGTAATG
GCTTACCAAGGCTATGACGCTTAACTGGTCTGAGAGGATGATCAGTCACACTGGAACTG
AGACACGGTCCAGACTCCTACGGGAGGCAGCAGTAGGGAATATTGCGCAATGGGGAAA
CCCTGACGCAGCAACGCCGCGTGGAGGATGACACTTTTCGGAGCGTAAACTCCTTTTCT
TAGGGAAGAATTCTGACGGTACCTAAGGAATAAGCACCGGCTAACTCCGTGCCAGCAGC
CGCGGTAATACGGAGGGTGCAAGCGTTACTCGGAATCACTGGGCGTAAAGGGCGCGTAG
GCGGATTATCAAGTCTCTTGTGAAATCTAATGGCTTAACCATTAAACTGCTTGGGAAAC
TGATAGTCTAGAGTGAGGGAGAGGCAGATGGAATTGGTGGTGTAGGGGTAAAATCCGTA
GATATCACCAAGAATACCCATTGCGAAGGCGATCTGCTGGAACTCAACTGACGCTAAGG
CGCGAAAGCGTGGGGAGCAAACAGGATTAGATACCCTGGTAGTCCACGCCCTAAACGAT
GTACACTAGTTGTTGGGGTGCTAGTCATCTCAGTAATGCAGCTAACGCATTAAGTGTAC
CGCCTGGGGAGTACGGTCGCAAGATTAAAACTCAAAGGAATAGACGGGGACCCGCACAA
GCGGTGGAGCATGTGGTTTAATTCGAAGATACGCGAAGAACCTTACCTGGGCTTGATAT
CCTAAGAACCTTTTAGAGATAAGAGGGTGCTAGCTTGCTAGAACTTAGAGACAGGTGCT
GCACGGCTGTCGTCAGCTCGTGTCGTGAGATGTTGGGTTAAGTCCCGCAACGAGCGCAA
CCCACGTATTTAGTTGCTAACGGTTCGGCCGAGCACTCTAAATAGACTGCCTTCGTAAG
GAGGAGGAAGGTGTGGACGACGTCAAGTCATCATGGCCCTTATGCCCAGGGCGACACAC
GTGCTACAATGGCATATACAATGAGACGCAATACCGCGAGGTGGAGCAAATCTATAAAA
TATGTCCCAGTTCGGATTGTTCTCTGCAACTCGAGAGCATGAAGCCGGAATCGCTAGTA
ATCGTAGATCAGCCATGCTACGGTGAATACGTTCCCGGGTCTT

SEQUENCE LISTING

```
<160> NUMBER OF SEQ ID NOS: 109

<210> SEQ ID NO 1
<211> LENGTH: 25
<212> TYPE: DNA
<213> ORGANISM: Artificial Sequence
<220> FEATURE:
<223> OTHER INFORMATION: synthetic oligomer

<400> SEQUENCE: 1
caccgaaaaa ctttccctac tcaac                                          25

<210> SEQ ID NO 2
<211> LENGTH: 28
<212> TYPE: DNA
<213> ORGANISM: Artificial Sequence
<220> FEATURE:
<223> OTHER INFORMATION: Synthetic Oligomer

<400> SEQUENCE: 2
ctacaccgaa aactttccc tactcaac                                        28

<210> SEQ ID NO 3
<211> LENGTH: 29
<212> TYPE: DNA
<213> ORGANISM: Artificial Sequence
<220> FEATURE:
<223> OTHER INFORMATION: Synthetic Oligomer

<400> SEQUENCE: 3
cctacaccga aaactttcc ctactcaac                                       29

<210> SEQ ID NO 4
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 4
caccgaaaaa ctttccctac tc                                             22

<210> SEQ ID NO 5
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 5
ctacaccgaa aactttccc tactc                                           25

<210> SEQ ID NO 6
<211> LENGTH: 26
<212> TYPE: DNA
<213> ORGANISM: Artificial Sequence
```

```
<220> FEATURE:
<223> OTHER INFORMATION: Synthetic Oligomer

<400> SEQUENCE: 6
cctacaccga aaactttcc ctactc                                          26

<210> SEQ ID NO 7
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 7
gtctcatcct acaccgaaaa ac                                             22

<210> SEQ ID NO 8
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 8
ctatatagtc tcatcctaca ccg                                            23

<210> SEQ ID NO 9
<211> LENGTH: 30
<212> TYPE: DNA
<213> ORGANISM: Artificial Sequence
<220> FEATURE:
<223> OTHER INFORMATION: Synthetic Oligomer)

<400> SEQUENCE: 9
gctgatacta tatagtctca tcctacaccg                                     30

<210> SEQ ID NO 10
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 10
ctatatagtc tcatcctaca cc                                             22

<210> SEQ ID NO 11
<211> LENGTH: 29
<212> TYPE: DNA
<213> ORGANISM: Artificial Sequence
<220> FEATURE:
<223> OTHER INFORMATION: Synthetic Oligomer

<400> SEQUENCE: 11
gctgatacta tatagtctca tcctacacc                                      29

<210> SEQ ID NO 12
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 12
ctatatagtc tcatcctaca c                                              21
```

```
<210> SEQ ID NO 13
<211> LENGTH: 35
<212> TYPE: DNA
<213> ORGANISM: Artificial Sequence
<220> FEATURE:
<223> OTHER INFORMATION: Synthetic Oligomer

<400> SEQUENCE: 13
ccaactagct gatactatat agtctcatcc tacac                              35

<210> SEQ ID NO 14
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 14
gctgatacta tatagtctca tcc                                          23

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 15
gtgcgccact aatccacttc                                              20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 16
cgtgcgccac taatccactt                                              20

<210> SEQ ID NO 17
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 17
cgtgcgccac taatccact                                               19

<210> SEQ ID NO 18
<211> LENGTH: 50
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 18
aatttaatac gactcactat agggagacct acacaagagg acaacagttg              50

<210> SEQ ID NO 19
<211> LENGTH: 23
<212> TYPE: DNA
<213> ORGANISM: Artificial Sequence
<220> FEATURE:
```

<223> OTHER INFORMATION: Synthetic Oligomer

<400> SEQUENCE: 19
cctacacaag aggacaacag ttg                                        23

<210> SEQ ID NO 20
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 20
aatttaatac gactcactat agggagacct acacaagagg acaacagttg g         51

<210> SEQ ID NO 21
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 21
cctacacaag aggacaacag ttgg                                       24

<210> SEQ ID NO 22
<211> LENGTH: 52
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 22
aatttaatac gactcactat agggagacac aagaggacaa cagttggaaa cg        52

<210> SEQ ID NO 23
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 23
cacaagagga caacagttgg aaacg                                      25

<210> SEQ ID NO 24
<211> LENGTH: 54
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 24
aatttaatac gactcactat agggagacac aagaggacaa cagttggaaa cgac      54

<210> SEQ ID NO 25
<211> LENGTH: 27
<212> TYPE: DNA
<213> ORGANISM: Artificial Sequence -continued

```
<220> FEATURE:
<223> OTHER INFORMATION: Synthetic Oligomer

<400> SEQUENCE: 25
cacaagagga caacagttgg aaacgac                                            27

<210> SEQ ID NO 26
<211> LENGTH: 48
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 26
aatttaatac gactcactat agggagaaag aggacaacag ttggaaac                     48

<210> SEQ ID NO 27
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 27
aagaggacaa cagttggaaa c                                                  21

<210> SEQ ID NO 28
<211> LENGTH: 59
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(28)

<400> SEQUENCE: 28
aatttaatac gactcactat agggagagga caacagttgg aaacgactgc taatactct         59

<210> SEQ ID NO 29
<211> LENGTH: 32
<212> TYPE: DNA
<213> ORGANISM: Artificial Sequence
<220> FEATURE:
<223> OTHER INFORMATION: Synthetic Oligomer

<400> SEQUENCE: 29
ggacaacagt tggaaacgac tgctaatact ct                                      32

<210> SEQ ID NO 30
<211> LENGTH: 56
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 30
aatttaatac gactcactat agggagacaa cagttggaaa cgactgctaa tactct            56

<210> SEQ ID NO 31
<211> LENGTH: 29
<212> TYPE: DNA
```

<213> ORGANISM: Artificial Sequence
<220> FEATURE:
<223> OTHER INFORMATION: Synthetic Oligomer

<400> SEQUENCE: 31
caacagttgg aaacgactgc taatactct                                      29

<210> SEQ ID NO 32
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 32
aatttaatac gactcactat agggagacag ttggaaacga ctgctaatac tct            53

<210> SEQ ID NO 33
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 33
cagttggaaa cgactgctaa tactct                                         26

<210> SEQ ID NO 34
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 34
aatttaatac gactcactat agggagaggc gtgcctaata catgcaagtc g              51

<210> SEQ ID NO 35
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 35
ggcgtgccta atacatgcaa gtcg                                           24

<210> SEQ ID NO 36
<211> LENGTH: 49
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 36
aatttaatac gactcactat agggagacgt gcctaataca tgcaagtcg                49

<210> SEQ ID NO 37
<211> LENGTH: 22

```
<212> TYPE: DNA
<213> ORGANISM: Artificial Sequence
<220> FEATURE:
<223> OTHER INFORMATION: Synthetic Oligomer

<400> SEQUENCE: 37
cgtgcctaat acatgcaagt cg                                              22

<210> SEQ ID NO 38
<211> LENGTH: 49
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 38
aatttaatac gactcactat agggagagcc taatacatgc aagtcgaac                  49

<210> SEQ ID NO 39
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 39
gcctaataca tgcaagtcga ac                                              22

<210> SEQ ID NO 40
<211> LENGTH: 49
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 40
aatttaatac gactcactat agggagacct aatacatgca agtcgaacg                  49

<210> SEQ ID NO 41
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 41
cctaatacat gcaagtcgaa cg                                              22

<210> SEQ ID NO 42
<211> LENGTH: 51
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 42
aatttaatac gactcactat agggagagct agaagtggat tagtggcgca c               51

<210> SEQ ID NO 43
```

```
<211> LENGTH: 24
<212> TYPE: DNA
<213> ORGANISM: Artificial Sequence
<220> FEATURE:
<223> OTHER INFORMATION: Synthetic Oligomer

<400> SEQUENCE: 43
gctagaagtg gattagtggc gcac                                              24

<210> SEQ ID NO 44
<211> LENGTH: 49
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 44
aatttaatac gactcactat agggagagga ttagtggcgc acgggtgag                   49

<210> SEQ ID NO 45
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 45
ggattagtgg cgcacgggtg ag                                                22

<210> SEQ ID NO 46
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 46
aatttaatac gactcactat agggagaggg tgagtaaggt atagttaatc tgc              53

<210> SEQ ID NO 47
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 47
gggtgagtaa ggtatagtta atctgc                                            26

<210> SEQ ID NO 48
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 48
aatttaatac gactcactat agggagaggt gagtaaggta tagttaatct gcc              53
```

```
<210> SEQ ID NO 49
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 49
ggtgagtaag gtatagttaa tctgcc                                              26

<210> SEQ ID NO 50
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 50
caactgttgt cctcttgtg                                                      19

<210> SEQ ID NO 51
<211> LENGTH: 19
<212> TYPE: DNA
<213> ORGANISM: Artificial Sequence
<220> FEATURE:
<223> OTHER INFORMATION: Synthetic Oligomer

<400> SEQUENCE: 51
ctagcaagct agaagcttc                                                      19

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 52
ctaatccact tctagcaagc                                                     20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 53
tcacccgtgc gccactaatc                                                     20

<210> SEQ ID NO 54
<211> LENGTH: 16
<212> TYPE: DNA
<213> ORGANISM: Artificial Sequence
<220> FEATURE:
<223> OTHER INFORMATION: Synthetic Oligomer

<400> SEQUENCE: 54
ttaggcacgc cgccag                                                         16

<210> SEQ ID NO 55
<211> LENGTH: 17
<212> TYPE: DNA
<213> ORGANISM: Artificial Sequence
<220> FEATURE:
<223> OTHER INFORMATION: Synthetic Oligomer

<400> SEQUENCE: 55
```
attaggcacg ccgccag                                          17

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 56
gtagggcaga ttaactatac                                       20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 57
cttgtgtagg gcagattaac                                       20

<210> SEQ ID NO 58
<211> LENGTH: 51
<212> TYPE: DNA
<213> ORGANISM: Artificial Sequence
<220> FEATURE:
<223> OTHER INFORMATION: Synthetic Oligomer

<400> SEQUENCE: 58
kkkkkkkkkk kkkkkkkktt taaaaaaaaa aaaaaaaaaa aaaaaaaaaa a     51

<210> SEQ ID NO 59
<211> LENGTH: 30
<212> TYPE: DNA
<213> ORGANISM: Artificial Sequence
<220> FEATURE:
<223> OTHER INFORMATION: Synthetic Oligomer

<400> SEQUENCE: 59
cggagtatag agtattagca gtcgtctccg                            30

<210> SEQ ID NO 60
<211> LENGTH: 31
<212> TYPE: DNA
<213> ORGANISM: Artificial Sequence
<220> FEATURE:
<223> OTHER INFORMATION: Synthetic Oligomer

<400> SEQUENCE: 60
gcaggagtat agagtattag cagtcgcctg c                          31

<210> SEQ ID NO 61
<211> LENGTH: 21
<212> TYPE: DNA
<213> ORGANISM: Artificial Sequence
<220> FEATURE:
<223> OTHER INFORMATION: Synthetic Oligomer

<400> SEQUENCE: 61
gcaggagtat agagtacctg c                                     21

<210> SEQ ID NO 62
<211> LENGTH: 28
<212> TYPE: DNA
<213> ORGANISM: Artificial Sequence

```
<220> FEATURE:
<223> OTHER INFORMATION: Synthetic Oligomer

<400> SEQUENCE: 62
ccgtgttaag caggagtata gagcacgg                                          28

<210> SEQ ID NO 63
<211> LENGTH: 26
<212> TYPE: DNA
<213> ORGANISM: Artificial Sequence
<220> FEATURE:
<223> OTHER INFORMATION: Synthetic Oligomer

<400> SEQUENCE: 63
ccgtgttaag caggagtata gcacgg                                            26

<210> SEQ ID NO 64
<211> LENGTH: 30
<212> TYPE: DNA
<213> ORGANISM: Artificial Sequence
<220> FEATURE:
<223> OTHER INFORMATION: Synthetic Oligomer

<400> SEQUENCE: 64
ctccctactc aacttgtgtt aagcagggag                                        30

<210> SEQ ID NO 65
<211> LENGTH: 29
<212> TYPE: DNA
<213> ORGANISM: Artificial Sequence
<220> FEATURE:
<223> OTHER INFORMATION: Synthetic Oligomer

<400> SEQUENCE: 65
ctccctactc aacttgtgtt aagcgggag                                         29

<210> SEQ ID NO 66
<211> LENGTH: 25
<212> TYPE: DNA
<213> ORGANISM: Artificial Sequence
<220> FEATURE:
<223> OTHER INFORMATION: Synthetic Oligomer

<400> SEQUENCE: 66
ctccctactc aacttgtgtt gggag                                             25

<210> SEQ ID NO 67
<211> LENGTH: 22
<212> TYPE: DNA
<213> ORGANISM: Artificial Sequence
<220> FEATURE:
<223> OTHER INFORMATION: Synthetic Oligomer

<400> SEQUENCE: 67
ctccctactc aacttgtggg ag                                                22

<210> SEQ ID NO 68
<211> LENGTH: 20
<212> TYPE: DNA
<213> ORGANISM: Artificial Sequence
<220> FEATURE:
<223> OTHER INFORMATION: Synthetic Oligomer

<400> SEQUENCE: 68
ctccctactc aacttgggag                                                   20
```

```
<210> SEQ ID NO 69
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 69
ccgctagaag cttcatcgag cgg                                              23

<210> SEQ ID NO 70
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 70
cggaagcaag ctagaagctt ccg                                              23

<210> SEQ ID NO 71
<211> LENGTH: 56
<212> TYPE: DNA
<213> ORGANISM: Artificial Sequence
<220> FEATURE:
<223> OTHER INFORMATION: Synthetic Oligomer

<400> SEQUENCE: 71
gcgtcagggt ttcccccatt gcgtttaaaa aaaaaaaaa aaaaaaaaaa aaaaaa           56

<210> SEQ ID NO 72
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 72
gcgtcagggt ttcccccatt gcg                                              23

<210> SEQ ID NO 73
<211> LENGTH: 56
<212> TYPE: DNA
<213> ORGANISM: Artificial Sequence
<220> FEATURE:
<223> OTHER INFORMATION: Synthetic Oligomer

<400> SEQUENCE: 73
gcttattcct taggtaccgt cagtttaaaa aaaaaaaaa aaaaaaaaaa aaaaaa           56

<210> SEQ ID NO 74
<211> LENGTH: 23
<212> TYPE: DNA
<213> ORGANISM: Artificial Sequence
<220> FEATURE:
<223> OTHER INFORMATION: Synthetic Oligomer

<400> SEQUENCE: 74
gcttattcct taggtaccgt cag                                              23

<210> SEQ ID NO 75
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
```

```
<222> LOCATION: (1)..(27)

<400> SEQUENCE: 75
aatttaatac gactcactat agggaga                                    27

<210> SEQ ID NO 76
<211> LENGTH: 27
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 76
agagggatat cactcagcat aatttaa                                    27

<210> SEQ ID NO 77
<211> LENGTH: 57
<212> TYPE: DNA
<213> ORGANISM: Campylobacter jejuni

<400> SEQUENCE: 77
gttgagtagg gaaagttttt cggtgtagga tgagactata tagtatcagc tagttgg    57

<210> SEQ ID NO 78
<211> LENGTH: 36
<212> TYPE: DNA
<213> ORGANISM: Campylobacter jejuni

<400> SEQUENCE: 78
gttgagtagg gaaagttttt cggtgtagga tgagac                          36

<210> SEQ ID NO 79
<211> LENGTH: 29
<212> TYPE: DNA
<213> ORGANISM: Campylobacter jejuni

<400> SEQUENCE: 79 gttttcggt gtaggatgag actatatag                                   29

<210> SEQ ID NO 80
<211> LENGTH: 11
<212> TYPE: DNA
<213> ORGANISM: Campylobacter jejuni

<400> SEQUENCE: 80 gttttcggt g                                                      11

<210> SEQ ID NO 81
<211> LENGTH: 14
<212> TYPE: DNA
<213> ORGANISM: Campylobacter jejuni

<400> SEQUENCE: 81
gtgtaggatg agac                                                  14

<210> SEQ ID NO 82
<211> LENGTH: 43
<212> TYPE: DNA
<213> ORGANISM: Campylobacter jejuni

<400> SEQUENCE: 82
gttgagtagg gaaagttttt cggtgtagga tgagactata tag                  43
```

```
<210> SEQ ID NO 83
<211> LENGTH: 165
<212> TYPE: DNA
<213> ORGANISM: Campylobacter jejuni

<400> SEQUENCE: 83
gaagtggatt agtggcgcac gggtgagtaa ggtatagtta atctgcccta cacaagagga      60
caacagttgg aaacgactgc taatactcta tactcctgct taacacaagt tgagtaggga     120 aagttttcg gtgtaggatg agactatata gtatcagcta gttgg                      165

<210> SEQ ID NO 84
<211> LENGTH: 48
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 84
aatttaatac gactcactat agggagacag ttggaaacga ctgctaat                   48

<210> SEQ ID NO 85
<211> LENGTH: 46
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 85
aatttaatac gactcactat agggagacag ttggaaacga ctgcta                     46

<210> SEQ ID NO 86
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 86
aatttaatac gactcactat agggagacaa ttggaaacga ctgctaatac tct             53

<210> SEQ ID NO 87
<211> LENGTH: 53
<212> TYPE: DNA
<213> ORGANISM: Artificial Sequence
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 87
aatttaatac gactcactat agggagacag ttggaaacga ctgccaacac tct             53

<210> SEQ ID NO 88
<211> LENGTH: 50
<212> TYPE: DNA
<213> ORGANISM: Artificial Sequence
```

```
<220> FEATURE:
<223> OTHER INFORMATION: Synthetic Oligomer
<220> FEATURE:
<221> NAME/KEY: promoter
<222> LOCATION: (1)..(27)

<400> SEQUENCE: 88
aatttaatac gactcactat agggagacag ttggaaacga ctgctaacac            50

<210> SEQ ID NO 89
<211> LENGTH: 657
<212> TYPE: DNA
<213> ORGANISM: Campylobacter jejuni

<400> SEQUENCE: 89
agtgaacgct ggcggcgtgc ctaatacatg caagtcgaac gatgaagctt ctagcttgct    60
agaagtggat tagtggcgca cgggtgagta aggtatagtt aatctgccct acacaagagg   120
acaacagttg gaaacgactg ctaatactct atactcctgc ttaacacaag ttgagcaggg   180
aaagtttttc ggtgtaggat gagactatat agtatcagct agttggtaag gtaatggctt   240
accaaggcta tgacgcttaa ctggtctgag aggatgatca gtcacactgg aactgagaca   300
cggtccagac tcctacggga ggcagcagta gggaatattg cgcaatgggg gaaaccctga   360
cgcagcaacg ccgcgtggag gatgacactt ttcggagcgt aaactccttt tcttagggaa   420
gaattctgac ggtacctaag gaataagcac cggctaactc cgtgccagca gccgcggtaa   480
tacggagggt gcaagcgtta ctcggaatca ctgggcgtaa agggcgcgta ggcggattat   540
caagtctctt gtgaaatcta atggcttaac cattaaactg cttgggaaac tgatagtcta   600
gagtgaggga gaggcagatg gaattggtgg tgtaggggta aaatccgtag atatcac      657

<210> SEQ ID NO 90
<211> LENGTH: 650
<212> TYPE: DNA
<213> ORGANISM: Campylobacter jejuni

<400> SEQUENCE: 90
agtgaacgct ggcggcgtgc ctaatacatg caagtcgaac gatgaagctt ctagcttgct    60
agaagtggat tagtggcgca cgggtgagta aggtatagtt aatctgccct acacaagagg   120
acaacagttg gaaacgactg ctaatactct atactcctgc ttaacacaag ttaagtaggg   180
aaagtttttc ggtgtaggat gagactatat agtatcagct agttggtaag gtaatggctt   240
accaaggcta tgacgcttaa ctggtctgag aggatgatca gtcacactgg aactgagaca   300
cggtccagac tcctacggga ggcagcagta gggaatattg cgcaatgggg gaaaccctga   360
cgcagcaatg ccgcgtggag gatgacactt ttcggagcgt aaactccttt tcttagggaa   420
gaattctgac ggtacctaag gaataagcac cggctaactc cgtgccagca gccgcggtaa   480
tacggagggt gcaagcgtta ctcggaatca ctgggcgtaa agggcgcgta ggcggattat   540
caagtctctt gtgaaatcta atggcttaac cattaaactg cttgggaaac tgatagtcta   600
gagtgaggga gaggcagatg gaattggtgg tgtaggggta aaatccgtag              650

<210> SEQ ID NO 91
<211> LENGTH: 1341
<212> TYPE: DNA
<213> ORGANISM: Campylobacter jejuni

<400> SEQUENCE: 91
agtgaacgct ggcggcgtgc ctaatacatg caagtcgaac gatgaagctt ctagcttgct    60
```

```
agaagtggat tagtggcgca cgggtgagta aggtatagtt aatctgccct acacaagagg      120
acaacagttg gaaacgactg ctaatactct atactcctgc ttaacacaag ttgagtaggg      180 aaagttttc  ggtgtaggat gagactatat agtatcagct agttggtaag gtaatggctt     240
accaaggcta tgacgcttaa ctggtctgag aggatgatca gtcacactgg aactgagaca     300
cggtccagac tcctacggga ggcagcagta gggaatattg cgcaatgggg gaaaccctga     360
cgcagcaacg ccgcgtggag gatgacactt ttcggagcgt aaactccttt tcttagggaa     420
gaattctgac ggtacctaag gaataagcac cggctaactc cgtgccagca gccgcggtaa     480
tacggagggt gcaagcgtta ctcggaatca ctgggcgtaa agggcgcgta ggcggattat     540
caagtctctt gtgaaatcta atggcttaac cattaaactg cttgggaaac tgatagtcta     600
gagtgaggga gaggcagatg gaattggtgg tgtaggggta aaatccgtag atatcaccaa     660
gaatacccat tgcgaaggcg atctgctgga actcaactga cgctaaggcg gaaagcgtg      720 gggagcaaac aggattagat accctggtag tccacgccct aaacgatgta cactagttgt     780
tggggtgcta gtcatctcag taatgcagct aacgcattaa gtgtaccgcc tggggagtac     840
ggtcgcaaga ttaaaactca aaggaataga cggggacccg cacaagcggt ggagcatgtg     900
gtttaattcg aagatacgcg aagaacctta cctgggcttg atatcctaag aaccttttag     960
agataagagg gtgctagctt gctagaactt agagacaggt gctgcacggc tgtcgtcagc    1020
tcgtgtcgtg agatgttggg ttaagtcccg caacgagcgc aacccacgta tttagttgct    1080
aacggttcgg ccgagcactc taaatagact gccttcgtaa ggaggaggaa ggtgtggacg    1140
acgtcaagtc atcatggccc ttatgcccag gcgacacac  gtgctacaat ggcatataca    1200
atgagacgca ataccgcgag gtggagcaaa tctataaaat atgtcccagt tcggattgtt    1260
ctctgcaact cgagagcatg aagccggaat cgctagtaat cgtagatcag ccatgctacg    1320
gtgaatacgt tcccgggtct t                                              1341

<210> SEQ ID NO 92
<211> LENGTH: 137
<212> TYPE: DNA
<213> ORGANISM: Campylobacter jejuni

<400> SEQUENCE: 92
ggcgtgccta atacatgcaa gtcgaacgat gaagcttcta gcttgctaga agtggattag      60
tggcgcacgg gtgagtaagg tatagttaat ctgccctaca caagaggaca acagttggaa     120
acgactgcta atactct                                                    137

<210> SEQ ID NO 93
<211> LENGTH: 28
<212> TYPE: DNA
<213> ORGANISM: Campylobacter jejuni

<400> SEQUENCE: 93
ggcgtgccta atacatgcaa gtcgaacg                                         28

<210> SEQ ID NO 94
<211> LENGTH: 51
<212> TYPE: DNA
<213> ORGANISM: Campylobacter jejuni

<400> SEQUENCE: 94
gctagaagtg gattagtggc gcacgggtga gtaaggtata gttaatctgc c               51

<210> SEQ ID NO 95
```

```
<211> LENGTH: 43
<212> TYPE: DNA
<213> ORGANISM: Campylobacter jejuni

<400> SEQUENCE: 95
cctacacaag aggacaacag ttggaaacga ctgctaatac tct                    43

<210> SEQ ID NO 96
<211> LENGTH: 93
<212> TYPE: DNA
<213> ORGANISM: Campylobacter jejuni

<400> SEQUENCE: 96
gctagaagtg gattagtggc gcacgggtga gtaaggtata gttaatctgc cctacacaag   60
aggacaacag ttggaaacga ctgctaatac tct                               93

<210> SEQ ID NO 97
<211> LENGTH: 27
<212> TYPE: DNA
<213> ORGANISM: Campylobacter jejuni

<400> SEQUENCE: 97
cacaagagga caacagttgg aaacgac                                      27

<210> SEQ ID NO 98
<211> LENGTH: 36
<212> TYPE: DNA
<213> ORGANISM: Campylobacter jejuni

<400> SEQUENCE: 98
aagaggacaa cagttggaaa cgactgctaa tactct                            36

<210> SEQ ID NO 99
<211> LENGTH: 18
<212> TYPE: DNA
<213> ORGANISM: Campylobacter jejuni

<400> SEQUENCE: 99
cctaatacat gcaagtcg                                                18

<210> SEQ ID NO 100
<211> LENGTH: 68
<212> TYPE: DNA
<213> ORGANISM: Campylobacter jejuni

<400> SEQUENCE: 100
ggtgagtaag gtatagttaa tctgccctac acaagaggac aacagttgga aacgactgct   60
aatactct                                                           68

<210> SEQ ID NO 101
<211> LENGTH: 11
<212> TYPE: DNA
<213> ORGANISM: Campylobacter jejuni

<400> SEQUENCE: 101
cagttggaaa c                                                       11

<210> SEQ ID NO 102
<211> LENGTH: 48
<212> TYPE: DNA
<213> ORGANISM: Campylobacter jejuni

<400> SEQUENCE: 102
```

```
acgactgcta atactctata ctcctgctta acacaagttg agtaggga                    48
```

<210> SEQ ID NO 103
<211> LENGTH: 23
<212> TYPE: DNA
<213> ORGANISM: Campylobacter jejuni

<400> SEQUENCE: 103

```
gcttaacaca agttgagtag gga                                               23
```

<210> SEQ ID NO 104
<211> LENGTH: 35
<212> TYPE: DNA
<213> ORGANISM: Campylobacter jejuni

<400> SEQUENCE: 104

```
ctctatactc ctgcttaaca caagttgagt aggga                                  35
```

<210> SEQ ID NO 105
<211> LENGTH: 19
<212> TYPE: DNA
<213> ORGANISM: Campylobacter jejuni

<400> SEQUENCE: 105

```
aacacaagtt gagtaggga                                                    19
```

<210> SEQ ID NO 106
<211> LENGTH: 15
<212> TYPE: DNA
<213> ORGANISM: Campylobacter jejuni

<400> SEQUENCE: 106

```
caagttgagt aggga                                                        15
```

<210> SEQ ID NO 107
<211> LENGTH: 21
<212> TYPE: DNA
<213> ORGANISM: Campylobacter jejuni

<400> SEQUENCE: 107

```
aagaggacaa cagttggaaa c                                                 21
```

<210> SEQ ID NO 108
<211> LENGTH: 26
<212> TYPE: DNA
<213> ORGANISM: Campylobacter jejuni

<400> SEQUENCE: 108

```
cagttggaaa cgactgctaa tactct                                            26
```

<210> SEQ ID NO 109
<211> LENGTH: 119
<212> TYPE: DNA
<213> ORGANISM: Campylobacter jejuni

<400> SEQUENCE: 109

```
cctacacaag aggacaacag ttggaaacga ctgctaatac tctatactcc tgcttaacac       60
aagttgagta gggaaagttt ttcggtgtag gatgagacta tatagtatca gctagttgg       119
```

COMPOSITIONS, KITS AND METHODS FOR DETECTION OF *CAMPYLOBACTER* NUCLEIC ACID

CROSS-REFERENCE TO RELATED APPLICATIONS

This application claims the benefit of priority to U.S. Provisional Application No. 61/114,547, filed on Nov. 14, 2008, which is incorporated herein by reference in its entirety.

FIELD OF THE INVENTION

This invention relates to detection of the presence of *Campylobacter jejuni* (*C. jejuni*), *Campylobacter lari* (*C. lari*), or *Campylobacter coli* (*C. coli*) bacteria in a sample by using molecular biological methods, and specifically relates to detection of *C. jejuni*, *C. lari*, or *C. coli* in a sample by amplifying nucleic acids from *C. jejuni*, *C. lari*, or *C. coli* and detecting the amplified nucleic acid sequences.

BACKGROUND

*Campylobacter* contamination is one of the major causes of food-borne illness, and can lead to Campylobacteriosis. *Campylobacter* are also a major cause of diarrhoeal illness in humans and are generally regarded as the most common bacterial cause of gastroenteritis worldwide. In the United States, *Campylobacter* are estimated to affect two million people a year. Common routes of transmission are ingestion of contaminated food, water or milk, eating raw meat, person-to-person sexual contact, and fecal-oral. The infectious dose for *Campylobacter* may be as low as 400-500 bacteria as shown by human feeding studies, however, the infectious dose and the dose response are dependent upon the strains used, and the age and physical condition of the individuals. Symptoms appear 2-10 days after ingesting the bacteria and include fever, abdominal cramps, and mild to severe diarrhea, which may be bloody. Most infections are caused by *C. jejuni*, normally found in cattle, swine, and birds, where it is non-pathogenic, however, the illness may also be caused by *C. coli* (also found in cattle, swine, and birds) and *C. lari* (present in seabirds in particular). Some strains of *C. jejuni* produce a cholera-like enterotoxin, which is important in the watery diarrhea observed in infections. Most *Campylobacter* infections clear on their own or with the aid of antibiotics, however, long-term sequelae include reactive arthritis, Guillain-Barré syndrome and Miller Fisher Syndromes.

Studies have shown that *Campylobacter* can be isolated from a wide variety of sources, including chicken, cattle, pets, goats, sheep and pond water and river water. Milk, particularly unpasteurised (raw) milk, and poultry are the most common food items associated with *Campylobacter* infection. *Campylobacter* may also be isolated from red meat, but the frequency of contamination is generally much lower than poultry. Isolation of *Campylobacter* from food sources is difficult because the bacteria are usually present in very low numbers since they generally do not multiply in the foods they infect. Culture methods require an enrichment broth containing antibiotics, special antibiotic-containing plates, incubation at two different temperatures, and a microaerophilic atmosphere with an elevated concentration of carbon dioxide. Isolation can take several days to a week. Identification of *Campylobacter* using current USDA methods for detection can take 2-3 days. There is a need for a rapid, sensitive and accurate method to detect *C. jejuni*, *C. lari*, or *C. coli* so that the contaminating or infectious source can be accurately detected and eliminated. There is also a need for methods that allow rapid and accurate diagnosis of *C. jejuni*, *C. lari*, or *C. coli* infections in humans so that infected individuals may be treated promptly to limit morbidity and prevent further infections.

SUMMARY

The present invention relates to compositions, kits, and methods used in the detection of common pathogenic strains of *Campylobacter*, particularly, *Campylobacter jejuni*, *Campylobacter coli*, and *Campylobacter lari*. The invention is based at least in part on the discovery that certain *Campylobacter* sequences are surprisingly efficacious for the detection of *Campylobacter*. In certain aspects and embodiments, particular regions of the *Campylobacter* 16S rRNA have been identified as preferred targets for nucleic acid amplification reactions, which provide improvements in relation to specificity, sensitivity, or speed of detection as well as other advantages.

Therefore, according to one embodiment, there are provided compositions for use in a *Campylobacter* nucleic acid amplification assay, wherein the compositions are amplification oligomers for amplifying a *Campylobacter* target nucleic acid. In certain aspects, the compositions include a T7 Provider oligonucleotide and a primer oligonucleotide, both of which are capable of stably hybridizing to a *C. jejuni* target nucleic acid and a *C. coli*, a *C. lari* or a *C. coli* and a *C. lari* target nucleic acid; in which the T7 Provider oligonucleotide is configured to target a sequence in a region of *Campylobacter* nucleic acid corresponding to bases from about 14-150 of GenBank Accession No.: AF393202.1, gi:20378208 16S rRNA (SEQ ID NO:91) and the primer oligonucleotide is configured to target a sequence in a region of *Campylobacter* nucleic acid. Ordinarily skilled artisans will understand that one of the amplification oligomers is configured sense and the other antisense to the reference sequence in order that the amplification oligomers can be used in an amplification assay.

In another embodiment, there are provided kits that include the compositions provided herein. In certain aspects, the kits include a T7 Provider oligonucleotide and a primer oligonucleotide, both of which are capable of stably hybridizing to a *C. jejuni* target nucleic acid and a *C. coli*, a *C. lari* or a *C. coli* and a *C. lari* target nucleic acid, in which the T7 Provider oligonucleotide is configured to target a sequence in a region of *Campylobacter* nucleic acid corresponding to bases from about 14-150 of GenBank Accession No.: AF393202.1, gi:20378208 16S rRNA and the primer oligonucleotide is configured to target a sequence in a region of *Campylobacter* nucleic acid. Ordinarily skilled artisans will understand that one of the amplification oligomers is configured sense and the other antisense to the reference sequence in order that the amplification oligomers can be used in an amplification assay.

In another embodiment, there are provided methods for detecting the presence of *Campylobacter* in a sample using the compositions and/or kits provided herein. In certain aspects, the methods use a T7 Provider oligonucleotide and a primer oligonucleotide that stably hybridizing to a *C. jejuni* target nucleic acid and a *C. coli*, a *C. lari* or a *C. coli* and a *C. lari* target nucleic acid, and in which the T7 Provider oligonucleotide is configured to target a sequence in a region of *Campylobacter* nucleic acid corresponding to bases from about 14-150 of GenBank Accession No.: AF393202.1, gi:20378208 16S rRNA and the primer oligonucleotide is configured to target a sequence in a region of *Campylobacter* nucleic acid. Ordinarily skilled artisans will understand that one of the amplification oligomers is configured sense and the other antisense to the reference sequence in order that the amplification oligomers can be used in an amplification assay.

In one aspect, the T7 Provider is configured to target a sequence in a region of *Campylobacter* nucleic acid corresponding to bases 83-150 of GenBank Accession No.: AF393202.1, gi:20378208. In another aspect, the T7 Provider is configured to target a sequence in a region of *Campylobacter* nucleic acid corresponding to bases 108-150 of GenBank Accession No.: AF393202.1, gi:20378208. In another aspect, the T7 Provider is configured to target a sequence in a region of *Campylobacter* nucleic acid corresponding to bases 115-150 of GenBank Accession No.: AF393202.1, gi:20378208. In another aspect, the T7 Provider is configured to target a sequence in a region of *Campylobacter* nucleic acid corresponding to bases 115-135 of GenBank Accession No.: AF393202.1, gi:20378208. In another aspect, the T7 Provider is configured to target a sequence in a region of *Campylobacter* nucleic acid corresponding to bases 125-150 of GenBank Accession No.: AF393202.1, gi:20378208.

In one aspect, the primer oligonucleotide is configured to target a sequence in a region of *Campylobacter* nucleic acid corresponding to bases from about 62-226 of GenBank Accession No.: AF393202.1, gi:20378208 (SEQ ID NO:91). In another aspect, the primer oligonucleotide is configured to target a sequence in a region of *Campylobacter* nucleic acid corresponding to bases from about 170-226 of GenBank Accession No.: AF393202.1, gi:20378208. In another aspect, the primer oligonucleotide is configured to target a sequence in a region of *Campylobacter* nucleic acid corresponding to bases from about 170-212 of GenBank Accession No.: AF393202.1, gi:20378208. In another aspect, the primer oligonucleotide is configured to target a sequence in a region of *Campylobacter* nucleic acid corresponding to bases 184-212 of GenBank Accession No.: AF393202.1, gi:20378208. In another aspect, the primer oligonucleotide is configured to target a sequence in a region of *Campylobacter* nucleic acid corresponding to bases 170-205 of GenBank Accession No.: AF393202.1, gi:20378208.

In one aspect, the T7 Provider is selected from the sequences of SEQ ID NOS:18, 20, 22, 24, 26, 28, 30, 32, 34, 36, 38, 40, 42, 44, 46, 48, 84, 85, 86, 87, 88 and their complements. In another aspect, the T7 Provider comprises a target hybridization sequence that is selected from the sequences of SEQ ID NOS:19, 21, 23, 25, 27, 29, 31, 33, 35, 37, 39, 41, 43, 45, 47, 49, and their complements; and further comprises a promoter nucleotide sequence selected from the group consisting of; a transcriptional promoter recognized by an RNA Polymerase, a transcriptional promoter recognized by a bacteriophage T7 RNA polymerase, SEQ ID NO:75 and SEQ ID NO:76. In one aspect, the primer oligonucleotide is selected from the sequences of SEQ ID NOS: 1-17 and their complements.

In one preferred embodiment, the T7 Provider is selected from the sequences of SEQ ID NOS:18, 20, 26, 28, 30, 32 and 48. In other preferred embodiments, the primer oligonucleotide selected from the sequences of SEQ ID NOS:1, 4, 7, 8, 10, 12. In one preferred embodiment, the T7 Provider has the sequence of SEQ ID NO:26 and the primer oligonucleotide has the sequence of SEQ ID NO:7. In one preferred embodiment, the T7 Provider has the sequence of SEQ ID NO:32 and the primer oligonucleotide has the sequence of SEQ ID NO:8.

In certain embodiments of the compositions, methods and kits, a T7 Provider oligonucleotide is configured to comprise a target hybridizing sequence that is 21-32 nucleotides in length and that is at least 70%; or 75%; or 80%; or 85%; or 90%; or 100% complementary to a sequence in a region of *Campylobacter* nucleic acid corresponding to bases 83-150 of GenBank Accession No.: AF393202.1, gi:20378208. In certain embodiments of the compositions, methods and kits, a T7 Provider oligonucleotide is configured to comprise a target hybridizing sequence that is 21-32 nucleotides in length and that are complementary to a sequence in a region of *Campylobacter* nucleic acid corresponding to bases 83-150 of GenBank Accession No.: AF393202.1, gi:20378208, but has 1 mismatch; or 2 mismatches; or 3 mismatches; or 5 mismatches as compared to the portion of GenBank Accession No.: AF393202.1, gi:20378208 to which it is complementary. The T7 Provider oligonucleotide of these certain embodiments further comprises a promoter nucleotide sequence selected from the group consisting of; a transcriptional promoter recognized by an RNA Polymerase, a transcriptional promoter recognized by a bacteriophage T7 RNA polymerase, SEQ ID NO:75 and SEQ ID NO:76.

In certain embodiments of the compositions, kits and methods, a primer oligonucleotide is configured to comprise a target hybridizing sequence that is 19-35 nucleotides in length and that is at least 70%; or 75%; or 80%; or 85%; or 90% or 100% identical to a sequence in a region of *Campylobacter* nucleic acid corresponding to bases from about 170-226 of GenBank Accession No.: AF393202.1, gi:20378208. In certain embodiments, a primer oligonucleotide is configured to comprise a target hybridizing sequence that is 19-35 nucleotides in length and that is identical to a sequence in a region of *Campylobacter* nucleic acid corresponding to bases from about 170-226 of GenBank Accession No.: AF393202.1, gi:20378208 but has 1 mismatch; or 2 mismatches; or 3 mismatches; or 5 mismatches as compared to the portion of GenBank Accession No.: AF393202.1, gi:20378208 to which it is complementary.

In one embodiment, one or more additional oligonucleotide types and/or other amplification reagents that serve to facilitate or improve one or more aspects of the amplification reaction may be included. For example, in addition to a T7 Provider and/or a primer oligonucleotide, additional oligonucleotides may further include one or more of: a detection oligonucleotide, a blocker oligonucleotide, a target capture oligonucleotide, and the like.

In one embodiment, the compositions, kits, and/or methods may further include or use a detection oligonucleotide, preferably a linear or hairpin detection oligonucleotide, more preferably a torch oligonucleotide or molecular beacon oligonucleotide. In one aspect, the detection oligonucleotide stably hybridizes to an amplification product generated from a *Campylobacter* target nucleic acid using at least one amplification oligomer described herein, and more preferably using two amplification oligomers described herein. In one aspect, the detection oligonucleotide stably hybridizes to amplification products generated from a *C. jejuni* target nucleic acid and a *C. coli*, a *C. lari* or a *C. coli* and a *C. lari* target nucleic acid using at least one amplification oligomer described herein, and more preferably using two amplification oligomers described herein. In one aspect, the detection oligonucleotide is from 10 to 70 nucleotides in length and stably hybridizes to the "+" or "−" strand of a region of SEQ ID NO:91, or RNA equivalent thereof. In one aspect, the detection oligonucleotide is a torch oligonucleotide selected from the sequences of SEQ ID NOS:59-70 and their complements. In one aspect, the detection oligonucleotide is a torch oligonucleotide selected from the sequences of SEQ ID NOS: 62, 63, 65, 66, 67, and 68, and their complements. In one aspect, the detection oligonucleotide is a torch oligonucleotide selected from the sequences of SEQ ID NO:68, SEQ ID NO:67, and their complements. In one aspect, the detection oligonucleotide is a torch oligonucleotide having the sequence of SEQ ID NO:67 or its complement.

In one embodiment, the compositions, kits, and/or methods may further include or use a blocker oligonucleotide. In one aspect, the blocker oligonucleotide is selected from the sequences of SEQ ID NOS:50-57 and their complements. In one aspect, the blocker oligonucleotide is selected from the sequences of SEQ ID NOS:50, 53 and 56, and their complements. In one aspect, the blocker oligonucleotide has the sequence of SEQ ID NOs:50 or its complement.

In one embodiment, the compositions, kits, and/or methods might further include or use a target capture oligonucleotide. In one aspect, the target capture oligonucleotide is selected from the sequences of SEQ ID NOS: 71, 73, and their complements. In one aspect, the target capture oligonucleotide has the sequence of SEQ ID NOs:73 or its complement.

In some aspects, the compositions are used in a transcription-mediated amplification assay (hereinafter "TMA"). In some aspects, there are provided kits for performing a transcription-mediated amplification assay. In some aspects, there are provided methods for performing a transcription mediated amplification assay. In certain embodiments, the compositions, kits, and/or methods may include or use one or more oligonucleotides such as a: T7 Provider, primer oligonucleotide, detection oligonucleotide, blocker oligonucleotide, Torch oligonucleotide, and the like.

BRIEF DESCRIPTION OF THE DRAWINGS

FIG. 1 shows nucleotide residues 1-450 from the 16S rRNA nucleotide sequence of *Campylobacter jejuni* GenBank Accession Number AF393202.1, GI:20378208 (May 1, 2002).

FIG. 2 shows the nucleotide sequence of the 16S rRNA nucleotide sequence of *Campylobacter jejuni* GenBank Accession Number AF393202.1, GI:20378208 (May 1, 2002), which is also SEQ ID NO:91.

DETAILED DESCRIPTION

Disclosed are compositions, kits and methods for amplifying and detecting one or more of *C. jejuni, C. lari*, or *C. coli* target nucleic acid present in a sample. These target nucleic acids are 16S rRNA and/or genes encoding 16S rRNA from one or more of *C. jejuni, C. lari*, or *C. coli*. Preferably, the samples are food samples, water samples, industrial samples, environmental samples or biological samples. The compositions, kits and methods provide oligonucleotide sequences that specifically recognize these target nucleic acids. Such oligonucleotides may be used as amplification oligonucleotides, which may include primers, promoter primers, blocked oligonucleotides, and promoter provider oligonucleotides, whose functions have been described previously (e.g., U.S. Pat. Nos. 4,683,195; 4,683,202; 4,800,159; 5,399,491; 5,554,516; 5,824,518; and 7,374,885). Other oligonucleotides may be used as probes for detecting amplified sequences of *C. jejuni, C. lari*, and/or *C. coli*.

The amplification step includes contacting the sample with one or more amplification oligonucleotides specific for a target sequence within the target nucleic acid. Amplification synthesizes additional copies of the target sequence or its complement by using at least one nucleic acid polymerase. Depending on the amplification method used and the configuration of the amplification oligomer, amplification synthesizes a complementary DNA or RNA sequence corresponding to the target sequence or its complement. Ordinarily skilled artisans understand the amplification process employed in the various amplification techniques, and understand that the amplification product strands are sense or antisense to the template strand and may be RNA or DNA strands. One embodiment for detecting the amplified product uses a hybridizing step that includes contacting the amplified product with at least one probe specific for a portion of the amplification product. Some other detection methods include, gel electrophoresis, dye staining, radiolabeling and mass spectrometry, to name a few.

A detecting step may be performed after the amplification reaction is completed, or may be performed simultaneous with amplifying the target region, e.g., in real time. In one embodiment, the detection step allows homogeneous detection, e.g., detection of the hybridized probe without removal of unhybridized probe from the mixture (e.g., U.S. Pat. Nos. 5,639,604 and 5,283,174). In embodiments that detect the amplified product near or at the end of the amplification step, a linear probe may be used to provide a signal to indicate hybridization of the probe to the amplified product. In other embodiments that use real-time detection, the probe may be a linear probe, such as a dual labeled TaqMan probe detected upon 5'→3' exonuclease degradation of the probe, or may be a hairpin probe, such as a molecular beacon, molecular torch, or hybridization switch probe labeled with a reporter moiety that is detected when the hairpin probe binds to amplified product. Various forms of such probes have been described previously (e.g., U.S. Pat. Nos. 5,118,801; 5,210,015; 5,312,728; 5,538,848; 5,925,517; 6,150,097; 6,849,412; 6,835,542; 6,534,274; and 6,361,945; and US Pub. Nos. 20060068417A1; and US Pub. No. 20060194240A1).

To aid in understanding aspects of the disclosure, some terms used herein are described in more detail. All other scientific and technical terms used herein have the same meaning as commonly understood by those skilled in the relevant art, such as may be provided in *Dictionary of Microbiology and Molecular Biology*, 2nd ed. (Singleton et al., 1994, John Wiley & Sons, New York, N.Y.), *The Harper Collins Dictionary of Biology* (Hale & Marham, 1991, Harper Perennial, New York, N.Y.), and references cited herein. Unless mentioned otherwise, the techniques employed or contemplated herein are standard methods well known to a person of ordinary skill in the art of molecular biology.

It is to be noted that the term "a" or "an" entity refers to one or more of that entity; for example, "a nucleic acid," is understood to represent one or more nucleic acids. As such, the terms "a" (or "an"), "one or more," and "at least one" can be used interchangeably herein.

"Sample" includes any specimen that may contain *C. jejuni, C. lari*, and/or *C. coli* or components thereof, such as nucleic acids or fragments of nucleic acids. Samples may be obtained from environmental or manufacturing sources, e.g., food, water, soil, slurries, debris, biofilms from containers of aqueous fluids, airborne particles or aerosols, and the like, which may include processed samples, such as obtained from passing samples over or through a filtering device, or following centrifugation, or by adherence to a medium, matrix, or support. Samples include "biological samples" which include any tissue or material derived from a living or dead mammal or organism, including, e.g., respiratory tissue or exudates such as bronchoscopy, bronchoalveolar lavage, lung biopsy, sputum, milk, peripheral blood, plasma, serum, lymph node, gastrointestinal tissue, feces, urine, or other body fluids or materials. A sample may be treated to physically or mechanically disrupt tissue aggregates or cells, thus releasing intracellular components, including target nucleic acids, into a solution which may contain other components, such as enzymes, buffers, salts, detergents and the like.

"Nucleic acid" refers to a multimeric compound comprising two or more covalently bonded nucleosides or nucleoside analogs having nitrogenous heterocyclic bases, or base analogs, where the nucleosides are linked together by phosphodiester bonds or other linkages to form a polynucleotide. Nucleic acids include RNA, DNA, or chimeric DNA-RNA polymers or oligonucleotides, and analogs thereof. A nucleic acid "backbone" may be made up of a variety of linkages, including one or more of sugar-phosphodiester linkages, peptide-nucleic acid bonds (in "peptide nucleic acids" or PNAs, see PCT No. WO 95/32305), phosphorothioate linkages, methylphosphonate linkages, or combinations thereof. Sugar moieties of the nucleic acid may be either ribose or deoxyribose, or similar compounds having known substitutions, e.g., 2' methoxy substitutions and 2' halide substitutions (e.g., 2'-F). Nitrogenous bases may be conventional bases (A, G, C, T, U), analogs thereof (e.g., inosine, 5-methylisocytosine, isoguanine; *The Biochemistry of the Nucleic Acids* 5-36, Adams et al., ed., 11$^{th}$ ed., 1992, Abraham et al., 2007, Bio-Techniques 43: 617-24), which include derivatives of purine or pyrimidine bases (e.g., N$^4$-methyl deoxygaunosine, deaza- or aza-purines, deaza- or aza-pyrimidines, pyrimidine bases having substituent groups at the 5 or 6 position, purine bases having an altered or replacement substituent at the 2, 6 and/or 8 position, such as 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines, and pyrazolo-compounds, such as unsubstituted or 3-substituted pyrazolo[3,4-d]pyrimidine; U.S. Pat. Nos. 5,378,825, 6,949, 367 and PCT No. WO 93/13121). Nucleic acids may include "abasic" residues in which the backbone does not include a nitrogenous base for one or more residues (U.S. Pat. No. 5,585,481). A nucleic acid may comprise only conventional sugars, bases, and linkages as found in RNA and DNA, or may include conventional components and substitutions (e.g., conventional bases linked by a 2' methoxy backbone, or a nucleic acid including a mixture of conventional bases and one or more base analogs). Nucleic acids may include "locked nucleic acids" (LNA), in which one or more nucleotide monomers have a bicyclic furanose unit locked in an RNA mimicking sugar conformation, which enhances hybridization affinity toward complementary sequences in single-stranded RNA (ssRNA), single-stranded DNA (ssDNA), or double-stranded DNA (dsDNA) (Vester et al., 2004, *Biochemistry* 43(42):13233-41). Nucleic acids may include modified bases to alter the function or behavior of the nucleic acid, e.g., addition of a 3'-terminal dideoxynucleotide to block additional nucleotides from being added to the nucleic acid. Synthetic methods for making nucleic acids in vitro are well known in the art although nucleic acids may be purified from natural sources using routine techniques.

The term "polynucleotide" as used herein denotes a nucleic acid chain. Throughout this application, nucleic acids are designated by the 5'-terminus to the 3'-terminus. Standard nucleic acids, e.g., DNA and RNA, are typically synthesized "3'-to-5'," i.e., by the addition of nucleotides to the 5'-terminus of a growing nucleic acid.

A "nucleotide" as used herein is a subunit of a nucleic acid consisting of a phosphate group, a 5-carbon sugar and a nitrogenous base. The 5-carbon sugar found in RNA is ribose. In DNA, the 5-carbon sugar is 2'-deoxyribose. The term also includes analogs of such subunits, such as a methoxy group at the 2' position of the ribose (2'-O-Me, or 2' methoxy). As used herein, methoxy oligonucleotides containing "T" residues have a methoxy group at the 2' position of the ribose moiety, and a uracil at the base position of the nucleotide.

A "non-nucleotide unit" as used herein is a unit that does not significantly participate in hybridization of a polymer. Such units must not, for example, participate in any significant hydrogen bonding with a nucleotide, and would exclude units having as a component one of the five nucleotide bases or analogs thereof.

A "target nucleic acid" as used herein is a nucleic acid comprising a "target sequence" to be amplified. Target nucleic acids may be DNA or RNA and may be either single-stranded or double-stranded. The target nucleic acid may include other sequences besides the target sequence that may not be amplified. Typical target nucleic acids include virus genomes, bacterial genomes, fungal genomes, plant genomes, animal genomes, rRNA, tRNA, or mRNA from viruses, bacteria or eukaryotic cells, mitochondrial DNA, or chromosomal DNA. In the instant disclosure, target nucleic acids are 16S rRNA or genes encoding 16S rRNA from one or more of *C. jejuni, C. lari*, or *C. coli*.

By "isolated" it is meant that a target nucleic acid is taken from its natural milieu, but the term does not connote any degree of purification.

The term "target sequence" as used herein refers to the particular nucleotide sequence of the target nucleic acid that is to be amplified. Where the target nucleic acid is originally single-stranded, the term "target sequence" will also refer to the sequence complementary to the target sequence as present in the target nucleic acid. Where the target nucleic acid is originally double-stranded, the term "target sequence" refers to both the sense (+) and antisense (−) strands. In choosing a target sequence, the skilled artisan will understand that a sequence should be chosen so as to distinguish between unrelated or closely related target nucleic acids.

The term "target a sequence," "target(s) a target nucleic acid" or "targets a sequence" as used herein in reference to a region of *Campylobacter* nucleic acid refers to a process whereby an oligonucleotide stably hybridizes to the target sequence in a manner that allows for amplification and/or detection as described herein. In one embodiment, the oligonucleotide is complementary with the targeted *Campylobacter* nucleic acid sequence and contains no mismatches. In another embodiment, the oligonucleotide is complementary but contains 1; or 2; or 3; or 4; or 5 mismatches with the targeted *Campylobacter* nucleic acid sequence. Preferably, the oligonucleotide that stably hybridizes to the *Campylobacter* nucleic acid sequence includes at least 10 to as many as 50 nucleotides complementary to the target sequence. It is understood that at least 10 and as many as 50 is an inclusive range such that 10, 50 and each whole number there between are included. The term "configured to target a sequence" as used herein means that the target hybridizing region of an amplification oligonucleotide is designed to have a polynucleotide sequence that could target a sequence of the referenced *Campylobacter* region. Such an amplification oligonucleotide is not limited to targeting that sequence only, but is rather useful as a composition, in a kit or in a method for targeting a *C. jejuni* target nucleic acid and a *C. coli*, a *C. lari* or a *C. coli* and a *C. lari* target nucleic acid, as is described herein. The term "configured to" denotes an actual arrangement of the polynucleotide sequence configuration of the amplification oligonucleotide target hybridizing sequence.

The term "fragment" as used herein in reference to the *Campylobacter* targeted nucleic acid sequence refers to a piece of contiguous nucleic acid. In certain embodiments, the fragment includes contiguous nucleotides from a *Campylobacter* species' target nucleic acid, wherein the number of contiguous nucleotides in the fragment are less than that for the entire 16S rRNA or its encoding gene.

The term "region" as used herein refers to a portion of a nucleic acid wherein said portion is smaller than the entire nucleic acid. For example, when the nucleic acid in reference is an oligonucleotide promoter provider, the term "region" may be used refer to the smaller promoter portion of the entire oligonucleotide. Similarly, and also as example only, when the nucleic acid is a target nucleic acid, the term "region" may be used to refer to a smaller area of the nucleic acid.

The interchangeable terms "oligomer," "oligo" and "oligonucleotide" refer to a nucleic acid having generally less than 1,000 nucleotide (nt) residues, including polymers in a range having a lower limit of about 5 nt residues and an upper limit of about 500 to 900 nt residues. In some embodiments, oligonucleotides are in a size range having a lower limit of about 12 to 15 nt and an upper limit of about 50 to 600 nt, and other embodiments are in a range having a lower limit of about 15 to 20 nt and an upper limit of about 22 to 100 nt. Oligonucleotides may be purified from naturally occurring sources, but or may be synthesized using any of a variety of well known enzymatic or chemical methods. The term oligonucleotide does not denote any particular function to the reagent; rather, it is used generically to cover all such reagents described herein. An oligonucleotide may serve various different functions. For example, it may function as a primer if it is specific for and capable of hybridizing to a complementary strand and can further be extended in the presence of a nucleic acid polymerase, it may provide a promoter if it contains a sequence recognized by an RNA polymerase and allows for transcription (e.g., a T7 Provider), and it may function to prevent hybridization or impede primer extension if appropriately situated and/or modified.

As used herein, an oligonucleotide having a nucleic acid sequence "comprising" or "consisting of" or "consisting essentially of" a sequence selected from a group of specific sequences means that the oligonucleotide, as a basic and novel characteristic, is capable of stably hybridizing to a nucleic acid having the exact complement of one of the listed nucleic acid sequences of the group under stringent hybridization conditions. An exact complement includes the corresponding DNA or RNA sequence.

As used herein, a nucleic acid "corresponds" to a specified nucleic acid if the nucleic acid is 100% identical or complementary to the specified nucleic acid. As used herein, a nucleic acid "substantially corresponding to" a specified nucleic acid sequence means that the referred to oligonucleotide is sufficiently similar to the reference nucleic acid sequence such that the oligonucleotide has similar hybridization properties to the reference nucleic acid sequence in that it would hybridize with the same target nucleic acid sequence under stringent hybridization conditions. Substantially corresponding nucleic acids vary by at least one nucleotide from the specified nucleic acid. This variation may be stated in terms of a percentage of identical or complementary between the nucleic acid and the specified nucleic acid. Thus, nucleic acid substantially corresponds to a reference nucleic acid sequence if these percentages of base identity or complementarity are from less than 100% to about 80%. In preferred embodiments, the percentage is from less than 100% to about 85%. In more preferred embodiments, this percentage can be from less than 100% to about 90%; in other preferred embodiments, this percentage is from less than 100% to about 95%. One skilled in the art will understand that the recited ranges include all whole and rational numbers of the range (e.g., 92% or 98.377%).

A "helper oligonucleotide" or "helper" refers to an oligonucleotide designed to bind to a target nucleic acid and impose a different secondary and/or tertiary structure on the target to increase the rate and extent of hybridization of a detection probe or other oligonucleotide with the targeted nucleic acid, as described, for example, in U.S. Pat. No. 5,030,557. Helpers may also be used to assist with the hybridization to target nucleic acid sequences and function of primer, target capture and other oligonucleotides.

As used herein, a "blocking moiety" is a substance used to "block" the 3'-terminus of an oligonucleotide or other nucleic acid so that it cannot be efficiently extended by a nucleic acid polymerase.

An "amplification oligomer" is an oligomer, at least the 3'-end of which is complementary to a target nucleic acid ("target hybridizing sequence"), and which hybridizes to a target nucleic acid, or its complement, and participates in a nucleic acid amplification reaction. An example of an amplification oligomer is a "primer" that hybridizes to a target nucleic acid and contains a 3' OH end that is extended by a polymerase in an amplification process. Another example of an amplification oligomer is a "promoter-based amplification oligomer," which comprises a target hybridizing sequence, and a promoter sequence for initiating transcription by an appropriate polymerase. Promoter-based amplification oligomers may or may not be extended by a polymerase in a primer-based extension depending upon whether or not the 3' end of the target hybridizing sequence is modified to prevent primer-based extension (e.g., a 3' blocked end). A promoter-based amplification oligonucleotide comprising a target hybridizing region that is not modified to prevent primer-based extension is referred to as a "promoter-primer." A promoter-based amplification oligonucleotide comprising a target hybridizing region that is modified to prevent primer-based extension is referred to as a "promoter-provider." Size ranges for amplification oligonucleotides include those comprising target hybridizing regions that are about 10 to about 70 nt long. Included in this range are all whole numbers of the range, as is understood by a skilled artisan (e.g., 10, 11, 12, 13 . . . 67, 68, 69 and 70). An amplification oligomer may optionally include modified nucleotides or analogs that are not complementary to target nucleic acid in a strict A:T/U, G:C sense. Such modified nucleotides or analogs are herein considered mismatched to their corresponding target sequence.

Oligomers not intended for primer-based extension by a nucleic acid polymerase may include a blocker group that replaces the 3'OH to prevent the enzyme-mediated extension of the oligomer in an amplification reaction. For example, blocked amplification oligomers and/or detection probes present during amplification may not have functional 3'OH and instead include one or more blocking groups located at or near the 3' end. In some embodiments a blocking group near the 3' end and may be within five residues of the 3' end and is sufficiently large to limit binding of a polymerase to the oligomer. In other embodiments a blocking group is covalently attached to the 3' terminus. Many different chemical groups may be used to block the 3' end, e.g., alkyl groups, non-nucleotide linkers, alkane-diol dideoxynucleotide residues, and cordycepin.

As used herein, a "promoter" is a specific nucleic acid sequence that is recognized by a DNA-dependent RNA polymerase ("transcriptase") as a signal to bind to the nucleic acid and begin the transcription of RNA at a specific site.

As used herein, a "promoter-provider" or "provider" refers to an oligonucleotide comprising first and second regions, and which is modified to prevent the initiation of DNA synthesis from its 3'-terminus. The "first region" of a promoter-provider oligonucleotide comprises a base sequence which hybridizes to a DNA template, where the hybridizing sequence is situated 3', but not necessarily adjacent to, a promoter region. The target-hybridizing portion of a promoter oligonucleotide is typically at least 10 nucleotides in length, and may extend up to 50 or more nucleotides in length. The "second region" comprises a promoter sequence for an RNA polymerase. A promoter-provider oligonucleotide is configured so that it is incapable of being extended by an RNA- or DNA-dependent DNA polymerase, (e.g., reverse transcriptase), preferably by comprising a blocking moiety at its 3'-terminus as described above. This modification differentiates promoter providers from promoter primers. Preferably, the promoter portion of a promoter primer or provider is a promoter for a DNA-dependent RNA polymerase from *E. coli* and bacteriophages T7, T3, and SP6, though other promoters or modified version thereof can be used as well.

As used herein, a "terminating oligonucleotide" or "blocker oligonucleotide" is an oligonucleotide comprising a base sequence that is complementary to a region of the target nucleic acid in the vicinity of the 5'-end of the target sequence, so as to "terminate" primer extension of a nascent nucleic acid that includes a priming oligonucleotide, thereby providing a defined 3'-end for the nascent nucleic acid strand.

"Amplification" refers to any known procedure for obtaining multiple copies of a target nucleic acid sequence or its complement or fragments thereof. The multiple copies may be referred to as amplicons or amplification products. Amplification of "fragments" refers to production of an amplified nucleic acid that contains less than the complete target nucleic acid or its complement, e.g., produced by using an amplification oligonucleotide that hybridizes to, and initiates polymerization from, an internal position of the target nucleic acid. Known amplification methods include, for example, replicase-mediated amplification, polymerase chain reaction (PCR), ligase chain reaction (LCR), strand-displacement amplification (SDA), and transcription-mediated or transcription-associated amplification. Replicase-mediated amplification uses self-replicating RNA molecules, and a replicase such as QB-replicase (e.g., U.S. Pat. No. 4,786,600). PCR amplification uses a DNA polymerase, pairs of primers, and thermal cycling to synthesize multiple copies of two complementary strands of dsDNA or from a cDNA (e.g., U.S. Pat. Nos. 4,683,195, 4,683,202, and 4,800,159). LCR amplification uses four or more different oligonucleotides to amplify a target and its complementary strand by using multiple cycles of hybridization, ligation, and denaturation (e.g., U.S. Pat. No. 5,427,930 and U.S. Pat. No. 5,516,663). SDA uses a primer that contains a recognition site for a restriction endonuclease and an endonuclease that nicks one strand of a hemimodified DNA duplex that includes the target sequence, whereby amplification occurs in a series of primer extension and strand displacement steps (e.g., U.S. Pat. No. 5,422,252; U.S. Pat. No. 5,547,861; and U.S. Pat. No. 5,648,211).

"Transcription associated amplification" or "transcription mediated amplification" (TMA) refer to nucleic acid amplification that uses an RNA polymerase to produce multiple RNA transcripts from a nucleic acid template. These methods generally employ an RNA polymerase, a DNA polymerase, deoxyribonucleoside triphosphates, ribonucleoside triphosphates, and a template complementary oligonucleotide that includes a promoter sequence, and optionally may include one or more other oligonucleotides. TMA methods are embodiments of amplification methods used for amplifying and detecting *C. jejuni, C. lari,* or *C. coli* target sequences as described herein. Variations of transcription associated amplification are well known in the art as previously disclosed in detail (e.g., U.S. Pat. Nos. 4,868,105; 5,124,246; 5,130,238; 5,399,491; 5,437,990; 5,554,516; and 7,374,885; and PCT Pub. Nos. WO 88/01302; WO 88/10315 and WO 95/03430). The person of ordinary skill in the art will appreciate that the disclosed compositions may be used in amplification methods based on extension of oligomer sequences by a polymerase.

As used herein, the term "real-time TMA" refers to single-primer transcription-mediated amplification ("TMA") of target nucleic acid that is monitored by real-time detection means.

The term "amplicon" or the term "amplification product" as used herein refers to the nucleic acid molecule generated during an amplification procedure that is complementary or homologous to a sequence contained within the target sequence. These terms can be used to refer to a single strand amplification product, a double strand amplification product or one of the strands of a double strand amplification product.

"Probe," "detection probe" or "detection oligonucleotide" are terms referring to a nucleic acid oligomer that hybridizes specifically to a target sequence in a nucleic acid, or in an amplified nucleic acid, under conditions that promote hybridization to allow detection of the target sequence or amplified nucleic acid. Detection may either be direct (e.g., a probe hybridized directly to its target sequence) or indirect (e.g., a probe linked to its target via an intermediate molecular structure). Probes may be DNA, RNA, analogs thereof or combinations thereof and they may be labeled or unlabeled. A probe's "target sequence" generally refers to a smaller nucleic acid sequence within a larger nucleic acid sequence that hybridizes specifically to at least a portion of a probe oligomer by standard base pairing. A probe may comprise target-specific sequences and other sequences that contribute to the three-dimensional conformation of the probe (e.g., U.S. Pat. Nos. 5,118,801; 5,312,728; 6,849,412; 6,835,542; 6,534,274; and 6,361,945; and US Pub. No. 20060068417).

By "stable" or "stable for detection" is meant that the temperature of a reaction mixture is at least 2° C. below the melting temperature of a nucleic acid duplex.

As used herein, a "label" refers to a moiety or compound joined directly or indirectly to a probe that is detected or leads to a detectable signal. Direct labeling can occur through bonds or interactions that link the label to the probe, including covalent bonds or non-covalent interactions, e.g. hydrogen bonds, hydrophobic and ionic interactions, or formation of chelates or coordination complexes. Indirect labeling can occur through use of a bridging moiety or "linker" such as a binding pair member, an antibody or additional oligomer, which is either directly or indirectly labeled, and which may amplify the detectable signal. Labels include any detectable moiety, such as a radionuclide, ligand (e.g., biotin, avidin), enzyme or enzyme substrate, reactive group, or chromophore (e.g., dye, particle, or bead that imparts detectable color), luminescent compound (e.g., bioluminescent, phosphorescent, or chemiluminescent labels), or fluorophore. Labels may be detectable in a homogeneous assay in which bound labeled probe in a mixture exhibits a detectable change different from that of an unbound labeled probe, e.g., instability or differential degradation properties. A "homogeneous detectable label" can be detected without physically removing bound from unbound forms of the label or labeled probe (e.g., U.S. Pat. Nos. 5,283,174, 5,656,207, and 5,658,737). Labels include chemiluminescent compounds, e.g., acridinium ester ("AE") compounds that include standard AE and derivatives (e.g., U.S. Pat. Nos. 5,656,207, 5,658,737, and 5,639,604). Synthesis and methods of attaching labels to nucleic acids and detecting labels are well known (e.g., Sambrook et al., *Molecular Cloning, A Laboratory Manual,* 2nd ed. (Cold Spring Harbor Laboratory Press, Cold Spring Harbor, N.Y., 1989), Chapter 10; U.S. Pat. Nos. 5,658,737, 5,656, 207, 5,547,842, 5,283,174, and 4,581,333). More than one label, and more than one type of label, may be present on a particular probe, or detection may use a mixture of probes in which each probe is labeled with a compound that produces a detectable signal (e.g., U.S. Pat. Nos. 6,180,340 and 6,350, 579).

As used herein, structures referred to as "molecular torches" are designed to include distinct regions of self-complementarity ("the closing domain") which are connected by a joining region ("the target binding domain") and which hybridize to one another under predetermined hybridization assay conditions. All or part of the nucleotide sequences comprising target closing domains may also function as target binding domains. Thus, target closing sequences can include, target binding sequences, non-target binding sequences, and combinations thereof.

As used herein, a "capture oligonucleotide" or "capture probe" refers to a nucleic acid oligomer that specifically hybridizes to a target sequence in a target nucleic acid by standard base pairing and joins to a binding partner on an immobilized probe to capture the target nucleic acid to a support. One example of a capture oligomer includes an oligonucleotide comprising two binding regions: a target hybridizing sequence and an immobilized probe-binding region. A variation of this example, the two regions may be present on two different oligomers joined together by one or more linkers. Another embodiment of a capture oligomer the target hybridizing sequence is a sequence that includes random or non-random poly-GU, poly-GT, or poly U sequences to bind non-specifically to a target nucleic acid and link it to an immobilized probe on a support. (PCT Pub No. WO 2008/016988). The immobilized probe binding region can be a nucleic acid sequence, referred to as a tail. Tails include a substantially homopolymeric tail of about 10 to 40 nucleotides (e.g., $A_{10}$ to $A_{40}$), or of about 14 to 33 nt (e.g., $T_3A_{14}$ to $T_3A_{30}$), that bind to a complementary immobilized sequence attached to the support particle or support matrix. Another example of a of a capture oligomer comprises two regions, a target hybridizing sequence and a binding pair member that is not a nucleic acid sequence.

As used herein, an "immobilized oligonucleotide", "immobilized probe" or "immobilized nucleic acid" refers to a nucleic acid binding partner that joins a capture oligomer to a support, directly or indirectly. An immobilized probe joined to a support facilitates separation of a capture probe bound target from unbound material in a sample. One embodiment of an immobilized probe is an oligomer joined to a support that facilitates separation of bound target sequence from unbound material in a sample. Supports may include known materials, such as matrices and particles free in solution, which may be made of nitrocellulose, nylon, glass, polyacrylate, mixed polymers, polystyrene, silane, polypropylene, metal, or other compositions, of which one embodiment is magnetically attractable particles. Supports may be monodisperse magnetic spheres (e.g., uniform size ±5%), to which an immobilized probe is joined directly (via covalent linkage, chelation, or ionic interaction), or indirectly (via one or more linkers), where the linkage or interaction between the probe and support is stable during hybridization conditions.

By "complementary" is meant that the nucleotide sequences of similar regions of two single-stranded nucleic acids, or to different regions of the same single-stranded nucleic acid have a nucleotide base composition that allow the single-stranded regions to hybridize together in a stable double-stranded hydrogen-bonded region under stringent hybridization or amplification conditions. Sequences that hybridize to each other may be completely complementary or partially complementary to the intended target sequence by standard nucleic acid base pairing (e.g. G:C, A:T or A:U pairing). By "sufficiently complementary" is meant a contiguous sequence that is capable of hybridizing to another sequence by hydrogen bonding between a series of complementary bases, which may be complementary at each position in the sequence by standard base pairing or may contain one or more residues that are not complementary by standard A:T/U and G:C pairing, or are modified nucleotides such as abasic residues, modified nucleotides or nucleotide analogs. Sufficiently complementary contiguous sequences typically are at least 80%, or at least 90%, complementary to a sequence to which an oligomer is intended to specifically hybridize (a %-complementarity range includes all whole and rational numbers of the range). Sequences that are "sufficiently complementary" allow stable hybridization of a nucleic acid oligomer with its target sequence under appropriate hybridization conditions, even if the sequences are not completely complementary. When a contiguous sequence of nucleotides of one single-stranded region is able to form a series of "canonical" hydrogen-bonded base pairs with an analogous sequence of nucleotides of the other single-stranded region, such that A is paired with U or T and C is paired with G, the nucleotides sequences are "completely" complementary.

By "preferentially hybridize" is meant that under stringent hybridization assay conditions, an oligonucleotide hybridizes to its target sequences, or replicates thereof, to form stable oligonucleotide: target sequence hybrid, while at the same time formation of stable oligonucleotide: non-target sequence hybrid is minimized. For example, a probe oligonucleotide preferentially hybridizes to a target sequence or replicate thereof to a sufficiently greater extent than to a non-target sequence, to enable one having ordinary skill in the art to accurately detect the RNA replicates or complementary DNA (cDNA) of the target sequence formed during the amplification. Appropriate hybridization conditions are well known in the art for probe, amplification, target capture, blocker and other oligonucleotides, may be predicted based on sequence composition, or can be determined by using routine testing methods (e.g., Sambrook et al., *Molecular Cloning, A Laboratory Manual*, $2^{nd}$ ed. (Cold Spring Harbor Laboratory Press, Cold Spring Harbor, N.Y., 1989) at §§1.90-1.91, 7.37-7.57, 9.47-9.51 and 11.47-11.57, particularly §§9.50-9.51, 11.12-11.13, 11.45-11.47 and 11.55-11.57).

By "nucleic acid hybrid" or "hybrid" or "duplex" is meant a nucleic acid structure containing a double-stranded, hydrogen-bonded region wherein each strand is complementary to the other, and wherein the region is sufficiently stable under stringent hybridization conditions to be detected by means including, but not limited to, chemiluminescent or fluorescent light detection, autoradiography, or gel electrophoresis. Such hybrids may comprise RNA:RNA, RNA:DNA, or DNA:DNA duplex molecules.

"Sample preparation" refers to any steps or methods that treat a sample for subsequent amplification and/or detection of *C. jejuni*, *C. lari*, or *C. coli* nucleic acids present in the sample. Samples may be complex mixtures of components of which the target nucleic acid is a minority component. Sample preparation may include any known method of concentrating components, such as microbes or nucleic acids, from a larger sample volume, such as by filtration of airborne or waterborne particles from a larger volume sample or by isolation of microbes from a sample by using standard microbiology methods. Sample preparation may include physical disruption and/or chemical lysis of cellular components to release intracellular components into a substantially aqueous or organic phase and removal of debris, such as by using filtration, centrifugation or adsorption. Sample preparation may include use of nucleic acid oligonucleotide that selectively or non-specifically capture a target nucleic acid and separate it from other sample components (e.g., as described in U.S. Pat. No. 6,110,678 and PCT Pub. No. WO 2008/016988).

"Separating" or "purifying" means that one or more components of a sample are removed or separated from other sample components. Sample components include target nucleic acids usually in a generally aqueous solution phase, which may also include cellular fragments, proteins, carbohydrates, lipids, and other nucleic acids. Separating or purifying removes at least 70%, or at least 80%, or at least 95% of the target nucleic acid from other sample components. Ranges of %-purity include all whole and rational numbers of the range.

As used herein, a "DNA-dependent DNA polymerase" is an enzyme that synthesizes a complementary DNA copy from a DNA template. Examples are DNA polymerase I from *E. coli*, bacteriophage T7 DNA polymerase, or DNA polymerases from bacteriophages T4, Phi-29, M2, or T5. DNA-dependent DNA polymerases may be the naturally occurring enzymes isolated from bacteria or bacteriophages or expressed recombinantly, or may be modified or "evolved" forms which have been engineered to possess certain desirable characteristics, e.g., thermostability, or the ability to recognize or synthesize a DNA strand from various modified templates. All known DNA-dependent DNA polymerases require a complementary primer to initiate synthesis. It is known that under suitable conditions a DNA-dependent DNA polymerase may synthesize a complementary DNA copy from an RNA template. RNA-dependent DNA polymerases typically also have DNA-dependent DNA polymerase activity.

As used herein, a "DNA-dependent RNA polymerase" or "transcriptase" is an enzyme that synthesizes multiple RNA copies from a double-stranded or partially double-stranded DNA molecule having a promoter sequence that is usually double-stranded. The RNA molecules ("transcripts") are synthesized in the 5'-to-3' direction beginning at a specific position just downstream of the promoter. Examples of transcriptases are the DNA-dependent RNA polymerase from *E. coli* and bacteriophages T1, T3, and SP6.

As used herein, an "RNA-dependent DNA polymerase" or "reverse transcriptase" ("RT") is an enzyme that synthesizes a complementary DNA copy from an RNA template. All known reverse transcriptases also have the ability to make a complementary DNA copy from a DNA template; thus, they are both RNA- and DNA-dependent DNA polymerases. RTs may also have an RNAse H activity. A primer is required to initiate synthesis with both RNA and DNA templates.

As used herein, a "selective RNAse" is an enzyme that degrades the RNA portion of an RNA:DNA duplex but not single-stranded RNA, double-stranded RNA or DNA. An exemplary selective RNAse is RNAse H. Enzymes possessing the same or similar activity as RNAse H may also be used. Selective RNAses may be endonucleases or exonucleases. Most reverse transcriptase enzymes contain an RNAse H activity in addition to their polymerase activities. However, other sources of the RNAse H are available without an associated polymerase activity. The degradation may result in separation of RNA from a RNA:DNA complex. Alternatively, a selective RNAse may simply cut the RNA at various locations such that portions of the RNA melt off or permit enzymes to unwind portions of the RNA. Other enzymes that selectively degrade RNA target sequences or RNA products of the present invention will be readily apparent to those of ordinary skill in the art.

The term "specificity," in the context of an amplification system, is used herein to refer to the characteristic of an amplification system which describes its ability to distinguish between target and non-target sequences dependent on sequence and assay conditions. In terms of nucleic acid amplification, specificity generally refers to the ratio of the number of specific amplicons produced to the number of side-products (e.g., the signal-to-noise ratio).

The term "sensitivity" is used herein to refer to the precision with which a nucleic acid amplification reaction can be detected or quantitated. The sensitivity of an amplification reaction is generally a measure of the smallest copy number of the target nucleic acid that can be reliably detected in the amplification system, and will depend, for example, on the detection assay being employed, and the specificity of the amplification reaction, e.g., the ratio of specific amplicons to side-products.

As used herein, a "colony forming unit" ("CFU") is used as a measure of viable microorganisms in a sample. A CFU is an individual viable cell capable of forming on a solid medium a visible colony whose individual cells are derived by cell division from one parental cell. One CFU corresponds to ~1000 copies of rRNA.

As used herein, the term "TTime" is the threshold time or time of emergence of signal in a real-time plot of the assay data. TTime values estimate the time at which a particular threshold indicating amplicon production is passed in a real-time amplification reaction. TTime and an algorithm for calculating and using TTime values are described in U.S. Pub. No. 2006/0276972, paragraphs [0517] through [0538]. A curve fitting procedure is applied to normalized and background-adjusted data. The curve fit is performed for only a portion of the data between a predetermined low bound and high bound. The goal, after finding the curve that fits the data, is to estimate the time corresponding to the point at which the curve or a projection thereof intersects a predefined threshold value. In one embodiment, the threshold for normalized data is 0.11. The high and low bounds are determined empirically as that range over which curves fit to a variety of control data sets exhibit the least variability in the time associated with the given threshold value. For example, in one embodiment, the low bound is 0.04 and the high bound is 0.36. The curve is fit for data extending from the first data point below the low bound through the first data point past the high bound. Next, there is made a determination whether the slope of the fit is statistically significant. For example, if the p value of the first order coefficient is less than 0.05, the fit is considered significant, and processing continues. If not, processing stops. Alternatively, the validity of the data can be determined by the $R^2$ value. The slope m and intercept b of the linear curve y=mx+b are determined for the fitted curve. With that information, TTime can be determined as follows:

$$T\text{Time} = (\text{Threshold} - b)/m$$

As used herein, the term "relative fluorescence unit" ("RFU") is an arbitrary unit of measurement of fluorescence intensity. RFU varies with the characteristics of the detection means used for the measurement.

Transcription Mediated Amplification and Real-Time Transcription Mediated Amplification.

Amplification methods that use TMA amplification include the following steps. Briefly, a single stranded target nucleic acid containing the target sequence to be amplified is provided. Those skilled in the art will appreciate that conventional melting of double stranded nucleic acid may be used to provide single-stranded target nucleic acids. A first amplification oligomer is brought in contact with that target nucleic acid by hybridizing to the target sequence. The first amplification oligomer may be a primer or a promoter primer. A suitable nucleic acid polymerase then generates a nucleic acid strand amplification product that is complementary to the target nucleic acid target sequence. In the instances where the target nucleic acid is an RNA, the RNA is typically degraded leaving just the newly generated amplification product, which is available for hybridization by a second amplification oligomer. Using a primer as the first amplification oligomer, then the second amplification oligomer is a promoter primer or promoter provider. A suitable nucleic acid polymerase uses the newly generated amplification product to which the promoter-based oligomer is hybridized as a primer to make a complementary strand of the unhybridized promoter sequence. If the second amplification oligomer is a promoter primer, then a complementary copy of the amplification product hybridized by the second amplification oligomer is also generated. The now double stranded promoter sequence of the promoter-based amplification is used by a suitable RNA polymerase to initiate transcription and make RNA transcript amplification products. The first amplification oligomer primer can then hybridize the transcribed amplification products and the steps can repeat. Or, the target nucleic acid is RNA and the first amplification oligomer is a promoter-based amplification oligomer. Here, the promoter based amplification oligomer is a promoter primer. A suitable polymerase makes a first amplification product that is complementary to the RNA target sequence. The RNA target nucleic acid is degraded and a second amplification oligomer is hybridized to the amplification product. A suitable polymerase makes a complement strand, thereby generating a double stranded promoter sequence. Transcription is initiated and RNA is transcribed. The transcribed RNA is complementary to the original target nucleic acid, thus the second amplification oligomer hybridizes again and makes the transcribed RNA double stranded. The RNA is degraded and the remaining DNA strand is hybridized by the first amplification oligomer. The amplification steps can repeat. When the target nucleic acid is DNA the first amplification oligomer is a promoter primer and the second amplification is a primer. Amplification generally proceeds as described above, and as is described in the art. See e.g., U.S. Pat. Nos. 4,868,105; 5,124, 246; 5,130,238; 5,399,491; 5,437,990; 5,554,516; and 7,374, 885; and PCT Pub. Nos. WO 88/01302; WO 88/10315 and WO 95/03430 describing TMA and other variations of transcription-associated amplification. The amplified products may be detected in real-time during amplification, or at the end of the amplification reaction. Detection may be performed by a number of methods. Probe-based detection methods use an oligonucleotide probe comprising a target hybridizing sequence that binds specifically to a target sequence contained in the amplification products. Detection of a signal resulting from the bound probes indicates the presence of the target nucleic acid in the sample.

Nucleic Acid Detection.

Detection of the nucleic acids may be accomplished by a variety of methods. Detection methods may use nucleic acid probes comprising a target hybridizing sequence that is complementary to a portion of the amplified product and detecting the presence of the probe:product complex, or by using a complex of probes that may amplify the detectable signal associated with the amplified products (e.g., U.S. Pat. Nos. 5,424,413; 5,451,503; and 5,849,481). Directly or indirectly labeled probes that specifically associate with the amplified product provide a detectable signal that indicates the presence of the target nucleic acid in the sample. For example, if the target nucleic acid is C. jejuni, C. lari, or C. coli 16S rRNA, the amplified product will contain a sequence in or complementary to a C. jejuni, C. lari, or C. coli target sequence. A probe is configured to bind directly or indirectly to a portion of the amplification product to indicate the presence of C. jejuni, C. lari, or C. coli in the tested sample.

Embodiments of probes that hybridize to the amplified sequences include hairpin oligonucleotides such as Molecular Torches and linear oligonucleotides that substantially do not form conformations held by intramolecular bonds. Preferably, said probes may include labels. Linear probe embodiments may include a chemiluminescent compound as the label, e.g. a chemiluminescent AE compound attached to the probe sequence via a linker (substantially as described in U.S. Pat. Nos. 5,585,481 and 5,639,604, particularly at column 10, line 6 to column 11, line 3, and in Example 8 therein). Examples of labeling positions are a central region of the probe oligomer and near a region of A:T base pairing, at a 3' or 5' terminus of the oligomer, and at or near a mismatch site with a known sequence that is not the desired target sequence. Hairpin or linear probes may be labeled with any of a variety of different types of interacting labels, where one interacting member is usually attached to the 5' end of the probe and the other interacting member is attached to the 3' end of the probe. Dye labeled probes, including dual labeled probes, single labeled probes, AE labeled probes and the like, are generally known. dual labeled probes can be labeled at one end with a fluorescent label ("F") that absorbs light of a particular wavelength or range and emits light another emission wavelength or range and at the other end with a quencher ("Q") that dampens, partially or completely, signal emitted from the excited F when Q is in proximity with the fluorophore. Such a probe may be referred to as labeled with a fluorescent/quencher (F/Q) pair. One embodiment of a hairpin probe is a "molecular torch" that detects an amplified product to indicate whether a target C. jejuni, C. lari, or C. coli sequence is present in the sample after the amplification step. A molecular torch probe comprises a target binding domain and a closing domain, as is described above. These domains allow the molecular torch to exist in open and closed conformations, depending on whether the torch is bound to a target. (See also, U.S. Pat. Nos. 6,849,412; 6,835,542; 6,534,274; and 6,361, 945). Another hairpin probe embodiment is a "molecular beacon" which is generally described in Tyagi et al., 1998, Nature Biotechnol. 16:49-53, and in U.S. Pat. Nos. 5,118, 801; and 5,312,728. Methods for using such hairpin probes to detect the presence of a target sequence are well known in the art.

A method for detecting C. jejuni, C. lari, or C. coli sequences uses a transcription associated amplification and a molecular torch. The molecular torch is added before or during amplification, allowing detection to be carried out without the addition of other reagents. For example, a molecular torch may be designed so that the Tm of the hybridized target binding region and closing region complex is higher than the amplification reaction temperature, thusly designed to prevent the probe from prematurely binding to amplified target sequences. After an interval of amplification, the mixture is heated to open the torch regions and allow the target binding regions to hybridize to a portion of the amplification products. The solution is then cooled to close any probes not bound to amplified products by allowing the probe target binding and closing regions to hybridize, which effectively closes the label/quencher pair. Detection is then performed to generate and detect signals from only the probes that are hybridized to the amplified target sequences. For example, the mixture containing the F/Q labeled hairpin probe is irradiated with the appropriate excitation light and the emission signal is measured. In other embodiments, the hairpin detection probe is designed so that the amplified products hybridize to the target binding region of the probe during amplification, resulting in changing the hairpin to its open conformation during amplification, and the amplification reaction mixture is irradiated at intervals to detect the emitted signal from the open probes in real time during amplification.

Sample Preparation.

Preparation of samples for amplification and detection of *C. jejuni, C. lari,* or *C. coli* sequences may include methods of separating and/or concentrating organisms contained in a sample from other sample components, e.g., filtration of particulate matter from air, water or other types of samples. Sample preparation may include routine methods of disrupting cells or lysing bacteria to release intracellular contents, including *C. jejuni, C. lari,* or *C. coli* 16S rRNA or genetic sequences encoding 16S rRNA. Sample preparation before amplification may include an optional step of target capture to specifically or non-specifically separate the target nucleic acids from other sample components. Nonspecific target capture methods may involve selective precipitation of nucleic acids from a substantially aqueous mixture, adherence of nucleic acids to a support that is washed to remove other sample components, other methods of physically separating nucleic acids from a mixture that contains *C. jejuni, C. lari,* or *C. coli* nucleic acid and other sample components.

In one embodiment, *C. jejuni, C. lari,* or *C. coli* target nucleic acids are selectively separated from other sample components by specifically hybridizing the *C. jejuni, C. lari,* or *C. coli* target nucleic acid to a capture oligomer specific for *C. jejuni, C. lari,* and/or *C. coli* to form a target sequence:capture probe complex. The complex is separated from sample components by binding the target:capture probe complex to an immobilized probe, and separating the target:capture probe:immobilized probe complex from the sample, as previously described (U.S. Pat. Nos. 6,110,678; 6,280,952; and 6,534,273). Target capture may occur in a solution phase mixture that contains one or more capture oligonucleotides that hybridize specifically to target nucleic acids under hybridizing conditions, usually at a temperature higher than the Tm of the tail sequence:immobilized probe sequence duplex. The target:capture probe complex is captured by adjusting the hybridization conditions so that the capture probe tail hybridizes to the immobilized probe, and the entire complex on the support is then separated from other sample components. The support with the attached immobilized probe:capture probe:target sequence may be washed one or more times to further remove other sample components. Other embodiments link the immobilized probe to a particulate support, such as a paramagnetic bead, so that particles with the attached target:capture probe:immobilized probe complex may be suspended in a washing solution and retrieved from the washing solution, by using magnetic attraction. To limit the number of handling steps, the target nucleic acid may be amplified by simply mixing the target sequence in the complex on the support with amplification oligonucleotides and proceeding with amplification steps.

Preferred *Campylobacter* Oligonucleotides for the Amplification and Detection of 16S rRNA Sequences of *C. jejuni, C. lari,* or *C. coli*.

As is described herein, preferred sites for selectively amplifying and detecting *Campylobacter jejuni, Campylobacter lari* and *Campylobacter coli* nucleic acids are disclosed. The preferred sites are selected to discriminate against amplification and/or detection of other *Campylobacter* species and other bacteria (herein referred to as "near neighbor organisms," "challenge organisms" or "exclusionaries"). These preferred sites are found within a region of the *Campylobacter* 16S rRNA. Particularly preferred oligonucleotides and oligonucleotide sets with these regions have been identified for amplifying *Campylobacter jejuni, Campylobacter lari* and *Campylobacter coli* 16S rRNA with improved sensitivity, selectivity and specificity.

Oligonucleotides were designed by first comparing 16S rRNA sequences (or gene sequences encoding 16S rRNA) of a number of *Campylobacter* species (e.g., *C. jejuni, C. lari, C. coli, C. fetus, C. upsaliensis, C. hyointestinalis, C. curvus, C. hominis, C. insulaenigrae, C. lanienae, C. mucosalis, C. rectus, C. sputorum,* and *C. concisus*) and a number of other bacterial species within the order of Campylobacterales (e.g., *Arcobacter, Helicobacter, Flexispira, Geospirillum, Sulfurospirillum, Sulfuricurvum,* and *Hydrogenimonas*). Oligonucleotides were synthesized in vitro, and in some embodiment oligomers can be characterized by determining the Tm and hybridization characteristics of the *C. jejuni, C. lari,* or *C. coli* oligomers with complementary target sequences (synthetic or purified rRNA from bacteria) using standard laboratory methods. Then, selected oligomer sequences were further tested against 16S rRNA sequences. This test used different combinations of amplification oligomers (selected from those shown in Table 1). The amplification reactions included 16S rRNA targets from lysates or purified from various *Campylobacter* species grown in culture. The amplification reaction determined the efficiency of amplification of the 16S rRNA target sequences using the various amplification oligo combinations. Amplification oligomers include those that may function as primer, promoter primer, and promoter provider oligomers. The relative efficiencies of different combinations of amplification oligomers were monitored by detecting the amplified products of the amplification reactions, generally by binding a labeled probe (Table 2) to the amplified products and detecting the relative amount of signal that indicated the amount of amplified product made.

Some examples of primers useful with the current invention include oligonucleotides that are from about 10 to about 70 nucleotides in length and comprise a nucleotide sequence that is designed to hybridize to either the "+" or the "−" strand of a region of SEQ ID NO:91, wherein the region of SEQ ID NO:91 is from about nucleotide 62 to about nucleotide 226; is from about nucleotide 170 to about nucleotide 226; is from about nucleotide 170 to about nucleotide 205 and the primer includes a sequence hybridizing to nucleotide 184 to nucleotide 194; is from about nucleotide 184 to about nucleotide 212 and the primer includes a sequence that targets nucleotide 192 to nucleotide 205; is from about nucleotide 170 to about nucleotide 212; or is from about nucleotide 170 to about nucleotide 226 and the primer includes sequence hybridizing to nucleotide 184 to nucleotide 194, a sequence hybridizing to nucleotide 192 to nucleotide 205 or both. (See, SEQ ID NOS: 77-83) Additions, deletions and mismatches may be incorporated into a primer oligo designed to hybridize to a region of SEQ ID NO:91. Representative primer oligo sequences are shown in Table 1 as SEQ ID NOS:1-17 (Primers).

Some embodiments of the target-specific sequence of a promoter primer/promoter provider oligomer are listed in Table 1, and these target-specific sequences may be attached to the 3' end of any known promoter sequence. The promoter sequences of a promoter primer/promoter provider will be shown in lower case in Table 1. An example of a promoter sequence specific for the RNA polymerase of bacteriophage T7 is SEQ ID NO:75 (5'-aatttaatacgactcactatagggaga). Other promoter sequences are also useful for promoter primer/promoter provider oligos. Some examples of promoter-based amplification oligomer target hybridizing sequences include oligonucleotides that are from about 10 to about 50 nucleotides in length and comprise a nucleotide sequence that is configured to hybridize to either the "+" or the "−" strand of a region of SEQ ID NO:91. One region of SEQ ID NO:91 is from about nucleotide 14 to about nucleotide 150. One region is from about nucleotide 14 to about nucleotide 41 of SEQ ID NO:91. One region is from about nucleotide 14 to about nucleotide 41 of SEQ ID NO:91 and the target hybridizing sequence contains a sequence identical or complementary to nucleotide 20 to nucleotide 37 of SEQ ID NO:91. One region of SEQ ID NO:91 is from about nucleotide 58 to about nucleotide 108. One region of SEQ ID NO:91 is from about nucleotide 108 to about nucleotide 150. One region of SEQ ID NO:91 is from about nucleotide 108 to about nucleotide 150 and the target hybridizing sequence contains a sequence identical or complementary to nucleotide 125 to nucleotide 135 of SEQ ID NO:91. One region of SEQ ID NO:91 is from about nucleotide 58 to about nucleotide 150. One region of SEQ ID NO:91 is from about nucleotide 112 to about nucleotide 138. One region of SEQ ID NO:91 is from about nucleotide 112 to about nucleotide 138 and the target hybridizing sequence contains a sequence identical or complementary to nucleotide 125 to nucleotide 135 of SEQ ID NO:91. One region of SEQ ID NO:91 is from about nucleotide 112 to about nucleotide 138 and the target hybridizing sequence contains a sequence identical or complementary to nucleotide 115 to nucleotide 135 of SEQ ID NO:91. One region of SEQ ID NO:91 is from about nucleotide 115 to about nucleotide 150. One region of SEQ ID NO:91 is from about nucleotide 115 to about nucleotide 150 and the target hybridizing sequence contains a sequence identical or complementary to nucleotide 125 to nucleotide 135 of SEQ ID NO:91. One region of SEQ ID NO:91 is from about nucleotide 125 to about nucleotide 150. One region of SEQ ID NO:91 is from about nucleotide 83 to about nucleotide 150. One region of SEQ ID NO:91 is from about nucleotide 108 to about nucleotide 150 and the target hybridizing sequence contains a sequence identical or complementary to 5'-CAGTTG. (See, SEQ ID NOS:27, 33 & 92-101). Additions, deletions and mismatches may be incorporated into a promoter primer/promoter provider oligomer's target hybridizing sequence configured to hybridize to a region of SEQ ID NO:91. Representative target hybridizing sequences for some of the promoter primer/provider oligomers are shown in upper case lettering with an exemplary promoter sequence shown in lower case lettering in Table 1 (T7 Providers/Primer). Also shown in Table 1 are representative target hybridizing sequences (See SEQ ID NOS:19, 21, 23, 25, 27, 29, 31, 33, 35, 37, 39, 41, 43, 45, 47, & 49). These target hybridizing sequences are not limited to the target hybridizing sequence of a promoter based amplification oligomers, and can be used as primers or other amplification oligomer types.

Blocker oligomers may be used in a single primer transcription associated amplification reaction. Embodiments of 3' blocked oligomers include those of SEQ ID NOS:50-57 where an the 3' end of the sequence is preferably blocked to prevent primer-based nucleic acid synthesis from occurring. (See Table 1, Blocker)

TABLE 1

16S rRNA Amplification Oligonucleotides

| Use | SEQ ID NO: | Sequence (5'→3') |
|---|---|---|
| Primer | 1 | CACCGAAAAACTTTCCCTACTCAAC |
| Primer | 2 | CTACACCGAAAAACTTTCCCTACTCAAC |
| Primer | 3 | CCTACACCGAAAAACTTTCCCTACTCAAC |
| Primer | 4 | CACCGAAAAACTTTCCCTACTC |
| Primer | 5 | CTACACCGAAAAACTTTCCCTACTC |
| Primer | 6 | CCTACACCGAAAAACTTTCCCTACTC |
| Primer | 7 | GTCTCATCCTACACCGAAAAAC |
| Primer | 8 | CTATATAGTCTCATCCTACACCG |
| Primer | 9 | GCTGATACTATATAGTCTCATCCTACACCG |
| Primer | 10 | CTATATAGTCTCATCCTACACC |
| Primer | 11 | GCTGATACTATATAGTCTCATCCTACACC |
| Primer | 12 | CTATATAGTCTCATCCTACAC |
| Primer | 13 | CCAACTAGCTGATACTATATAGTCTCATCCTACAC |
| Primer | 14 | GCTGATACTATATAGTCTCATCC |
| Primer | 15 | GTGCGCCACTAATCCACTTC |
| Primer | 16 | CGTGCGCCACTAATCCACTT |
| Primer | 17 | CGTGCGCCACTAATCCACT |
| T7/Provider*/Primer | 18 | aatttaatacgactcactatagggag aCCTACACAAGAGGACAACAGTTG |
| Target Hybridizing Seq. | 19 | CCTACACAAGAGGACAACAGTTG |
| T7 Provider/Primer | 20 | aatttaatacgactcactatagggag aCCTACACAAGAGGACAACAGTTGG |
| Target Hybridizing Seq. | 21 | CCTACACAAGAGGACAACAGTTGG |
| T7 Provider/Primer | 22 | aatttaatacgactcactatagggag aCACAAGAGGACAACAGTTGGAAACG |
| Target Hybridizing Seq. | 23 | CACAAGAGGACAACAGTTGGAAACG |
| T7 Provider/Primer | 24 | aatttaatacgactcactatagggag aCACAAGAGGACAACAGTTGGAAACGAC |
| Target Hybridizing Seq. | 25 | CACAAGAGGACAACAGTTGGAAACGAC |
| T7 Provider/Primer | 26 | aatttaatacgactcactatagggag aAAGAGGACAACAGTTGGAAAC |
| Target Hybridizing Seq. | 27 | AAGAGGACAACAGTTGGAAAC |
| T7 Provider/Primer | 28 | aatttaatacgactcactatagggag aGGACAACAGTTGGAAACGACTGCTAATACTCT |

TABLE 1-continued 16S rRNA Amplification Oligonucleotides

| Use | SEQ ID NO: | Sequence (5'→3') |
|---|---|---|
| Target Hybridizing Seq. | 29 | GGACAACAGTTGGAAACGACTGCTAATACTCT |
| T7 Provider/Primer | 30 | aatttaatacgactcactatagggagaCAACAGTTGGAAACGACTGCTAATACTCT |
| Target Hybridizing Seq. | 31 | CAACAGTTGGAAACGACTGCTAATACTCT |
| T7 Provider/Primer | 32 | aatttaatacgactcactatagggagaCAGTTGGAAACGACTGCTAATACTCT |
| Target Hybridizing Seq. | 33 | CAGTTGGAAACGACTGCTAATACTCT |
| T7 Provider/Primer | 34 | aatttaatacgactcactatagggagaGGCGTGCCTAATACATGCAAGTCG |
| Target Hybridizing Seq. | 35 | GGCGTGCCTAATACATGCAAGTCG |
| T7 Provider/Primer | 36 | aatttaatacgactcactatagggagaCGTGCCTAATACATGCAAGTCG |
| Target Hybridizing Seq. | 37 | CGTGCCTAATACATGCAAGTCG |
| T7 Provider/Primer | 38 | aatttaatacgactcactatagggagaGCCTAATACATGCAAGTCGAAC |
| Target Hybridizing Seq. | 39 | GCCTAATACATGCAAGTCGAAC |
| T7 Provider/Primer | 40 | aatttaatacgactcactatagggagaCCTAATACATGCAAGTCGAACG |
| Target Hybridizing Seq. | 41 | CCTAATACATGCAAGTCGAACG |
| T7 Provider/Primer | 42 | aatttaatacgactcactatagggagaGCTAGAAGTGGATTAGTGGCGCAC |
| Target Hybridizing Seq. | 43 | GCTAGAAGTGGATTAGTGGCGCAC |
| T7 Provider/Primer | 44 | aatttaatacgactcactatagggagaGGATTAGTGGCGCACGGGTGAG |
| Target Hybridizing Seq. | 45 | GGATTAGTGGCGCACGGGTGAG |
| T7 Provider/Primer | 46 | aatttaatacgactcactatagggagaGGGTGAGTAAGGTATAGTTAATCTGC |
| Target Hybridizing Seq. | 47 | GGGTGAGTAAGGTATAGTTAATCTGC |
| T7 Provider/Primer | 48 | aatttaatacgactcactatagggagaGGTGAGTAAGGTATAGTTAATCTGCC |
| Target Hybridizing Seq. | 49 | GGTGAGTAAGGTATAGTTAATCTGCC |
| Blocker | 50 | CAACTGTTGTCCTCTTGTG |
| Blocker | 51 | CTAGCAAGCTAGAAGCTTC |
| Blocker | 52 | CTAATCCACTTCTAGCAAGC |
| Blocker | 53 | TCACCCGTGCGCCACTAATC |
| Blocker | 54 | TTAGGCACGCCGCCAG |
| Blocker | 55 | ATTAGGCACGCCGCCAG |
| Blocker | 56 | GTAGGGCAGATTAACTATAC |
| Blocker | 57 | CTTGTGTAGGGCAGATTAAC |

Some exemplary detection probes useful with the current invention include linear and hairpin oligonucleotides that are from about 10 to about 70 nucleotides in length and comprise a target hybridizing sequence that is configured to hybridize to either the "+" or the "−" strand of a region of SEQ ID NO:91, or RNA equivalent thereof, wherein the region of SEQ ID NO:91 is from about nucleotide 14 to about nucleotide 226; is from about nucleotide 108 to about nucleotide 226; is from about nucleotide 134 to about nucleotide 181; is from about nucleotide 159 to about nucleotide 181; is from about nucleotide 159 to about nucleotide 181 and the probe contains a sequence identical or complementary to nucleotides 167 to 181 of SEQ ID NO:91; is from about nucleotide 147 to about nucleotide 181; is from about nucleotide 163 to about nucleotide 181; or is from about nucleotide 163 to about nucleotide 181 and the probe contains a sequence identical or complementary to nucleotides 167 to 181. (See, SEQ ID NOS:102-106) Optionally, when the detection probe oligo is a molecular torch, the detection oligo also comprises target closing domains or other hairpin-forming structure. Additions, deletions and mismatches may be incorporated into a detection probe oligo designed to hybridize to a region of SEQ ID NO:91. Representative detection probe oligo sequences are shown in Table 2 as SEQ ID NOS:59-70 (Torch).

For the sequences listed in Table 2, the lowercase letters indicate the nucleotides in the sequence that form part of the closing domain, but are not part of the target binding sequence. Embodiments of the hairpin probe oligomers were synthesized with a fluorescent label attached at one end of the sequence and a quencher compound attached at the other end of the sequence. Some embodiments of hairpin oligomers also include a non-nucleotide linker moiety at selected positions within the sequence. Examples of such embodiments include those that include an abasic 9-carbon ("C9") linker between residues 6 and 7 of SEQ ID NO.: 70, between residues 15 and 16 of SEQ ID NO.: 68, between residues 16 and 17 of SEQ ID NO.: 61, between residues 17 and 18 of SEQ ID NO.: 67, between residues 18 and 19 of SEQ ID NO.: 69, between residues 20 and 21 of SEQ ID NO.: 66, between residues 21 and 22 of SEQ ID NO.: 63, between residues 23 and 25 of SEQ ID NO.: 62, between residues 24 and 25 of SEQ ID NO.: 65, between residues 25 and 26 of SEQ ID NOS.: 59 and 64, and between residues 26 and 27 of SEQ ID NO.:60. Detection probes may be used with helper probes that are unlabeled and facilitate binding of the labeled probe to its target as previously described (U.S. Pat. No. 5,030,557).

TABLE 2

16S rRNA Probes

| Use | SEQ ID NO: | Sequence (5'→3') |
|---|---|---|
| Torch | 59 | cGGAGTATAGAGTATTAGCAGTCGTcTCCg |
| Torch | 60 | GCAGGAGTATAGAGTATTAGCAGTCGcctgc |
| Torch | 61 | GCAGGAGTATAGAGTAcctGC |
| Torch | 62 | ccGTGTTAAGCAGGAGTATAGAGcacgg |
| Torch | 63 | ccGTGTTAAGCAGGAGTATAGcacgg |
| Torch | 64 | cTCCCTACTCAACTTGTGTTAAGCAGGgag |
| Torch | 65 | cTCCCTACTCAACTTGTGTTAAGCgGGAG |
| Torch | 66 | cTCCCTACTCAACTTGTGTTggGag |
| Torch | 67 | cTCCCTACTCAACTTGTGggag |
| Torch | 68 | cTCCCTACTCAACTTGggag |
| Torch | 69 | ccGCTAGAAGCTTCATCGagcgg |
| Torch | 70 | cggaaGCAAGCTAGAAGCTTCcg |

Capture probe oligomers may be used in sample preparation to separate *C. jejuni, C. lari*, and/or *C. coli* target nucleic acids from other sample components. Exemplary capture probe oligomers include those comprising a target-specific sequence of SEQ ID NOS:71-74. SEQ ID NOS:71 and 73 are embodiments of capture probes that include the target-specific sequences of SEQ ID NOS:72 and 74 and a binding partner that can be a nucleic acid or non-nucleic acid binding partner. SEQ ID NOS:72 and 74 each include a binding partner that is a dT.sub.3A.sub.30 polymer (underlined). Table 3.

TABLE 3

Capture Oligos.

| Use | SEQ ID NO: | Sequence (5'→3') |
|---|---|---|
| Target Capture | 71 | GCGTCAGGGTTTCCCCCATTGCGT TTAAAAAAAAAAAAAAAAAAAAA AAAAAAAA |
| Target Capture | 72 | GCGTCAGGGTTTCCCCCATTGCG [binding partner] |
| Target Capture | 73 | GCTTATTCCTTAGGTACCGTCAGT TTAAAAAAAAAAAAAAAAAAAAA AAAAAAAA |
| Target Capture | 74 | GCTTATTCCTTAGGTACCGTCAG [binding partner] |

EXAMPLE 1

Assay Reagents, Equipment and Protocols

The following example describes typical assay reagents, equipment, protocols, conditions and the like used in the real-time TMA experiments described herein. Unless specified to the contrary, reagent preparation, equipment preparation and assay protocols were performed essentially as set forth below. An ordinarily skilled artisan in possession of this disclosure can vary the reagents, conditions, instruments and assay methods, and such variations are within the scope of this disclosure.

Reagents used in target capture and amplification steps in the examples described herein generally included one or more of the following. Probe Matrix Lysis Reagent contained 0.1% (w/v) Lithium Lauryl Sulfate (LLS), 20 mM Lithium Succinate, and 1 mM EDTA. Lysis Reagent contained 1% (w/v) LLS, 100 mM Tris, 2.5 mM succinic acid, 10 mM EDTA, and 500 mM lithium chloride (LiCl) at pH 6.5. Target Capture Reagent contained 300 mM HEPES, 1.88 M lithium chloride, 100 mM EDTA, at pH 6.4, and 250 .micro.g/ml of paramagnetic particles (0.7-1.05 micron particles, SERA-MAG.sup.™ MG-CM, Seradyn, Inc., Indianapolis, Ind.) with (dT).sub.14 oligomers covalently bound thereto. Wash Solution used in target capture contained 10 mM HEPES, 150 mM NaCl, 1 mM EDTA, and 0.1% (w/v) sodium dodecyl sulfate, at pH 7.5. Amplification Reagent was mixed with other reaction components produce a solution containing 50 mM HEPES, 33 mM KCl, 30 mM MgCl.sub.2, 0.5 mM of each dNTP (dATP, dCTP, dGTP, dTTP), 10 mM ATP, 2 mM CTP, 12.7 mM UTP, 2 mM GTP, at pH 7.7. Amplification oligonucleotides (primers 0.125 pmol/.micro.L, promoter primers 0.125 pmol/.micro.L, blocker oligonucleotides 0.0125 pmol/.micro.L, promoter provider oligonucleotides) 0.125 pmol/.micro.L, and optionally probes 0.3 pmol/.micro.L, may be added to the reaction mixture in the amplification reagent or separate from the amplification reagent. Enzyme Reagent contained 360 RTU/.micro.l of Moloney murine leukemia virus (MMLV) reverse transcriptase (RT) and about 80 PU/.micro.l of T7 RNA polymerase, 75 mM HEPES, 120 mM KCl, 10% TRITON® X-100, 160 mM N-acetyl-L-cysteine, and 1 mM EDTA at pH 7.0, where 1 RTU of RT incorporates 1 nmol of dTTP in 20 min at 37.deg.C., and 1 PU of T7 RNA polymerase produces 5 nmol of RNA transcript in 20 min at 37.deg.C.

Equipment and Material generally included: KingFisher® 96 (Thermo Electron, Waltham, Mass.); KingFisher® mL (Thermo Electron, Waltham, Mass.); PTI-FP-2® FluoDia Plate Reader (Photon Technology International, Birmingham, N.J.); Eppendorf® Thermomixer R 022670565 (Eppendorf Corporation, Westbury, N.Y.); Hard-Shell Thin-Wall 96-Well Skirted PCR Plates, colored shell/white well, Catalog numbers: HSP-9615, HSP-9625, HSP-9635) (BioRad Hercules, Calif.); KingFisher® 96 tip comb for DW magnets (Catalog number: 97002534) Thermo Electron, Waltham, Mass.); DW 96 plate, V bottom, Polypropylene, sterile 25 pcs/case (Axygen Catalog number: P-2ML-SQ-C-S; VWR catalog number 47749-874); KingFisher® 96 KF plate (200 microliters) (Catalog number: 97002540); KingFisher® mL tip comb (Catalog number 97002111); and KingFisher® mL tubes (Catalog number 97002121).

The transcription mediated amplification (TMA) reactions use substantially the procedures as disclosed in U.S. Pat. Nos. 5,399,491 and 5,554,516. Single primer transcription associated amplification substantially use the procedures disclosed in detail in U.S. Pat. No. 7,374,885. The TAG amplification method has been disclosed in US Pub. No. 20070281317 A1. The use and detection of signal from AE-labeled probes to detect hybridization complexes with target sequences use the procedures already disclosed in detail in U.S. Pat. Nos. 5,283, 174; 5,656,744; and 5,658,737. The methods for using hairpin probes are well known, and include those already disclosed in detail in U.S. Pat. Nos. 6,849,412; 6,835,542; 6,534, 274; and 6,361,945.

By using various combinations of the herein described oligomers, including amplification oligomers and labeled detection probe oligomers, *C. jejuni, C. lari,* and/or *C. coli* target nucleic acids were specifically detected when the sample contained about 1E2 copies of the target nucleic acid.

The following examples illustrate some of the embodiments of the disclosure for detection of *C. jejuni, C. lari,* and/or *C. coli* target nucleic acid.

EXAMPLE 2

Design and Initial Testing of *C. jejuni, C. lari,* and *C. coli* 16S Oligomer Combination Sets Amplification and detection oligonucleotides were configured to discriminately amplify and detect *C. jejuni, C. lari,* and *C. coli* target nucleic acid. Using two overlapping regions of *Campylobacter jejuni* 16S rRNA corresponding to nucleotides 9-82 and nucleotides 44-226 of AF393202.1, gi:20378208, (SEQ ID NO:91), several T7 Providers, Blockers, Primers and Torches were configured to hybridize to smaller sequences within these regions of said reference sequence, as is described herein. The target hybridizing sequences of these oligomers also hybridize to a *C. jejuni* target nucleic acid and a *C. coli,* a *C. lari* or a *C. coli* and a *C. lari* target nucleic acid. In addition, using a region corresponding to base pairs 341-426 of this same *C. jejuni* 16S rRNA, several Target Capture Oligos were designed. (See Tables 1-3). These oligos were designed to maximize selective detection of the different strains of *C. jejuni, C. lari,* and *C. coli* with decreased potential for cross reactivity with other organisms.

A total of 942 different combinations of T7 Provider, Blocker, Primer and Torch oligos from Tables 1-2 were screened using a master-plate screening assay. Known amounts of *C. jejuni* target nucleic acids were amplified using real time single primer transcription associated amplification. Selecting one oligomer from each of the following groups produced the amplification oligomer combinations used in this initial screen: group 1 (SEQ ID NOS:1-17); group 2 (SEQ ID NOS:18, 20, 22, 24, 26, 28, 30, 32, 34, 36, 38, 40, 42, 46 or 48); group 3 (SEQ ID NOS:50-58); and group 4 (SEQ ID NOS:59-70). A master-plate was set up to contain 0.5 pM/.micro.L T7 Provider, 0.5 pM/.micro.L Primer, and 0.5 pM/.micro.L Blocker in amplification reagent at a final volume of 200 .micro.L per reaction well. Each reaction well contained one of the oligo combinations. The master-plate was kept at 20.deg.C.

Primary oligo screening included transferring 10 .micro.L of each oligo combination into a 96-well plate. *C. jejuni* target nucleic acid (American Type Cell Culture, Manassas, Va., ATCC 33560) was diluted to 1E5 copies per/20 .micro.l in amplification reagent and the diluted target was then added to each well of the 96-well plate so that the *C. jejuni* target nucleic acid was tested at 1E5 copies/reaction. A negative control containing oligos and Amplification mixture without target was included on the plates. The reaction mixtures containing the oligonucleotides, target and amplification reagents were covered to prevent evaporation, incubated 10 min at 60.deg.C. and then cooled to 42.deg.C. The enzyme reagent was added next at 10 .micro.L per well and the reactions were mixed and incubated at 42.deg.C.

Fluorescence was measured at regular time intervals (e.g., every 72 sec) during the amplification reaction for a total of 63 reads. Two colors were read at each interval. Monitoring was done using a real time fluorescent detection system (e.g., Bio-Rad Laboratory's Opticon.sup.™ or Chromo4.sup.™, or a FluoDia® T70 instrument). Real time algorithms are well known in the art, examples are described in Biochem Biophys Res Commun. 2002 Jun. 7; 294(2):347-53 and Nucleic Acids Research 2004 32(22):e178. The negative controls were tested to determine background fluorescent signal levels.

Raw data were gathered and analyzed to calculate signal emergence time (TTime) and range relative fluorescent units (RFUs). Oligo combinations were then grouped based upon TTime with TTime under 23 minutes being considered as the best combinations, TTimes between 23 minutes and 29 minutes being considered as adequate oligo combinations and TTimes of 30 or more minutes being unacceptable. Positive criterion depended on the instrument used. For instance, positive criterion was set at 0.05 RFU and was assessed over a 67-minute time course for the MJ Chromo4, whereas positive criterion was set at 1000 RFU and was assessed over a 75-minute time course using a different plate reader instrument. The oligomer combinations listed in Table 4 produced a fluorescent curve with a TTime less than or equal to 23 minutes. The oligomer combinations listed in Table 5 produced a fluorescent curve with a TTime between 23 and 30 minutes. From Tables 4 and 5, a preferred set of oligonucleotide combinations was selected for secondary screening. In addition to TTime, oligo combinations were also looked at to detect design flaws such as the number of mismatched nucleobases compared to *Campylobacter* species and the degree of burden for specificity placed upon each oligonucleotide in a combination. Other factors impacting the selection of oligo combinations for secondary screening included poor oligo compatibility and poor performance in amplifying and/or detecting target.

TABLE 4

*Campylobacter* Oligomer Combinations Less than 23 minutes

| Combo No. | SEQ ID NOS. |
|---|---|
| 1 | 1, 48, 53, 59 |
| 2 | 1, 18, 56, 59 |
| 3 | 1, 18, 57, 59 |
| 4 | 1, 20, 56, 59 |
| 5 | 1, 20, 57, 59 |
| 6 | 1, 46, 53, 60 |
| 7 | 1, 48, 53, 60 |
| 8 | 1, 18, 56, 60 |
| 9 | 1, 18, 57, 60 |
| 10 | 1, 20, 56, 60 |
| 11 | 1, 20, 57, 60 |
| 12 | 1, 46, 53, 61 |
| 13 | 1, 48, 53, 61 |
| 14 | 1, 18, 56, 61 |
| 15 | 1, 18, 57, 61 |
| 16 | 1, 20, 56, 61 |
| 17 | 1, 20, 57, 61 |
| 18 | 1, 48, 53, 62 |
| 19 | 1, 18, 56, 62 |
| 20 | 1, 18, 57, 62 |
| 21 | 1, 20, 56, 62 |
| 22 | 1, 20, 57, 62 |
| 23 | 1, 18, 56, 63 |
| 24 | 1, 18, 57, 63 |
| 25 | 1, 20, 56, 63 |
| 26 | 1, 20, 57, 63 |
| 27 | 2, 46, 53, 60 |
| 28 | 2, 18, 56, 60 |
| 29 | 2, 20, 56, 60 |
| 30 | 2, 20, 57, 60 |
| 31 | 2, 20, 56, 61 |
| 32 | 2, 20, 57, 61 |
| 33 | 4, 48, 53, 59 |
| 34 | 4, 18, 56, 59 |
| 35 | 4, 18, 57, 59 |
| 36 | 4, 20, 56, 59 |
| 37 | 4, 20, 57, 59 |
| 38 | 4, 46, 53, 60 |
| 39 | 4, 48, 53, 60 |
| 40 | 4, 18, 56, 60 |
| 41 | 4, 18, 57, 60 |

TABLE 4-continued

Campylobacter Oligomer Combinations Less than 23 minutes

| Combo No. | SEQ ID NOS. |
|---|---|
| 42 | 4, 20, 56, 60 |
| 43 | 4, 20, 57, 60 |
| 44 | 4, 46, 53, 61 |
| 45 | 4, 48, 53, 61 |
| 46 | 4, 18, 56, 61 |
| 47 | 4, 18, 57, 61 |
| 48 | 4, 20, 56, 61 |
| 49 | 4, 20, 57, 61 |
| 50 | 4, 48, 53, 62 |
| 51 | 4, 18, 56, 62 |
| 52 | 4, 18, 57, 62 |
| 53 | 4, 20, 56, 62 |
| 54 | 4, 20, 57, 62 |
| 55 | 4, 18, 56, 63 |
| 56 | 4, 18, 57, 63 |
| 57 | 4, 20, 56, 63 |
| 58 | 4, 20, 57, 63 |
| 59 | 5, 46, 53, 59 |
| 60 | 5, 18, 56, 59 |
| 61 | 5, 18, 57, 59 |
| 62 | 5, 20, 56, 59 |
| 63 | 5, 20, 57, 59 |
| 64 | 5, 46, 53, 60 |
| 65 | 5, 48, 53, 60 |
| 66 | 5, 18, 56, 60 |
| 67 | 5, 18, 57, 60 |
| 68 | 5, 20, 56, 60 |
| 69 | 5, 20, 57, 60 |
| 70 | 5, 46, 53, 61 |
| 71 | 5, 18, 56, 61 |
| 72 | 5, 18, 57, 61 |
| 73 | 5, 20, 56, 61 |
| 74 | 5, 20, 57, 61 |
| 75 | 5, 18, 56, 62 |
| 76 | 5, 20, 56, 62 |
| 77 | 5, 20, 57, 62 |
| 78 | 5, 20, 56, 63 |
| 79 | 5, 20, 57, 63 |
| 80 | 6, 46, 53, 60 |
| 81 | 6, 48, 53, 60 |
| 82 | 7, 20, 57, 59 |
| 83 | 7, 42, 51, 60 |
| 84 | 7, 44, 52, 60 |
| 85 | 7, 46, 53, 60 |
| 86 | 7, 48, 53, 60 |
| 87 | 7, 18, 56, 60 |
| 88 | 7, 18, 57, 60 |
| 89 | 7, 20, 56, 60 |
| 90 | 7, 20, 57, 60 |
| 91 | 7, 46, 53, 61 |
| 92 | 7, 48, 53, 61 |
| 93 | 7, 18, 56, 61 |
| 94 | 7, 18, 57, 61 |
| 95 | 7, 20, 56, 61 |
| 96 | 7, 20, 57, 61 |
| 97 | 7, 28, 50, 61 |
| 98 | 7, 30, 50, 61 |
| 99 | 7, 32, 50, 61 |
| 100 | 7, 20, 56, 62 |
| 101 | 7, 20, 57, 62 |
| 102 | 7, 24, 57, 62 |
| 103 | 7, 28, 50, 62 |
| 104 | 7, 30, 50, 62 |
| 105 | 7, 32, 50, 62 |
| 106 | 7, 46, 53, 63 |
| 107 | 7, 48, 53, 63 |
| 108 | 7, 18, 56, 63 |
| 109 | 7, 18, 57, 63 |
| 110 | 7, 20, 56, 63 |
| 111 | 7, 20, 57, 63 |
| 112 | 7, 28, 50, 63 |
| 113 | 7, 30, 50, 63 |
| 114 | 7, 32, 50, 63 |
| 115 | 7, 20, 57, 65 |
| 116 | 7, 28, 50, 65 |
| 117 | 7, 30, 50, 65 |
| 118 | 7, 32, 50, 65 |
| 119 | 7, 46, 53, 66 |
| 120 | 7, 48, 53, 66 |
| 121 | 7, 18, 56, 66 |
| 122 | 7, 18, 57, 66 |
| 123 | 7, 20, 56, 66 |
| 124 | 7, 20, 57, 66 |
| 125 | 7, 30, 50, 66 |
| 126 | 7, 32, 50, 66 |
| 127 | 7, 20, 57, 67 |
| 128 | 7, 28, 50, 67 |
| 129 | 7, 30, 50, 67 |
| 130 | 7, 32, 50, 67 |
| 131 | 7, 18, 57, 68 |
| 132 | 7, 32, 50, 68 |
| 133 | 7, 20, 56, 68 |
| 134 | 7, 20, 57, 68 |
| 135 | 7, 28, 50, 68 |
| 136 | 7, 30, 56, 68 |
| 137 | 8, 20, 56, 59 |
| 138 | 8, 20, 57, 59 |
| 139 | 8, 46, 53, 60 |
| 140 | 8, 48, 53, 60 |
| 141 | 8, 18, 56, 60 |
| 142 | 8, 18, 57, 60 |
| 143 | 8, 20, 56, 60 |
| 144 | 8, 20, 57, 60 |
| 145 | 8, 46, 53, 61 |
| 146 | 8, 48, 53, 61 |
| 147 | 8, 18, 56, 61 |
| 148 | 8, 18, 57, 61 |
| 149 | 8, 20, 56, 61 |
| 150 | 8, 20, 57, 61 |
| 151 | 8, 28, 50, 61 |
| 152 | 8, 30, 50, 61 |
| 153 | 8, 32, 50, 61 |
| 154 | 8, 18, 57, 62 |
| 155 | 8, 20, 56, 62 |
| 156 | 8, 20, 57, 62 |
| 157 | 8, 24, 57, 62 |
| 158 | 8, 28, 50, 62 |
| 159 | 8, 30, 50, 62 |
| 160 | 8, 32, 50, 62 |
| 161 | 8, 18, 56, 63 |
| 162 | 8, 18, 57, 63 |
| 163 | 8, 20, 56, 63 |
| 164 | 8, 20, 57, 63 |
| 165 | 8, 24, 57, 63 |
| 166 | 8, 28, 50, 63 |
| 167 | 8, 30, 50, 63 |
| 168 | 8, 32, 50, 63 |
| 169 | 8, 20, 56, 65 |
| 170 | 8, 20, 57, 65 |
| 171 | 8, 28, 50, 65 |
| 172 | 8, 30, 50, 65 |
| 173 | 8, 32, 50, 65 |
| 174 | 8, 18, 56, 66 |
| 175 | 8, 18, 57, 66 |
| 176 | 8, 20, 56, 66 |
| 177 | 8, 20, 57, 66 |
| 178 | 8, 28, 50, 66 |
| 179 | 8, 30, 50, 66 |
| 180 | 8, 32, 50, 66 |
| 181 | 8, 20, 56, 67 |
| 182 | 8, 20, 57, 67 |
| 183 | 8, 28, 50, 67 |
| 184 | 8, 30, 50, 67 |
| 185 | 8, 32, 50, 67 |
| 186 | 8, 18, 57, 68 |
| 187 | 8, 20, 56, 68 |
| 188 | 8, 20, 57, 68 |
| 189 | 8, 28, 50, 68 |
| 190 | 8, 30, 50, 68 |
| 191 | 8, 32, 50, 68 |

TABLE 4-continued

*Campylobacter* Oligomer Combinations Less than 23 minutes

| Combo No. | SEQ ID NOS. |
|---|---|
| 192 | 9, 48, 53, 59 |
| 193 | 9, 18, 56, 59 |
| 194 | 9, 18, 57, 59 |
| 195 | 9, 20, 56, 59 |
| 196 | 9, 20, 57, 59 |
| 197 | 9, 42, 51, 60 |
| 198 | 9, 46, 53, 60 |
| 199 | 9, 48, 53, 60 |
| 200 | 9, 18, 56, 60 |
| 201 | 9, 18, 57, 60 |
| 202 | 9, 20, 56, 60 |
| 203 | 9, 20, 57, 60 |
| 204 | 9, 42, 51, 61 |
| 205 | 9, 46, 53, 61 |
| 206 | 9, 48, 53, 61 |
| 207 | 9, 18, 56, 61 |
| 208 | 9, 18, 57, 61 |
| 209 | 9, 20, 56, 61 |
| 210 | 9, 20, 57, 61 |
| 211 | 9, 28, 50, 61 |
| 212 | 9, 30, 50, 61 |
| 213 | 9, 32, 50, 61 |
| 214 | 9, 48, 53, 62 |
| 215 | 9, 18, 56, 62 |
| 216 | 9, 18, 57, 62 |
| 217 | 9, 20, 56, 62 |
| 218 | 9, 20, 57, 62 |
| 219 | 9, 32, 50, 62 |
| 220 | 9, 46, 53, 63 |
| 221 | 9, 48, 53, 63 |
| 222 | 9, 18, 56, 63 |
| 223 | 9, 18, 57, 63 |
| 224 | 9, 20, 56, 63 |
| 225 | 9, 20, 57, 63 |
| 226 | 9, 24, 57, 63 |
| 227 | 9, 30, 50, 63 |
| 228 | 9, 32, 50, 63 |
| 229 | 9, 48, 53, 65 |
| 230 | 9, 20, 56, 65 |
| 231 | 9, 20, 57, 65 |
| 232 | 9, 28, 50, 65 |
| 233 | 9, 30, 50, 65 |
| 234 | 9, 32, 50, 65 |
| 235 | 9, 46, 53, 66 |
| 236 | 9, 48, 53, 66 |
| 237 | 9, 18, 56, 66 |
| 238 | 9, 18, 57, 66 |
| 239 | 9, 20, 56, 66 |
| 240 | 9, 20, 57, 66 |
| 241 | 9, 28, 50, 66 |
| 242 | 9, 30, 50, 66 |
| 243 | 9, 32, 50, 66 |
| 244 | 9, 20, 56, 67 |
| 245 | 9, 20, 57, 67 |
| 246 | 9, 28, 50, 67 |
| 247 | 9, 30, 50, 67 |
| 248 | 9, 32, 50, 67 |
| 249 | 9, 46, 53, 68 |
| 250 | 9, 48, 53, 68 |
| 251 | 9, 18, 56, 68 |
| 252 | 9, 18, 57, 68 |
| 253 | 9, 20, 56, 68 |
| 254 | 9, 20, 57, 68 |
| 255 | 9, 28, 50, 68 |
| 256 | 9, 30, 50, 68 |
| 257 | 9, 32, 50, 68 |
| 258 | 10, 20, 56, 59 |
| 259 | 10, 20, 57, 59 |
| 260 | 10, 46, 53, 60 |
| 261 | 10, 48, 53, 60 |
| 262 | 10, 18, 56, 60 |
| 263 | 10, 18, 57, 60 |
| 264 | 10, 20, 56, 60 |
| 265 | 10, 20, 57, 60 |
| 266 | 10, 46, 53, 61 |
| 267 | 10, 48, 53, 61 |
| 268 | 10, 18, 56, 61 |
| 269 | 10, 18, 57, 61 |
| 270 | 10, 20, 56, 61 |
| 271 | 10, 20, 57, 61 |
| 272 | 10, 28, 50, 61 |
| 273 | 10, 30, 50, 61 |
| 274 | 10, 32, 50, 61 |
| 275 | 10, 18, 57, 62 |
| 276 | 10, 20, 56, 62 |
| 277 | 10, 20, 57, 62 |
| 278 | 10, 24, 57, 62 |
| 279 | 10, 28, 50, 62 |
| 280 | 10, 30, 50, 62 |
| 281 | 10, 32, 50, 62 |
| 282 | 10, 18, 56, 63 |
| 283 | 10, 18, 57, 63 |
| 284 | 10, 20, 56, 63 |
| 285 | 10, 20, 57, 63 |
| 286 | 10, 30, 50, 63 |
| 287 | 10, 32, 50, 63 |
| 288 | 10, 20, 56, 65 |
| 289 | 10, 20, 57, 65 |
| 290 | 10, 28, 50, 65 |
| 291 | 10, 30, 50, 65 |
| 292 | 10, 32, 50, 65 |
| 293 | 10, 18, 56, 66 |
| 294 | 10, 18, 57, 66 |
| 295 | 10, 20, 56, 66 |
| 296 | 10, 20, 57, 66 |
| 297 | 10, 28, 50, 66 |
| 298 | 10, 30, 50, 66 |
| 299 | 10, 32, 50, 66 |
| 300 | 10, 18, 57, 67 |
| 301 | 10, 20, 56, 67 |
| 302 | 10, 20, 57, 67 |
| 303 | 10, 28, 50, 67 |
| 304 | 10, 30, 50, 67 |
| 305 | 10, 32, 50, 67 |
| 306 | 10, 18, 57, 68 |
| 307 | 10, 20, 56, 68 |
| 308 | 10, 20, 57, 68 |
| 309 | 10, 28, 50, 68 |
| 310 | 10, 30, 50, 68 |
| 311 | 10, 32, 50, 68 |
| 312 | 11, 48, 53, 59 |
| 313 | 11, 18, 57, 59 |
| 314 | 11, 20, 56, 59 |
| 315 | 11, 20, 57, 59 |
| 316 | 11, 42, 51, 60 |
| 317 | 11, 44, 52, 60 |
| 318 | 11, 46, 53, 60 |
| 319 | 11, 48, 53, 60 |
| 320 | 11, 18, 56, 60 |
| 321 | 11, 18, 57, 60 |
| 322 | 11, 20, 56, 60 |
| 323 | 11, 20, 57, 60 |
| 324 | 11, 46, 53, 61 |
| 325 | 11, 48, 53, 61 |
| 326 | 11, 18, 56, 61 |
| 327 | 11, 18, 57, 61 |
| 328 | 11, 20, 56, 61 |
| 329 | 11, 20, 57, 61 |
| 330 | 11, 24, 57, 61 |
| 331 | 11, 28, 50, 61 |
| 332 | 11, 30, 50, 61 |
| 333 | 11, 32, 50, 61 |
| 334 | 11, 48, 53, 62 |
| 335 | 11, 18, 57, 62 |
| 336 | 11, 20, 56, 62 |
| 337 | 11, 20, 57, 62 |
| 338 | 11, 22, 57, 62 |
| 339 | 11, 32, 50, 62 |
| 340 | 11, 46, 53, 63 |
| 341 | 11, 48, 53, 63 |

TABLE 4-continued

Campylobacter Oligomer Combinations Less than 23 minutes

| Combo No. | SEQ ID NOS. |
|---|---|
| 342 | 11, 18, 56, 63 |
| 343 | 11, 18, 57, 63 |
| 344 | 11, 20, 56, 63 |
| 345 | 11, 20, 57, 63 |
| 346 | 11, 48, 53, 65 |
| 347 | 11, 18, 56, 65 |
| 348 | 11, 20, 56, 65 |
| 349 | 11, 20, 57, 65 |
| 350 | 11, 28, 50, 65 |
| 351 | 11, 30, 50, 65 |
| 352 | 11, 32, 50, 65 |
| 353 | 11, 46, 53, 66 |
| 354 | 11, 48, 53, 66 |
| 355 | 11, 18, 56, 66 |
| 356 | 11, 18, 57, 66 |
| 357 | 11, 20, 56, 66 |
| 358 | 11, 20, 57, 66 |
| 359 | 11, 28, 50, 66 |
| 360 | 11, 30, 50, 66 |
| 361 | 11, 32, 50, 66 |
| 362 | 11, 48, 53, 67 |
| 363 | 11, 18, 57, 67 |
| 364 | 11, 20, 56, 67 |
| 365 | 11, 20, 57, 67 |
| 366 | 11, 28, 50, 67 |
| 367 | 11, 30, 50, 67 |
| 368 | 11, 32, 50, 67 |
| 369 | 11, 48, 53, 68 |
| 370 | 11, 18, 57, 68 |
| 371 | 11, 20, 56, 68 |
| 372 | 11, 20, 57, 68 |
| 373 | 11, 28, 50, 68 |
| 374 | 11, 30, 50, 68 |
| 375 | 11, 32, 50, 68 |
| 376 | 12, 48, 53, 59 |
| 377 | 12, 18, 57, 59 |
| 378 | 12, 20, 56, 59 |
| 379 | 12, 20, 57, 59 |
| 380 | 12, 42, 51, 60 |
| 381 | 12, 44, 52, 60 |
| 382 | 12, 46, 53, 60 |
| 383 | 12, 48, 53, 60 |
| 384 | 12, 18, 56, 60 |
| 385 | 12, 18, 57, 60 |
| 386 | 12, 20, 56, 60 |
| 387 | 12, 20, 57, 60 |
| 388 | 12, 46, 53, 61 |
| 389 | 12, 48, 53, 61 |
| 390 | 12, 18, 56, 61 |
| 391 | 12, 18, 57, 61 |
| 392 | 12, 20, 56, 61 |
| 393 | 12, 20, 57, 61 |
| 394 | 12, 28, 50, 61 |
| 395 | 12, 30, 50, 61 |
| 396 | 12, 32, 50, 61 |
| 397 | 12, 48, 53, 62 |
| 398 | 12, 18, 57, 62 |
| 399 | 12, 20, 56, 62 |
| 400 | 12, 20, 57, 62 |
| 401 | 12, 46, 53, 63 |
| 402 | 12, 48, 53, 63 |
| 403 | 12, 18, 56, 63 |
| 404 | 12, 18, 57, 63 |
| 405 | 12, 20, 56, 63 |
| 406 | 12, 20, 57, 63 |
| 407 | 12, 20, 56, 65 |
| 408 | 12, 20, 57, 65 |
| 409 | 12, 28, 50, 65 |
| 410 | 12, 30, 50, 65 |
| 411 | 12, 32, 50, 65 |
| 412 | 12, 18, 56, 66 |
| 413 | 12, 18, 57, 66 |
| 414 | 12, 20, 56, 66 |
| 415 | 12, 20, 57, 66 |
| 416 | 12, 28, 50, 66 |
| 417 | 12, 30, 50, 66 |
| 418 | 12, 32, 50, 66 |
| 419 | 12, 20, 56, 67 |
| 420 | 12, 20, 57, 67 |
| 421 | 12, 28, 50, 67 |
| 422 | 12, 30, 50, 67 |
| 423 | 12, 32, 50, 67 |
| 424 | 12, 18, 57, 68 |
| 425 | 12, 20, 56, 68 |
| 426 | 12, 20, 57, 68 |
| 427 | 12, 28, 50, 68 |
| 428 | 12, 30, 50, 68 |
| 429 | 12, 32, 50, 68 |
| 430 | 13, 18, 56, 59 |
| 431 | 13, 18, 57, 59 |
| 432 | 13, 20, 56, 59 |
| 433 | 13, 20, 57, 59 |
| 434 | 13, 18, 56, 60 |
| 435 | 13, 18, 57, 60 |
| 436 | 13, 20, 56, 60 |
| 437 | 13, 18, 57, 61 |
| 438 | 13, 20, 56, 61 |
| 439 | 13, 28, 50, 61 |
| 440 | 13, 30, 50, 61 |
| 441 | 13, 32, 50, 61 |
| 442 | 13, 46, 53, 62 |
| 443 | 13, 48, 53, 62 |
| 444 | 13, 18, 56, 62 |
| 445 | 13, 18, 57, 62 |
| 446 | 13, 20, 56, 62 |
| 447 | 13, 32, 50, 62 |
| 448 | 13, 46, 53, 63 |
| 449 | 13, 48, 53, 63 |
| 450 | 13, 18, 56, 63 |
| 451 | 13, 18, 57, 63 |
| 452 | 13, 20, 56, 63 |
| 453 | 13, 20, 57, 63 |
| 454 | 13, 20, 56, 65 |
| 455 | 13, 20, 57, 65 |
| 456 | 13, 28, 50, 65 |
| 457 | 13, 30, 50, 65 |
| 458 | 13, 32, 50, 65 |
| 459 | 13, 20, 56, 66 |
| 460 | 13, 20, 57, 66 |
| 461 | 13, 28, 50, 66 |
| 462 | 13, 30, 50, 66 |
| 463 | 13, 32, 50, 66 |
| 464 | 13, 20, 56, 67 |
| 465 | 13, 20, 57, 67 |
| 466 | 13, 28, 50, 67 |
| 467 | 13, 30, 50, 67 |
| 468 | 13, 32, 50, 67 |
| 469 | 13, 20, 57, 68 |
| 470 | 13, 28, 50, 68 |
| 471 | 13, 30, 50, 68 |
| 472 | 13, 32, 50, 68 |
| 473 | 14, 48, 53, 59 |
| 474 | 14, 18, 56, 59 |
| 475 | 14, 18, 57, 59 |
| 476 | 14, 20, 56, 59 |
| 477 | 14, 20, 57, 59 |
| 478 | 14, 46, 53, 60 |
| 479 | 14, 48, 53, 60 |
| 480 | 14, 18, 56, 60 |
| 481 | 14, 18, 57, 60 |
| 482 | 14, 20, 56, 60 |
| 483 | 14, 20, 57, 60 |
| 484 | 14, 48, 53, 61 |
| 485 | 14, 18, 57, 61 |
| 486 | 14, 20, 57, 61 |
| 487 | 14, 28, 50, 61 |
| 488 | 14, 30, 50, 61 |
| 489 | 14, 32, 50, 61 |
| 490 | 14, 46, 53, 62 |
| 491 | 14, 48, 53, 62 |

TABLE 4-continued

Campylobacter Oligomer Combinations Less than 23 minutes

| Combo No. | SEQ ID NOS. |
|---|---|
| 492 | 14, 18, 56, 62 |
| 493 | 14, 18, 57, 62 |
| 494 | 14, 20, 56, 62 |
| 495 | 14, 46, 53, 63 |
| 496 | 14, 48, 53, 63 |
| 497 | 14, 18, 56, 63 |
| 498 | 14, 18, 57, 63 |
| 499 | 14, 20, 56, 63 |
| 500 | 14, 20, 57, 63 |
| 501 | 14, 28, 50, 65 |
| 502 | 14, 30, 50, 65 |
| 503 | 14, 32, 50, 65 |
| 504 | 14, 48, 53, 66 |
| 505 | 14, 18, 57, 66 |
| 506 | 14, 28, 50, 66 |
| 507 | 14, 30, 50, 66 |
| 508 | 14, 32, 50, 66 |
| 509 | 14, 48, 53, 67 |
| 510 | 14, 18, 57, 67 |
| 511 | 14, 28, 50, 67 |
| 512 | 14, 30, 50, 67 |
| 513 | 14, 32, 50, 67 |
| 514 | 14, 20, 56, 68 |
| 515 | 14, 20, 57, 68 |
| 516 | 14, 30, 50, 68 |
| 517 | 14, 32, 50, 68 |
| 518 | 15, 34, 54, 69 |
| 519 | 15, 34, 55, 69 |
| 520 | 15, 36, 54, 69 |
| 521 | 15, 38, 54, 69 |
| 522 | 15, 40, 54, 69 |
| 523 | 15, 34, 54, 70 |
| 524 | 15, 34, 55, 70 |
| 525 | 15, 36, 54, 70 |
| 526 | 15, 36, 55, 70 |
| 527 | 15, 38, 54, 70 |
| 528 | 15, 38, 55, 70 |
| 529 | 15, 40, 54, 70 |
| 530 | 15, 40, 55, 70 |
| 531 | 16, 34, 54, 69 |
| 532 | 16, 36, 54, 69 |
| 533 | 16, 38, 54, 69 |
| 534 | 16, 40, 54, 69 |
| 535 | 16, 40, 55, 69 |
| 536 | 16, 34, 54, 70 |
| 537 | 16, 34, 55, 70 |
| 538 | 16, 36, 54, 70 |
| 539 | 16, 36, 55, 70 |
| 540 | 16, 38, 54, 70 |
| 541 | 16, 38, 55, 70 |
| 542 | 16, 40, 54, 70 |
| 543 | 16, 40, 55, 70 |
| 544 | 17, 34, 54, 69 |
| 545 | 17, 36, 54, 69 |
| 546 | 17, 38, 54, 69 |
| 547 | 17, 40, 54, 69 |
| 548 | 17, 40, 55, 69 |
| 549 | 17, 34, 54, 70 |
| 550 | 17, 34, 55, 70 |
| 551 | 17, 36, 54, 70 |
| 552 | 17, 36, 55, 70 |
| 553 | 17, 38, 54, 70 |
| 554 | 17, 38, 55, 70 |
| 555 | 17, 40, 54, 70 |
| 556 | 17, 40, 55, 70 |

TABLE 5

Campylobacter Oligomer Combinations 23-29 minutes

| Combo No. | SEQ ID NOS. |
|---|---|
| 557 | 1, 46, 53, 59 |
| 558 | 1, 42, 51, 60 |
| 559 | 1, 44, 52, 60 |
| 560 | 1, 22, 57, 61 |
| 561 | 1, 24, 57, 61 |
| 562 | 1, 46, 53, 62 |
| 563 | 1, 22, 57, 62 |
| 564 | 1, 24, 57, 62 |
| 565 | 1, 46, 53, 63 |
| 566 | 1, 48, 53, 63 |
| 567 | 1, 22, 57, 63 |
| 568 | 1, 24, 57, 63 |
| 569 | 2, 42, 51, 59 |
| 570 | 2, 46, 53, 59 |
| 571 | 2, 48, 53, 59 |
| 572 | 2, 18, 56, 59 |
| 573 | 2, 18, 57, 59 |
| 574 | 2, 20, 56, 59 |
| 575 | 2, 20, 57, 59 |
| 576 | 2, 48, 53, 60 |
| 577 | 2, 18, 57, 60 |
| 578 | 2, 46, 53, 61 |
| 579 | 2, 18, 56, 61 |
| 580 | 2, 18, 57, 61 |
| 581 | 2, 22, 57, 61 |
| 582 | 2, 24, 57, 61 |
| 583 | 2, 46, 53, 62 |
| 584 | 2, 18, 56, 62 |
| 585 | 2, 18, 57, 62 |
| 586 | 2, 20, 56, 62 |
| 587 | 2, 20, 57, 62 |
| 588 | 2, 22, 57, 62 |
| 589 | 2, 24, 57, 62 |
| 590 | 2, 46, 53, 63 |
| 591 | 2, 18, 56, 63 |
| 592 | 2, 18, 57, 63 |
| 593 | 2, 20, 56, 63 |
| 594 | 2, 20, 57, 63 |
| 595 | 2, 22, 57, 63 |
| 596 | 2, 24, 57, 63 |
| 597 | 3, 46, 53, 59 |
| 598 | 3, 18, 56, 59 |
| 599 | 3, 18, 57, 59 |
| 600 | 3, 20, 56, 59 |
| 601 | 3, 20, 57, 59 |
| 602 | 3, 44, 52, 60 |
| 603 | 3, 46, 53, 60 |
| 604 | 3, 48, 53, 60 |
| 605 | 3, 18, 56, 60 |
| 606 | 3, 18, 57, 60 |
| 607 | 3, 20, 56, 60 |
| 608 | 3, 20, 57, 60 |
| 609 | 3, 18, 56, 61 |
| 610 | 3, 18, 57, 61 |
| 611 | 3, 20, 56, 61 |
| 612 | 3, 20, 57, 61 |
| 613 | 3, 22, 57, 61 |
| 614 | 3, 24, 57, 61 |
| 615 | 3, 18, 56, 62 |
| 616 | 3, 18, 57, 62 |
| 617 | 3, 20, 57, 62 |
| 618 | 3, 22, 57, 62 |
| 619 | 3, 24, 57, 62 |
| 620 | 3, 22, 57, 63 |
| 621 | 3, 24, 57, 63 |
| 622 | 4, 46, 53, 59 |
| 623 | 4, 22, 57, 61 |
| 624 | 4, 24, 57, 61 |
| 625 | 4, 46, 53, 62 |
| 626 | 4, 22, 57, 62 |
| 627 | 4, 24, 57, 62 |
| 628 | 4, 46, 53, 63 |
| 629 | 4, 48, 53, 63 |
| 630 | 4, 22, 57, 63 |
| 631 | 4, 24, 57, 63 |

TABLE 5-continued

Campylobacter Oligomer Combinations 23-29 minutes

| Combo No. | SEQ ID NOS. |
|---|---|
| 632 | 5, 48, 53, 59 |
| 633 | 5, 22, 57, 61 |
| 634 | 5, 24, 57, 61 |
| 635 | 5, 46, 53, 62 |
| 636 | 5, 18, 57, 62 |
| 637 | 5, 22, 57, 62 |
| 638 | 5, 24, 57, 62 |
| 639 | 5, 46, 53, 63 |
| 640 | 5, 48, 53, 63 |
| 641 | 5, 18, 56, 63 |
| 642 | 5, 18, 57, 63 |
| 643 | 5, 22, 57, 63 |
| 644 | 5, 24, 57, 63 |
| 645 | 6, 46, 53, 59 |
| 646 | 6, 48, 53, 59 |
| 647 | 6, 18, 56, 59 |
| 648 | 6, 18, 57, 59 |
| 649 | 6, 20, 56, 59 |
| 650 | 6, 20, 57, 59 |
| 651 | 6, 18, 56, 60 |
| 652 | 6, 18, 57, 60 |
| 653 | 6, 20, 56, 60 |
| 654 | 6, 20, 57, 60 |
| 655 | 6, 46, 53, 61 |
| 656 | 6, 18, 56, 61 |
| 657 | 6, 18, 57, 61 |
| 658 | 6, 20, 56, 61 |
| 659 | 6, 20, 57, 61 |
| 660 | 6, 22, 57, 61 |
| 661 | 6, 24, 57, 61 |
| 662 | 6, 46, 53, 62 |
| 663 | 6, 48, 53, 62 |
| 664 | 6, 18, 56, 62 |
| 665 | 6, 18, 57, 62 |
| 666 | 6, 20, 56, 62 |
| 667 | 6, 20, 57, 62 |
| 668 | 6, 22, 57, 62 |
| 669 | 6, 24, 57, 62 |
| 670 | 6, 46, 53, 63 |
| 671 | 6, 18, 56, 63 |
| 672 | 6, 18, 57, 63 |
| 673 | 6, 20, 56, 63 |
| 674 | 6, 20, 57, 63 |
| 675 | 6, 22, 57, 63 |
| 676 | 6, 24, 57, 63 |
| 677 | 7, 46, 53, 59 |
| 678 | 7, 48, 53, 59 |
| 679 | 7, 18, 56, 59 |
| 680 | 7, 18, 57, 59 |
| 681 | 7, 20, 56, 59 |
| 682 | 7, 42, 51, 61 |
| 683 | 7, 44, 52, 61 |
| 684 | 7, 22, 57, 61 |
| 685 | 7, 24, 57, 61 |
| 686 | 7, 46, 53, 62 |
| 687 | 7, 48, 53, 62 |
| 688 | 7, 18, 56, 62 |
| 689 | 7, 18, 57, 62 |
| 690 | 7, 22, 57, 62 |
| 691 | 7, 22, 57, 63 |
| 692 | 7, 24, 57, 63 |
| 693 | 7, 22, 57, 64 |
| 694 | 7, 24, 57, 64 |
| 695 | 7, 46, 53, 65 |
| 696 | 7, 48, 53, 65 |
| 697 | 7, 18, 56, 65 |
| 698 | 7, 18, 57, 65 |
| 699 | 7, 20, 56, 65 |
| 700 | 7, 22, 57, 65 |
| 701 | 7, 24, 57, 65 |
| 702 | 7, 22, 57, 66 |
| 703 | 7, 24, 57, 66 |
| 704 | 7, 28, 50, 66 |
| 705 | 7, 46, 53, 67 |
| 706 | 7, 48, 53, 67 |
| 707 | 7, 18, 56, 67 |
| 708 | 7, 18, 57, 67 |
| 709 | 7, 20, 56, 67 |
| 710 | 7, 22, 57, 67 |
| 711 | 7, 24, 57, 67 |
| 712 | 7, 46, 53, 68 |
| 713 | 7, 48, 53, 68 |
| 714 | 7, 18, 56, 68 |
| 715 | 7, 22, 57, 68 |
| 716 | 7, 24, 57, 68 |
| 717 | 8, 46, 53, 59 |
| 718 | 8, 18, 56, 59 |
| 719 | 8, 18, 57, 59 |
| 720 | 8, 22, 57, 61 |
| 721 | 8, 24, 57, 61 |
| 722 | 8, 46, 53, 62 |
| 723 | 8, 18, 56, 62 |
| 724 | 8, 22, 57, 62 |
| 725 | 8, 46, 53, 63 |
| 726 | 8, 48, 53, 63 |
| 727 | 8, 22, 57, 63 |
| 728 | 8, 22, 57, 64 |
| 729 | 8, 24, 57, 64 |
| 730 | 8, 18, 56, 65 |
| 731 | 8, 18, 57, 65 |
| 732 | 8, 22, 57, 65 |
| 733 | 8, 24, 57, 65 |
| 734 | 8, 46, 53, 66 |
| 735 | 8, 48, 53, 66 |
| 736 | 8, 22, 57, 66 |
| 737 | 8, 24, 57, 66 |
| 738 | 8, 18, 56, 67 |
| 739 | 8, 18, 57, 67 |
| 740 | 8, 22, 57, 67 |
| 741 | 8, 24, 57, 67 |
| 742 | 8, 46, 53, 68 |
| 743 | 8, 18, 56, 68 |
| 744 | 8, 22, 57, 68 |
| 745 | 8, 24, 57, 68 |
| 746 | 9, 46, 53, 59 |
| 747 | 9, 22, 57, 61 |
| 748 | 9, 24, 57, 61 |
| 749 | 9, 46, 53, 62 |
| 750 | 9, 22, 57, 62 |
| 751 | 9, 24, 57, 62 |
| 752 | 9, 28, 50, 62 |
| 753 | 9, 30, 50, 62 |
| 754 | 9, 22, 57, 63 |
| 755 | 9, 28, 50, 63 |
| 756 | 9, 22, 57, 64 |
| 757 | 9, 24, 57, 64 |
| 758 | 9, 46, 53, 65 |
| 759 | 9, 18, 56, 65 |
| 760 | 9, 18, 57, 65 |
| 761 | 9, 22, 57, 65 |
| 762 | 9, 24, 57, 65 |
| 763 | 9, 22, 57, 66 |
| 764 | 9, 24, 57, 66 |
| 765 | 9, 46, 53, 67 |
| 766 | 9, 48, 53, 67 |
| 767 | 9, 18, 56, 67 |
| 768 | 9, 18, 57, 67 |
| 769 | 9, 22, 57, 67 |
| 770 | 9, 24, 57, 67 |
| 771 | 9, 22, 57, 68 |
| 772 | 9, 24, 57, 68 |
| 773 | 10, 18, 57, 59 |
| 774 | 10, 22, 57, 61 |
| 775 | 10, 24, 57, 61 |
| 776 | 10, 48, 53, 62 |
| 777 | 10, 18, 56, 62 |
| 778 | 10, 22, 57, 62 |
| 779 | 10, 46, 53, 63 |
| 780 | 10, 48, 53, 63 |
| 781 | 10, 22, 57, 63 |

TABLE 5-continued

Campylobacter Oligomer Combinations 23-29 minutes

| Combo No. | SEQ ID NOS. |
|---|---|
| 782 | 10, 24, 57, 63 |
| 783 | 10, 28, 50, 63 |
| 784 | 10, 22, 57, 64 |
| 785 | 10, 24, 57, 64 |
| 786 | 10, 18, 56, 65 |
| 787 | 10, 18, 57, 65 |
| 788 | 10, 22, 57, 65 |
| 789 | 10, 24, 57, 65 |
| 790 | 10, 46, 53, 66 |
| 791 | 10, 48, 53, 66 |
| 792 | 10, 22, 57, 66 |
| 793 | 10, 24, 57, 66 |
| 794 | 10, 48, 53, 67 |
| 795 | 10, 18, 56, 67 |
| 796 | 10, 22, 57, 67 |
| 797 | 10, 24, 57, 67 |
| 798 | 10, 48, 53, 68 |
| 799 | 10, 18, 56, 68 |
| 800 | 10, 22, 57, 68 |
| 801 | 10, 24, 57, 68 |
| 802 | 11, 46, 53, 59 |
| 803 | 11, 18, 56, 59 |
| 804 | 11, 42, 51, 61 |
| 805 | 11, 22, 57, 61 |
| 806 | 11, 46, 53, 62 |
| 807 | 11, 18, 56, 62 |
| 808 | 11, 24, 57, 62 |
| 809 | 11, 28, 50, 62 |
| 810 | 11, 30, 50, 62 |
| 811 | 11, 42, 51, 63 |
| 812 | 11, 22, 57, 63 |
| 813 | 11, 24, 57, 63 |
| 814 | 11, 28, 50, 63 |
| 815 | 11, 30, 50, 63 |
| 816 | 11, 32, 50, 63 |
| 817 | 11, 24, 57, 64 |
| 818 | 11, 42, 51, 65 |
| 819 | 11, 46, 53, 65 |
| 820 | 11, 18, 57, 65 |
| 821 | 11, 22, 57, 65 |
| 822 | 11, 24, 57, 65 |
| 823 | 11, 22, 57, 66 |
| 824 | 11, 24, 57, 66 |
| 825 | 11, 46, 53, 67 |
| 826 | 11, 18, 56, 67 |
| 827 | 11, 22, 57, 67 |
| 828 | 11, 24, 57, 67 |
| 829 | 11, 46, 53, 68 |
| 830 | 11, 18, 56, 68 |
| 831 | 11, 22, 57, 68 |
| 832 | 11, 24, 57, 68 |
| 833 | 12, 46, 53, 59 |
| 834 | 12, 18, 56, 59 |
| 835 | 12, 42, 51, 61 |
| 836 | 12, 44, 52, 61 |
| 837 | 12, 22, 57, 61 |
| 838 | 12, 24, 57, 61 |
| 839 | 12, 46, 53, 62 |
| 840 | 12, 18, 56, 62 |
| 841 | 12, 22, 57, 62 |
| 842 | 12, 24, 57, 62 |
| 843 | 12, 28, 50, 62 |
| 844 | 12, 30, 50, 62 |
| 845 | 12, 32, 50, 62 |
| 846 | 12, 42, 51, 63 |
| 847 | 12, 22, 57, 63 |
| 848 | 12, 24, 57, 63 |
| 849 | 12, 24, 57, 64 |
| 850 | 12, 48, 53, 65 |
| 851 | 12, 18, 56, 65 |
| 852 | 12, 18, 57, 65 |
| 853 | 12, 22, 57, 65 |
| 854 | 12, 24, 57, 65 |
| 855 | 12, 46, 53, 66 |
| 856 | 12, 48, 53, 66 |
| 857 | 12, 22, 57, 66 |
| 858 | 12, 24, 57, 66 |
| 859 | 12, 46, 53, 67 |
| 860 | 12, 48, 53, 67 |
| 861 | 12, 18, 56, 67 |
| 862 | 12, 18, 57, 67 |
| 863 | 12, 22, 57, 67 |
| 864 | 12, 24, 57, 67 |
| 865 | 12, 48, 53, 68 |
| 866 | 12, 18, 56, 68 |
| 867 | 12, 22, 57, 68 |
| 868 | 12, 24, 57, 68 |
| 869 | 13, 20, 57, 60 |
| 870 | 13, 18, 56, 61 |
| 871 | 13, 20, 57, 61 |
| 872 | 13, 22, 57, 61 |
| 873 | 13, 24, 57, 61 |
| 874 | 13, 22, 57, 62 |
| 875 | 13, 24, 57, 62 |
| 876 | 13, 28, 50, 62 |
| 877 | 13, 30, 50, 62 |
| 878 | 13, 22, 57, 63 |
| 879 | 13, 24, 57, 63 |
| 880 | 13, 30, 50, 63 |
| 881 | 13, 32, 50, 63 |
| 882 | 13, 22, 57, 64 |
| 883 | 13, 24, 57, 64 |
| 884 | 13, 18, 56, 65 |
| 885 | 13, 18, 57, 65 |
| 886 | 13, 22, 57, 65 |
| 887 | 13, 24, 57, 65 |
| 888 | 13, 18, 56, 66 |
| 889 | 13, 18, 57, 66 |
| 890 | 13, 22, 57, 66 |
| 891 | 13, 24, 57, 66 |
| 892 | 13, 18, 56, 67 |
| 893 | 13, 18, 57, 67 |
| 894 | 13, 22, 57, 67 |
| 895 | 13, 24, 57, 67 |
| 896 | 13, 18, 56, 68 |
| 897 | 13, 18, 57, 68 |
| 898 | 13, 20, 56, 68 |
| 899 | 13, 22, 57, 68 |
| 900 | 13, 24, 57, 68 |
| 901 | 14, 46, 53, 59 |
| 902 | 14, 46, 53, 61 |
| 903 | 14, 18, 56, 61 |
| 904 | 14, 20, 56, 61 |
| 905 | 14, 22, 57, 61 |
| 906 | 14, 24, 57, 61 |
| 907 | 14, 22, 57, 62 |
| 908 | 14, 24, 57, 62 |
| 909 | 14, 28, 50, 62 |
| 910 | 14, 30, 50, 62 |
| 911 | 14, 32, 50, 62 |
| 912 | 14, 22, 57, 63 |
| 913 | 14, 24, 57, 63 |
| 914 | 14, 32, 50, 63 |
| 915 | 14, 22, 57, 64 |
| 916 | 14, 24, 57, 64 |
| 917 | 14, 46, 53, 65 |
| 918 | 14, 48, 53, 65 |
| 919 | 14, 18, 56, 65 |
| 920 | 14, 18, 57, 65 |
| 921 | 14, 20, 56, 65 |
| 922 | 14, 20, 57, 65 |
| 923 | 14, 22, 57, 65 |
| 924 | 14, 24, 57, 65 |
| 925 | 14, 46, 53, 66 |
| 926 | 14, 18, 56, 66 |
| 927 | 14, 20, 56, 66 |
| 928 | 14, 20, 57, 66 |
| 929 | 14, 22, 57, 66 |
| 930 | 14, 24, 57, 66 |
| 931 | 14, 46, 53, 67 |

TABLE 5-continued

Campylobacter Oligomer Combinations 23-29 minutes

| Combo No. | SEQ ID NOS. |
|---|---|
| 932 | 14, 18, 56, 67 |
| 933 | 14, 20, 56, 67 |
| 934 | 14, 20, 57, 67 |
| 935 | 14, 22, 57, 67 |
| 936 | 14, 24, 57, 67 |
| 937 | 14, 46, 53, 68 |
| 938 | 14, 48, 53, 68 |
| 939 | 14, 18, 56, 68 |
| 940 | 14, 18, 57, 68 |
| 941 | 14, 22, 57, 68 |
| 942 | 14, 24, 57, 68 |

A secondary screening was then performed on 22 oligonucleotide sets based on the initial screening. The oligos selected for secondary screening are as follows: T7 Provider SEQ ID NOS: 18, 20, 24, 28, 30, 32 and 48; Blocker SEQ ID NOS: 50, 53, 56 and 57; Primer SEQ ID NOS: 4, 7 and 12; and Torch SEQ ID NOS: 62, 63, 65, 66, 67 and 68. (See Table 6). These sets of oligos identified for secondary screening were selected based upon early emergence times as well as signal and curve shape and other favorable factors.

TABLE 6

Amplification Oligonucleotide Combinations for Secondary Screening

| Oligo Combination Number | T7 Provider (SEQ ID NO:) | Blocker (SEQ ID NO:) | Primer (SEQ ID NO:) | Torch (SEQ ID NO:) | Initial Screening TTime (minutes) |
|---|---|---|---|---|---|
| 2-1 | SEQ ID NO: 18 | SEQ ID NO: 56 | SEQ ID NO: 4 | SEQ ID NO: 63 | 21.9 |
| 2-2 | SEQ ID NO: 18 | SEQ ID NO: 56 | SEQ ID NO: 7 | SEQ ID NO: 63 | 19.6 |
| 2-3 | SEQ ID NO: 18 | SEQ ID NO: 56 | SEQ ID NO: 12 | SEQ ID NO: 63 | 19.0 |
| 2-4 | SEQ ID NO: 32 | SEQ ID NO: 50 | SEQ ID NO: 7 | SEQ ID NO: 63 | 19.3 |
| 2-5 | SEQ ID NO: 32 | SEQ ID NO: 50 | SEQ ID NO: 12 | SEQ ID NO: 63 | 33.0* |
| 2-6 | SEQ ID NO: 18 | SEQ ID NO: 56 | SEQ ID NO: 7 | SEQ ID NO: 68 | 24.2 |
| 2-7 | SEQ ID NO: 18 | SEQ ID NO: 56 | SEQ ID NO: 12 | SEQ ID NO: 68 | 24.3 |
| 2-8 | SEQ ID NO: 32 | SEQ ID NO: 50 | SEQ ID NO: 7 | SEQ ID NO: 68 | 18.3 |
| 2-9 | SEQ ID NO: 32 | SEQ ID NO: 50 | SEQ ID NO: 12 | SEQ ID NO: 68 | 20.2 |
| 2-10 | SEQ ID NO: 48 | SEQ ID NO: 53 | SEQ ID NO: 4 | SEQ ID NO: 63 | 23.7 |
| 2-11 | SEQ ID NO: 48 | SEQ ID NO: 53 | SEQ ID NO: 7 | SEQ ID NO: 63 | 20.4 |
| 2-12 | SEQ ID NO: 48 | SEQ ID NO: 53 | SEQ ID NO: 12 | SEQ ID NO: 63 | 17.7 |
| 2-13 | SEQ ID NO: 48 | SEQ ID NO: 53 | SEQ ID NO: 12 | SEQ ID NO: 68 | 28.0* |
| 2-14 | SEQ ID NO: 28 | SEQ ID NO: 50 | SEQ ID NO: 7 | SEQ ID NO: 68 | 18.8 |
| 2-15 | SEQ ID NO: 30 | SEQ ID NO: 50 | SEQ ID NO: 7 | SEQ ID NO: 68 | 18.7 |
| 2-16 | SEQ ID NO: 48 | SEQ ID NO: 53 | SEQ ID NO: 7 | SEQ ID NO: 68 | 23.4 |
| 2-17 | SEQ ID NO: 24 | SEQ ID NO: 57 | SEQ ID NO: 7 | SEQ ID NO: 68 | 25.8* |
| 2-18 | SEQ ID NO: 24 | SEQ ID NO: 57 | SEQ ID NO: 12 | SEQ ID NO: 68 | 26.3* |
| 2-19 | SEQ ID NO: 32 | SEQ ID NO: 50 | SEQ ID NO: 4 | SEQ ID NO: 63 | assayed in $2^{nd}$ screen only |
| 2-20 | SEQ ID NO: 32 | SEQ ID NO: 50 | SEQ ID NO: 7 | SEQ ID NO: 65 | 18.5 |
| 2-21 | SEQ ID NO: 32 | SEQ ID NO: 50 | SEQ ID NO: 7 | SEQ ID NO: 66 | 16.0 |
| 2-22 | SEQ ID NO: 32 | SEQ ID NO: 50 | SEQ ID NO: 7 | SEQ ID NO: 67 | 17.4 |

*Combinations chosen for secondary screening with TTimes higher than 23 minutes. These combinations comprise two or three oligo members that performed well in other combinations.

EXAMPLE 3

Secondary Screening of Amplification Oligomer Sets: Selectivity for *C. jejuni*, *C. lari*, and *C. coli* Target Nucleic Acids The amplification oligomer combinations of Table 6 were further tested for sensitivity to *C. jejuni*, *C. coli* and *C. lari* target nucleic acid, while discriminating from *C. upsaliensis* and *C. fetus*. Each combination was tested using 0, 1E2, 1E3 and 1E4 copies of *C. jejuni*, *C. lari*, *C. coli*, *C. fetus*, or *C. upsaliensis* 16S rRNA. Amplification oligos were present at 5.0 pM T7 Provider, 0.5 pM Blocker, 5.0 pM Primer and 4.0 pM Torch. Positive criterion was 1000 RFU using a PTI plate reader. Amplification oligomer combinations were able to amplify as few as 1E2 copies of *C. jejuni*, *C. lari*, or *C. coli* target nucleic acid. TTimes either emerged at very low levels or very late in the amplification reaction for *C. fetus* ssp fetus, *C. fetus* ssp *venerealis* and *C. upsaliensis*. Table 7. Oligo combination numbers (2-8) and (2-22) were selected for continued screening because in wells comprising these oligomer combinations in this secondary screening assay neither of the *C. fetus* species nor the *C. upsaliensis* species reacted and there was very good detection of *C. jejuni*, *C. coli*, and *C. lari*.

TABLE 7

Secondary Screening: Selectivity Screening Results.

| Oligo Combination Number (from Table 6) | *C. jejuni*; *C. coli*; and *C. lari* detection | *C. fetus*, *C. fetus* ssp *venerealis* detection | *C. upsaliensis* detection | Neg Control |
|---|---|---|---|---|
| 2-1 | (+) | (+) | (+) Low | Negative |
| 2-2 | (+) | (+) | (+) Low | Negative |

TABLE 7-continued

Secondary Screening: Selectivity Screening Results.

| Oligo Combination Number (from Table 6) | *C. jejuni*; *C. coli*; and *C. lari* detection | *C. fetus*, *C. fetus* ssp *venerealis* detection | *C. upsaliensis* detection | Neg Control |
|---|---|---|---|---|
| 2-3 | (+) | (+) | Negative | Negative |
| 2-4 | (+) | (+) | (+) Low | Negative |

TABLE 7-continued

Secondary Screening: Selectivity Screening Results.

| Oligo Combination Number (from Table 6) | C. jejuni; C. coli; and C. lari detection | C. fetus, C. fetus ssp venerealis detection | C. upsaliensis detection | Neg Control |
|---|---|---|---|---|
| 2-5  | (+) | (+) | Negative | Negative |
| 2-6  | (+) Low Slope | Negative | Negative | Negative |
| 2-7  | (+) | (+) | (+) Low | (+) Low |
| 2-8  | (+) | Negative | Negative | Negative |
| 2-9  | (+) | (+) | (+) Very Low | (+) Low |
| 2-10 | (+) | (+) | (+)Very Low | Negative |
| 2-11 | (+) | (+) | (+) Very Low | Negative |
| 2-12 | (+) | (+) | (+) Very Low | Negative |
| 2-13 | (+) | Negative | (+) Very Low | Negative |
| 2-14 | (+) | Negative | (+)Low | Negative |
| 2-15 | (+) | Negative | (+)Low | Negative |
| 2-16 | (+) | Negative | (+)Low | Negative |
| 2-17 | (+) | Negative | (+)Low | Negative |
| 2-18 | (+) | Negative | (+)Low | Negative |
| 2-19 | (+) | (+) | (+) Low | Negative |
| 2-20 | (+) | (+) | (+) Low | Negative |
| 2-21 | (+) | (+) Low | Negative | Negative |
| 2-22 | (+) | Negative | Negative | Negative |

An additional screen was performed using oligo combination from Table 6 to identify torches with sensitivity towards *C jejuni. C. lari*, and *C. coli* and discrimination against *C. upsaliensis* and *C. fetus*. Positive criterion was set at 0.05 RFU on a MJ Chrom4 instrument. These oligonucleotide sets were tested against 1E5 copies of target organism per reaction. Results of this additional screen indicated that oligo combinations comprising Torch oligonucleotides SEQ ID NOS:63 & 65 cross-react with *C. fetus*, while those comprising Torch SEQ ID NO:66 had only a very low signal to *C. fetus*. Oligo combinations comprising SEQ ID NOS:67-68 showed very good sensitivity towards *C jejuni. C. lari*, and *C. coli* and discrimination against *C. upsaliensis* and *C. fetus*.

EXAMPLE 4

Evaluation of Target Capture and Internal Control Integration

Three *Campylobacter* 16S rRNA target capture oligonucleotides (TCO) were tested using the SEQ ID NOS:7, 32, 50 & 68 amplification oligonucleotide combination. The target capture oligos included two *Campylobacter* TCOs based upon the sequence of *C. jejuni* 16S rRNA (SEQ ID NOS:71 & 73) and one wobble TCO (SEQ ID NO:58). An initial heating step is included in this assay to provide for hybridization of the *C. jejuni* based TCOs. The wobble TCO does not require a heating step, however, one was included to keep the conditions comparable for all three TCOs.

The method of target capture used with Kingfisher 96 is summarized in Table 8. Amplification and Enzyme reagents were reconstituted. A wash plate was prepared by filling a KF200 plate with 200 .micro.L/well of wash solution. An amp plate was prepared by filling another KF200 plate with 100 .micro.L/well of amplification reagent. Both the amp and wash plates were covered until used. A sample plate was prepared by adding 50 .micro.L TCR/well into a 2-mL, deep-well 96 plate (Axygen). The target was titrated from 1E5 copies per reaction to 1E1 copies per reaction in 10 .micro.L lysis solution. Specificity was included in the assay by testing *C. fetus* and *C. upsaliensis* at 1E5 copies per reaction. Negative controls include lysis reagent only. One ml of lysis solution was added to each well of the sample plate. With a repeat pipettor, 10 .micro.L of target solution was added to the appropriate deep wells. A deep-well tip-comb was placed in the sample plate. The covers for the wash and amp plates were removed. The KF96 protocol was started and all assay plates were placed on the KF96 instrument. The amp plate was placed in position 4, the wash plate in position 3, and the sample (deep-well plate) in position 1. Position 2 in the KF96 instrument was left empty. Once the plates were loaded, the KF96 instrument began the target capture step. When the KF96 run was completed, the plates were removed. From the amp plate, 30 .micro.L from each well were removed using a multi-channel pipettor and transferred to an MJ 96-well PCR plate.

TABLE 8

Kingfisher 96 Program.

| Step | Position | Step Description | Action | Beginning | Mix | End |
|---|---|---|---|---|---|---|
| 1 | 1 | Capture | Heat | 5 min-85. deg. C. | Very slow | No action |
| 2 | 1 | Capture | Heat | 15 min-65. deg. C. | Very slow | No action |
| 3 | 2 | Cool | Heat | 30 min-25. deg. C. (table rotated to empty position) | No action | No action |
| 4 | 1 | Mix prior to collect/collect Sample 1 | Mix | No action | 1 min-Very slow | Collect beads- count 20 |
| 5 | 3 | Release to Wash | Wash | Release 30 s Slow | 30 s Slow | No action |
| 6 | 1 | Capture Sample 2 | Wash | Release 30 s Very Slow (mix only) | 30 s Very Slow | Collect beads- count 20 |
| 7 | 3 | Release to Wash 2 | Wash | Release 30 s Slow | 30 s Slow | Collect beads- count 20 |
| 8 | 4 | Capture and release into Amp Soln | Wash | Release 30 s Slow | 30 s Slow | No action |

Results are shown in Table 9, and indicate that SEQ ID NOS:71 & 73 are equivalent to SEQ ID NO:58 for target capture. *C. fetus* and *C. upsaliensis* were not detected. *C. jejuni, C. coli* and *C. lari* were all detected at all target levels. SEQ ID NO:73 was selected for further *Campylobacter* detection assays.

TABLE 9

Target Capture Results.

| TCO | Target | Copies of Target (Times 10.sup.5) | Avg TTime (avg of 4 samples) |
|---|---|---|---|
| SEQ ID NO: 71 | C. fetus | 5 | n/a |
| | C. jejuni | 0 | n/a |
| | C. jejuni | 1 | 19.5 |
| | C. jejuni | 2 | 17.9 |
| | C. jejuni | 3 | 15.6 |
| | C. jejuni | 4 | 13.3 |
| | C. jejuni | 5 | 11.3 |
| | C. ups | 5 | n/a |
| SEQ ID NO: 73 | C. fetus | 5 | n/a |
| | C. jejuni | 0 | n/a |
| | C. jejuni | 1 | 19.8 |
| | C. jejuni | 2 | 17.4 |
| | C. jejuni | 3 | 15.3 |
| | C. jejuni | 4 | 13.2 |
| | C. jejuni | 5 | 10.9 |
| | C. ups | 5 | n/a |
| SEQ ID NO: 58 | C. fetus | 5 | n/a |
| | C. jejuni | 0 | n/a |
| | C. jejuni | 1 | 19.1 |
| | C. jejuni | 2 | 16.8 |
| | C. jejuni | 3 | 14.8 |
| | C. jejuni | 4 | 12.8 |
| | C. jejuni | 5 | 11.2 |
| | C. ups | 5 | n/a |
| SEQ ID NO: 71 | C. jejuni | 5 | 10.4 |
| | C. lari | 0 | n/a |
| | C. lari | 1 | 17.4 |
| | C. lari | 2 | 16.0 |
| | C. lari | 3 | 12.7 |
| | C. lari | 4 | 11.0 |
| | C. lari | 5 | 8.4 |
| | C. ups | 5 | 21.2* |
| SEQ ID NO: 73 | C. jejuni | 5 | 10.0 |
| | C. lari | 0 | n/a |
| | C. lari | 1 | 18.2 |
| | C. lari | 2 | 15.5 |
| | C. lari | 3 | 12.9 |
| | C. lari | 4 | 10.3 |
| | C. lari | 5 | 8.1 |
| | C. ups | 5 | 21.6* |
| SEQ ID NO: 58 | C. jejuni | 5 | 10.5 |
| | C. lari | 0 | n/a |
| | C. lari | 1 | 18.1 |
| | C. lari | 2 | 15.6 |
| | C. lari | 3 | 12.8 |
| | C. lari | 4 | 10.2 |
| | C. lari | 5 | 8.3 |
| | C. ups | 5 | n/a |
| SEQ ID NO: 71 | C. jejuni | 5 | 8.3 |
| | C. coli | 0 | n/a |
| | C. coli | 1 | 16.6 |
| | C. coli | 2 | 14.4 |
| | C. coli | 3 | 12.0 |
| | C. coli | 4 | 10.1 |
| | C. coli | 5 | 7.5 |
| | C. ups | 5 | n/a |
| SEQ ID NO: 73 | C. jejuni | 5 | 7.9 |
| | C. coli | 0 | n/a |
| | C. coli | 1 | 16.7 |
| | C. coli | 2 | 14.5 |
| | C. coli | 3 | 12.4 |
| | C. coli | 4 | 10.0 |
| | C. coli | 5 | 7.8 |
| | C. ups | 5 | n/a |
| SEQ ID NO: 58 | C. jejuni | 5 | 8.1 |
| | C. coli | 0 | n/a |

TABLE 9-continued

Target Capture Results.

| TCO | Target | Copies of Target (Times 10.sup.5) | Avg TTime (avg of 4 samples) |
|---|---|---|---|
| | C. coli | 1 | 15.9 |
| | C. coli | 2 | 13.5 |
| | C. coli | 3 | 11.6 |
| | C. coli | 4 | 9.2 |
| | C. coli | 5 | 7.1 |
| | C. ups | 5 | n/a |

*1 of 4 samples showed a positive TTime for both test conditions.

Thus, from these assays, it was determined to do further testing on amplification oligo set SEQ ID NOS:7, 32, 50 & 68, using a target capture probe SEQ ID NO:73.

EXAMPLE 5

Sensitivity, Specificity, Interference and Limit of Detection

Sensitivity Testing. *Campylobacter jejuni* (ATCC 33560) was assayed at 1E5 copies per reaction. Lysis buffer was used as the negative control. Twenty positives (1E5 copies of rRNA per assay) were tested using the KingFisher 96 instrument for target capture, an Eppendorf thermomixer for annealing the primers and for enzyme addition, and the PTI-FP-2® FluoDia plate reader was used for detection. Twenty negative control reactions were included. The input for target capture was 1 mL, the output for target capture was 100 .micro.L, of which 30 .micro.L was used in the amplification. Positive criterion was set at 1000 RFUs. Nineteen of 20 replicates were to be detected with a >95% positivity rate. If less than 19 replicates were positive after an initial round of testing, then 40 additional replicates were to be tested. Testing for sensitivity at this stage yielded a 100% rate of positivity and a 10% rate of false positivity. The false positives seen at this stage emerged at very low levels and very late in the amplification process. Because the 1000 RFU criterion for positives was not an optimized criterion, the false positives are not considered true false positives. These conditions were evaluated again in an additional round of testing. Results are shown in Table 10.

TABLE 10

Sensitivity Results

| Sample ID | Target Amt (copies/rxn) | Total Replicates | Number Positive | Avg TTime |
|---|---|---|---|---|
| C. jejuni ATCC33560 | 1E5 | 20 | 20 | 15.9 |
| No Target-CP0.0 | 0 | 20 | 2 | 14.8 |

Specificity Testing. Organisms that were closely related to the target organism but were genotypically distinct by rRNA analysis were selected as negatives. Seven challenge organisms were tested at 1E5 copies per reaction using the KingFisher mL instrument for target capture, an Eppendorf thermomixer for annealing the primers and for enzyme addition, and the PTI-FP-2® FluoDia plate reader was used for detection. Challenge organisms were *C. fetus* ssp *venerealis; C. fetus* ssp *fetus; C. fecalis; E. coli; C. upsaliensis; S. enteritidis;* and *H. pylori*. The positive control was *C. jejuni* (ATCC 33560) at 1E4 copies per positive control reaction. Lysis solution was used as negative control. All organisms were tested in replicate reactions. The positive criterion was set at 1000 RFU. Less than or equal to 7 of 140 reaction should be positive. Twenty-eight negative control reactions were included. The input for target capture was 1 mL; the output for target capture was 100 .micro.L, of which 30 .micro.L was used in the amplification. Testing for specificity at this stage yielded about a 98% rate of success in discriminating against the challenge organisms (3/140 were positive; all *E. coli* reaction wells) and false positive reactions were detected in 2 of 84 negative reaction wells. Thus, false positive rates in the *E. coli* wells are similar those in the negative control wells. The positive control was 100% positive. Table 11.

TABLE 11

Specificity Results.

| Organism | Copies per Reaction | Percent Positive |
| --- | --- | --- |
| *C. fetus* ssp *venerealis* | 1E5 | 0% |
| *C. fetus* ssp. *fetus* | 1E5 | 0% |
| *C. fecalis* | 1E5 | 0% |
| *E. coli* | 1E5 | 0.5% |
| *C. upsaliensis* | 1E5 | 0% |
| *S. enteritidis* | 1E5 | 0% |
| *H. pylori* | 1E5 | 0% |
| *C. jejuni* (positive) | 1E4 | 100% |
| Negative | 0 | 2.4% |

Interference Testing. The goal of this assay is to detect *C. jejuni* 16S rRNA at a concentration of 1E3 copies (1 CFU) per sample in the presence of 0 copies (lysis solution only) or 1E7 copies of nearest neighbor organisms. Seven nearest neighbor challenge organism were tested, which were as follows: *C. fetus* ssp *venerealis; C. fetus* ssp *fetus; C. fecalis; E. coli; C. upsaliensis; S. enteritidis;* and *H. pylori. C. jejuni* was used as the baseline target at 1E3 copies. Assays were performed using the KingFisher96 and the PTI reader. All conditions were tested in replicates of 12, with a positive criterion of 1000 RFU. Interference testing showed 100% positivity for detection of *C. jejuni* in the presence of *C. fecalis; E. coli; C. upsaliensis; S. enteritidis;* and *H. pylori*. However, detection of *C. jejuni* in the presence of *C. fetus* ssp *venerealis; C. fetus* ssp fetus yielded 0% positivity and 8.3% positivity, respectively. In a follow-up assay, the interfering *C. fetus* species were similarly tested in combination with *C. coli* and *C. lari* and the *C. fetus* species interfered with detection. The tested *C. fetus* species interfere with detection of *C. jejuni, C. coli* and *C. lari* target nucleic acid using the current amplification oligo combination.

EXAMPLE 6

Testing an Oligomer Set Using a Variety of T7 Providers

Additional T7 Provider oligomers were prepared and tested. The T7 Providers are shown in Table 12, below. Each of the T7 Providers in Table 12 were used in an oligomer combination that included SEQ ID NOS:7, 50 & 68, and one of the T7 Providers. In one condition. the Blocker (SEQ ID NO:50) was not included and so the combination in this reaction was SEQ ID NOS:7, 26, 68.

TABLE 12

Various T7 Providers

| SEQ ID NO: | Sequence (5'→3') |
| --- | --- |
| 32 | aatttaatacgactcactatagggagaCAGTTGGAAACGACTGCTAATACTCT |
| 84 | aatttaatacgactcactatagggagaCAGTTGGAAACGACTGCTAAT |
| 85 | aatttaatacgactcactatagggagaCAGTTGGAAACGACTGCTA |
| 86 | aatttaatacgactcactatagggagaCAATTGGAAACGACTGCTAATACTCT |
| 87 | aatttaatacgactcactatagggagaCAGTTGGAAACGACTGCCAACACTCT |
| 88 | aatttaatacgactcactatagggagaCAGTTGGAAACGACTGCTAACAC |
| 26 | aatttaatacgactcactatagggagaAAGAGGACAACAGTTGGAAAC |

The amplification oligo combinations were screened for sensitivity to *C. jejuni, C. coli* and *C. lari* target nucleic acids. A subset of these combinations of amplification oligomers was then screened for interference and cross-reactivity by nearest neighbors. Sensitivity assays were set up as has been generally described herein. *C. jejuni* (ATCC 33291), *C. coli* (ATCC 33559) and *C. lari* (ATCC 35221) were tested at a level of 0, 1E2, 1E3 or 1E4 copies per reaction. Negative control was oligoless amplification reagent. Positive selection criterion was at least 2 of 3 samples having 1000 RFU for the 1E2 reaction and 3 of 3 samples having a TTime for RFU 1000 no greater than 20 minutes for the 1E4 reaction. Three amplification oligo combinations performed well for sensitivity testing.

Interference Testing. A control amplification oligo combination and the three amplification oligos combinations that performed best in the sensitivity testing were then further tested for interference using one of the following inclusive organisms, *C. jejuni* (ATCC 33291), *C. coli* (ATCC 33559) or *C. lari* (ATCC 35221), each combined with one of the following near neighbor challenge organisms, *C. fetus* ssp *fetus, C. fetus* ssp *venerealis, C. upsaliensis* or *Archobacter blutzleri*. Inclusive organisms were tested at 1E5 copies per reaction and challenge organisms were tested at 1E8 copies per reaction. Positive controls were *C. jejuni* (ATCC 33291) at 1E5 copies per reaction without challenge organism. Negative controls were oligoless amplification reagent. Assays were performed using the KingFisher 96 and the PTI reader. Reactions were run in replicates of 12, and positive criterion was 1000 RFU.

All positive controls amplified appropriately and all negative controls had no false positives. Oligomer combinations with SEQ ID NOS:7, 32, 50 & 68, SEQ ID NOS:7, 86, 50 & 68, and to a lesser extent with SEQ ID NOS:7, 84, 50 & 68 showed some interference by *C. fetus* ssp. *fetus* and *C. fetus* ssp. *venerealis*. No interference was seen with amplification oligo combination SEQ ID NO:7, 26, 50 & 68. All three of these amplification oligo combinations were then tested for cross-reactivity.

Cross-Reactivity Testing. Cross-reactivity of the amplification oligos was tested against 1E8 copies per reaction of *C. fetus* ssp *fetus, C. fetus* ssp *venerealis, C. upsaliensis* and *Archobacter blutzleri*. Positive controls were *C. jejuni* (ATCC 33291) at 1E5 copies per reaction. Negative controls were oligoless amplification reagent. Reactions were run in replicates of 4 and positive criterion was 1000 RFU. Positive controls amplified appropriately and no false positives were detected. Late, low-slope detection was seen for amplification oligo combination SEQ ID NO:7, 26, 50 & 68 (average TTime 29.4 minutes), but not with other amplification oligo combinations being tested. Oligomer combination SEQ ID NO:7, 26, 50 & 68 was used for testing a pure culture lysates in buffered-peptone water.

EXAMPLE 7

Sensitivity, Specificity, Limit of Detection, and Analytical Testing for Target Nucleic Acids in Pure Culture Lysates An oligomer combination was used for testing a pure culture lysates in buffered-peptone water (BPW). Sample preparation device was not included. All positive controls were *C. jejuni* (ATCC 33560) and all negative controls were lysis/BPW. All samples are in a 70:30 lysis solution:BPW. The amplification oligos are SEQ ID NOS:7, 26, 50 & 68. The target capture oligo is SEQ ID NO:73.

Sensitivity. *Campylobacter jejuni* (ATCC 33560), *C. coli* (ATCC 43478), and *C. lari* (ATCC 35222) were assayed at 1E4-5E4 copies per reaction. Lysis buffer was used as the negative control. Twenty positives (1E5 copies of rRNA per assay) were tested using the KingFisher 96 instrument for target capture, an Eppendorf thermomixer for annealing the primers and for enzyme addition, and the PTI-FP-2® FluoDia plate reader was used for detection. Twenty negative control reactions were included. The input for target capture was 1 mL, the output for target capture was 100 .micro.L, of which 30 .micro.L was used in the amplification. Positive criterion was set at 1000 RFUs. Nineteen of 20 replicates were to be detected with a >95% positivity rate. If less than 19 replicates were positive after an initial round of testing, then 40 additional replicates were to be tested. Testing for sensitivity at this stage yielded a 100% rate of positivity and a 10% rate of false positivity.

Specificity. Specificity of the amplification oligo combination was challenged using near neighbor exclusionary organisms. Exclusionary organisms were tested at 1E6 copies per reaction using the KingFisher 96 and PTI detector. Exclusionary organisms were *C. fetus* ssp *venerealis*; *C. fetus* ssp *fetus*; *C. fecalis*; *E. coli*; *C. upsaliensis*; *S. enteritidis*; and *H. pylori*. The positive control was *C. jejuni* (ATCC 33560) at 1E5 copies per positive control reaction. Lysis solution was used as negative control. All organisms were tested in replicate reactions. The positive criterion was set at 1000 RFU. Specificity testing yielded a 100% rate of success in discriminating against the challenge organisms. The *E. coli* reactions yielded 0 false positives, thus not showing the false positive rate that appeared in earlier testing. The positive control was 100% positive. The negative controls showed no false positives.

Limit of Detection. *C. jejuni* (ATCC 33560 and 49351), *C. coli* (ATCC 43478 and 43488), and *C. lari* (ATCC 35222 and 43675) were tested a level of 1E3 to 1E4 copies RNA/assay (approximately 1-10 CFU). The actual assay input for each *Campylobacter* species was 5E3 copies. Target capture was performed on the Kingfisher 96 and the detection on the PTI reader. Each species was tested in replicates of 20, from which one 30 .micro.L replicate was amplified. The positive criterion for this section was 1000 RFU, and 19 of 20 replicates must reach this criterion to be considered positive. Note that ATCC 33560 is considered both the positive control as well as a strain required for testing. It was included as a positive control on the plate where it was not tested at 5E3 copies/assay. Results indicated a 100% success rate (20 of 20 replicates) for detecting each of these *Campylobacter* species. There were no false positives.

Analytical Testing. The number of organisms tested was expanded to include twenty-five organisms for detection and fifteen challenge organisms. The organisms were tested at 1E5 copies/assay (approximately 100 CFU). Testing was performed on the Kingfisher 96 instrument for target capture and the PTI reader for detection. All were tested in replicate reactions of 3, from which one 30 .micro.L replicate was amplified. For the inclusives, a positive reading in at least 2 of 3 replicates and for the exclusives, no more than 1 of 3 replicates should be positive. If these criteria are not met for any organism, testing for that species/strain will be repeated in replicates of 12. The inclusive organisms tested are *C. jejuni*, *C. jejuni* ssp *doylei*, *C. coli*, and *C. lari*. The exclusive organisms tested are *E. coli*, *E. coli* O157:H7, *E. vulnaris*, *E. hermannii*, *Enterobacter cloacae*, *S. enteriditis*, *Edwardsiella hoshinae*, *P. mirabilis*, *Citrobacter brakii*, *Pseudomonas fluorescens*, *Shigella flexneri*, *Aeromonas hydrophila*, *Arcobacter butzleri*, *Campylobacter upsaliensis* and *Campylobacter fetus* ssp *fetus*. Positive control was *C. jejuni* (ATCC 33560). All of the inclusive organisms yielded 100% positive detection except for two of 16 tested strains of *C. jejuni* (ATCC 35920 and 35925). These two strains of *C. jejuni* yielded 0 of 3 positives. None of the exclusive organisms yielded any positive results. Positive controls were 100% and there were no false positives.

EXAMPLE 8

Testing an Oligomer Set Using a Variety of Torches

*C. jejuni* species ATCC 35925 and ATCC 35920 (ATCC, Manassas, Va.) were not detected in the above analytical testing. Based on sequencing of a region of interest within the target sequence for these strains of *C. jejuni*, it was determined that each strain contained a single point mutation in their nucleotide sequences corresponding to a Torch hybridization region. The location of the point mutation was different for each strain. (SEQ ID NOS:89-90).

Sensitivity. During the secondary screening process multiple candidate torches were considered acceptable based on specificity and sensitivity condition at that time. For this follow-up experiment, amplification oligo combinations comprising alternate Torch SEQ ID NOS:67 or original Torch SEQ ID NO:68 were screened again against *C. jejuni* ATCC 35925 and 35920 at 1E5 copies per reaction. Oligo combinations used were: SEQ ID NOS:7, 32, 50 & 67; SEQ ID NOS:7, 32, 50 & 68; SEQ ID NOS:7, 26, 50 & 67; and SEQ ID NOS:7, 26, 50 & 68. *C. jejuni* (ATCC 33560) was used as a positive control and lysis solution only as the negative control. The Kingfisher 96 instrument was used for the target capture and the PTI reader for the detection. Acceptable alternative amplification oligo combinations will detect of *C. jejuni* ATCC 35920 and 35925 while still excluding nearest neighbors. Positive criterion was set at 1000 RFU.

Control *C. jejuni* ATCC 33560 was detected with 100% positivity rate using amplification oligo combinations having Torch SEQ ID NO:67 or SEQ ID NO:68. The SEQ ID NO:67 assays showed a lower average RFU than did the SEQ ID NO:68 assays. There were no false positives. For detection of *C. jejuni* ATCC 35920, the SEQ ID NO:67 amplification oligo combinations were 100% positive. The SEQ ID NO:68 combinations could not detect *C. jejuni* above background. All amplification oligo combinations had a single false positive result. For detection of *C. jejuni* ATCC 35925, both the SEQ ID NO:67 and the SEQ ID NO:68 amplification oligo combinations were 100% positive; however SEQ ID NO:67 resulted in a higher average RFU than did SEQ ID NO:68. Amplification oligo combinations comprising SEQ ID NO:67 were then tested for discrimination against exclusionary organisms.

Selectivity. Two analytical tests for exclusive species were performed using amplification oligo combinations comprising SEQ ID NO:67 and twelve exclusionary organisms in a first assay followed by three exclusionary organisms in a second assay. The second assay was performed to retest false positives identified in the first. The exclusionary organisms for the first assay were provided at 1E5 copies per reaction and included *A. butzleri, C. fecalis, C. fetus* ssp. *fetus, C. fetus* ssp. *fetus, C. fetus* ssp. *venerealis, C. upsaliensis, C. upsaliensis, E. coli, E. faecalis, E. faecium, P. fluorenscens* and *S. enteritidis*. Positive control was 1E5 copies per reaction of *C. jejuni* ATCC 33560 and negative control was lysis solution. All reactions were in replicates of three. No more than 1 of 3 reactions should be positive for the exclusionary organisms tested. All exclusionary organisms were 100% negative except for *C. upsaliensis, E. faecalis* and *S. enteritidis*; each of which had 1 of 3 false positive reactions.

Though 1 of 3 false positives meets the criteria for a negative reaction, a second assay was performed on the each of the species showing a single false positive result. In this assay the exclusionary organisms were provided at 1E5 copies per reaction and included *C. upsaliensis, E. faecalis* and *S. enteritidis*. Positive control was 1E5 copies per reaction of *C. jejuni* ATCC 33560 and negative control was lysis solution. All reactions were in replicates of eight. No more than 1 of 8 reactions should be positive for the exclusionary organisms tested. All exclusionary organisms were negative for 7 of 8 reactions. Amplification oligo reactions comprising Torch SEQ ID NO:67 overcome the loss of sensitivity for *C. jejuni* ATCC 35920 and 35925 that was seen above with SEQ ID NO:68.

EXAMPLE 9

Poultry Rinsate Testing

To test the functionality of the prototype *Campylobacter* assay, twenty poultry rinsates were prepared. Rinsates were obtained by placing a whole defeathered chicken carcass (approximately 2-5 pounds) in a large sealable plastic bag with 400 mL of buffered peptone water (BPW). The BPW was distributed over the chicken by shaking the bag and using manual exertion on the outside of the bag. All reactions were in replicates of four. Direct detection of *Campylobacter* was performed by assaying 500 .micro.L of rinsate using amplification oligo combination SEQ ID NOS:7, 26, 50 & 67 and the target capture oligo SEQ ID NO:73. *Campylobacter* and internal control amplification oligos were used at the following concentrations: 5 pM T7 Provider, 0.5 pM Blocker, 5 pM Primer and 8 pM Torch. Rinsates were also assayed using a culture method substantially similar to the USDA recommended culture methods for compare. *Campylobacter jejuni* ATCC 33291 was the positive control at 1E5 copies per reaction. Lysis buffer was used as the negative control. Assays using the KingFisher 96 instrument for target capture, an Eppendorf thermomixer for annealing the primers and for enzyme addition, and the PTI-FP-2® FluoDia plate reader for detection. The input for target capture was 500 .micro.L, the output for target capture was 100 .micro.L, of which 30 .micro.L was used in the amplification. Positive criterion was set at 1000 RFUs. Amplification of *Campylobacter* was found for all rinsates with a mean and median TTime of 18.7 minutes. No false positives were detected. Table 13. Using the USDA culture method there was no detection of *Campylobacter* species in any of these rinsates.

TABLE 13

Rinsate Average TTimes

| Sample ID | Avg TTime |
|---|---|
| Rinsate #1 | 19.4 |
| Rinsate #2 | 22.6 |
| Rinsate #3 | 20.8 |
| Rinsate #4 | 16.4 |
| Rinsate #5 | 22.4 |
| Rinsate #6 | 20.9 |
| Rinsate #7 | 18.4 |
| Rinsate #8 | 16.6 |
| Rinsate #9 | 18.6 |
| Rinsate #10 | 16.7 |
| Rinsate #11 | 18.8 |
| Rinsate #12 | 17.3 |
| Rinsate #13 | 19.6 |
| Rinsate #14 | 18.9 |
| Rinsate #15 | 15.6 |
| Rinsate #16 | 18.2 |
| Rinsate #17 | 16.7 |
| Rinsate #18 | 19.7 |
| Rinsate #19 | 17.0 |
| Rinsate #20 | 18.9 |
| Non Template | 28.1 |
| Positive Control | 19.0 |

In summary, real-time TMA technology was suitable for rapid, highly sensitive detection of food-borne pathogens. The assay had a sensitivity of 5E3 target nucleic acid copies/assay (approximately 10 CFU) for the desired species, *C. jejuni, C. coli* and *C. lari*, while excluding various nearest neighbors and potentially co-contaminating flora at 1E7 target nucleic acids copies/assay (approximately 10,000 CFU). The data demonstrated a rapid test format that allowed screening of food samples for *Campylobacter* within a single 8-hour work shift.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents.

The methods illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed. Thus, it should be understood that although the present invention has been specifically disclosed by preferred embodiments and optional features, modification and variation of the invention embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the methods. This includes the generic description of the methods with a proviso or negative limitation removing any subject matter from the genus, regardless of whether or not the excised material is specifically recited herein.

Other embodiments are within the following claims. In addition, where features or aspects of the methods are described in terms of Markush groups, those skilled in the art will recognize that the invention is also thereby described in terms of any individual member or subgroup of members of the Markush group.

The invention claimed is:

1. A method for specifically detecting a *Campylobacter* target nucleic acid in a sample comprising the steps of:
   (a) obtaining a sample suspected of containing at least a *Campylobacter* target nucleic acid;
   (b) contacting said sample with at least two amplification oligomers that stably hybridize to a *C. jejuni* target nucleic acid and a *C. coli*, a *C. lari* or a *C. coli* and a *C. lari* target nucleic acid, wherein a first of said amplification oligomers comprises a target hybridizing sequence that is 15 to 45 nucleotides in length and is configured to target a sequence in a region of a *Campylobacter* 16S rRNA gene corresponding to nucleotides 108 to 150 of GenBank Accession No.: AF393202.1, gi:20378208 and wherein a second of said amplification oligomers comprises the sequence of SEQ ID NO: 7;
   (c) performing an in vitro nucleic acid amplification reaction wherein any of a *C. jejuni* target nucleic acid, a *C. coli* target nucleic acid and a *C. lari* target nucleic acid present in said sample is used as a template for generating an amplification product; and
   (d) performing a nucleic acid detection reaction that detects said amplification product to determine whether a *Campylobacter* target nucleic acid was present in said sample.

2. The method of claim 1, wherein said in vitro nucleic acid amplification reaction is a transcription mediated amplification reaction, a strand displacement reaction or a polymerase chain reaction.

3. The method of claim 1, wherein said first of said amplification oligomers comprises a target hybridizing sequence configured to target a sequence in a region of a *Campylobacter* 16S rRNA gene selected from the group consisting of: a region corresponding to nucleotides 115 to 150 of GenBank Accession No.: AF393202.1, gi:20378208; a region corresponding to nucleotides 115 to 135 of GenBank Accession No.: AF393202.1, gi:20378208; and a region corresponding to nucleotides 125 to 150 of GenBank Accession No.: AF393202.1, gi:20378208.

4. The method of claim 3, wherein said first of said amplification oligomers comprises SEQ ID NO:26.

5. The method of claim 1, wherein said first of said amplification oligomers is a promoter based amplification oligomer further comprising a 5' promoter sequence.

6. The method of claim 1, wherein step (b) further comprises contacting said sample with a blocker oligomer.

7. The method of claim 1, wherein said nucleic acid detection reaction comprises contacting said amplification product with a detection probe oligomer configured to hybridize to a portion of said amplification product.

8. The method of claim 7, wherein said detection is real-time detection.

9. The method of claim 7, wherein said detection oligomer consists essentially of SEQ ID NO:67.

10. The method of claim 1, wherein said nucleic acid detection reaction comprises contacting said amplification product with a detection probe oligomer consisting of SEQ ID NO:67.

11. The method of claim 10, wherein said first amplification oligomer is SEQ ID NO:26.

12. The method of claim 1, further comprising the step of contacting said sample suspected of containing a *Campylobacter* target nucleic acid with a target capture oligomer.

13. The method of claim 1, wherein said sample further contains nucleic acid from one or more bacteria closely related to *C. jejuni; C. coli*, or *C. lari* and said target nucleic acid is specifically detected in said sample.

14. The method of claim 13, wherein said one or more bacteria is at least one of: *C. Fetus*, ssp. *fetus, C. fetus* ssp *venerealis, C. upsaliensis, E. coli, C. fecalis, S. enteridis, H. pylori, E. vulnaris, E. hermannii, Enterobacter cloacae, Edwardsiella hoshinae, P. miribalis, Citrobacter brakii, Pseudomonas fluorescens, Shigella flexneri, Aeromonas hydrophila*, and *A. butzleri*.

15. The method of claim 13, wherein at step (c) said target nucleic acid is specifically amplified.

\* \* \* \* \*